(12) United States Patent
Satofuka et al.

(10) Patent No.: US 10,214,584 B2
(45) Date of Patent: Feb. 26, 2019

(54) THERAPEUTIC PHARMACEUTICAL COMPOSITION EMPLOYING ANTI-SLC6A6 ANTIBODY

(71) Applicant: ORDER-MADE MEDICAL RESEARCH INC., Kashiwa-shi, Chiba (JP)

(72) Inventors: Hiroyuki Satofuka, Chiba (JP); Kensuke Ohse, Chiba (JP); Shigeki Mukobata, Chiba (JP); Hirotada Akiyama, Chiba (JP); Masaya Ohtsu, Chiba (JP); Yoko Okabe, Chiba (JP); Yasufumi Murakami, Chiba (JP)

(73) Assignee: ORDER-MADE MEDICAL RESEARCH INC., Kashiwa-Shi (JP)

( * ) Notice: Subject to any disclaimer, the term of this patent is extended or adjusted under 35 U.S.C. 154(b) by 0 days.

(21) Appl. No.: 15/111,117

(22) PCT Filed: Jan. 15, 2015

(86) PCT No.: PCT/JP2015/051586
§ 371 (c)(1),
(2) Date: Jul. 12, 2016

(87) PCT Pub. No.: WO2015/108203
PCT Pub. Date: Jul. 23, 2015

(65) Prior Publication Data
US 2016/0333092 A1 Nov. 17, 2016

(30) Foreign Application Priority Data
Jan. 15, 2014 (JP) .................................. 2014-005348

(51) Int. Cl.
| | | |
|---|---|---|
| C07K 16/28 | (2006.01) | |
| A61K 51/10 | (2006.01) | |
| A61K 45/06 | (2006.01) | |
| C07K 16/30 | (2006.01) | |
| A61K 39/395 | (2006.01) | |
| A61K 47/68 | (2017.01) | |

(52) U.S. Cl.
CPC .......... *C07K 16/28* (2013.01); *A61K 39/3955* (2013.01); *A61K 45/06* (2013.01); *A61K 47/6843* (2017.08); *A61K 51/1051* (2013.01); *A61K 51/1063* (2013.01); *A61K 51/1072* (2013.01); *C07K 16/30* (2013.01); *C07K 16/3015* (2013.01); *C07K 16/3046* (2013.01); *C07K 16/3069* (2013.01); *C07K 2317/24* (2013.01); *C07K 2317/565* (2013.01); *C07K 2317/76* (2013.01); *C07K 2317/77* (2013.01)

(58) Field of Classification Search
CPC ............ A61K 47/6843; C07K 2317/24; C07K 2317/77; C07K 2317/565; C07K 2317/76
USPC ............................................ 424/133.1, 178.1
See application file for complete search history.

(56) References Cited

U.S. PATENT DOCUMENTS

| | | |
|---|---|---|
| 8,158,757 B2 | 4/2012 | Gurney et al. |
| 8,158,758 B2 | 4/2012 | Gurney |
| 8,481,683 B2 | 7/2013 | King et al. |
| 8,540,989 B2 | 9/2013 | Gurney |
| 8,628,774 B2 | 1/2014 | Gurney et al. |
| 8,883,736 B2 | 11/2014 | Gurney |
| 9,040,044 B2 | 5/2015 | Gurney et al. |
| 9,328,160 B2 | 5/2016 | Ishii et al. |
| 2005/0037439 A1* | 2/2005 | Bourner ................ C07K 16/28 435/7.2 |
| 2005/0181368 A1 | 8/2005 | Patel |
| 2009/0074782 A1 | 3/2009 | Gurney |
| 2009/0191205 A1 | 7/2009 | Gurney |
| 2010/0143368 A1 | 6/2010 | King et al. |
| 2013/0115206 A1 | 5/2013 | Gurney et al. |
| 2013/0121993 A1 | 5/2013 | Gurney |
| 2013/0230530 A1 | 9/2013 | King et al. |
| 2013/0230869 A1* | 9/2013 | Satofuka ............ C07K 16/3046 435/7.92 |
| 2013/0317201 A1 | 11/2013 | Ishii et al. |
| 2013/0336970 A1 | 12/2013 | Gurney |
| 2014/0134177 A1 | 5/2014 | Gurney et al. |
| 2015/0165024 A1 | 6/2015 | Gurney |
| 2015/0337050 A1 | 11/2015 | Gurney et al. |
| 2016/0009799 A1* | 1/2016 | Satofuka ................ C07K 16/28 530/387.3 |
| 2016/0367667 A1 | 12/2016 | Gurney et al. |
| 2017/0313770 A1* | 11/2017 | Satofuka ................ C07K 16/28 |

FOREIGN PATENT DOCUMENTS

| | | |
|---|---|---|
| EP | 1961428 A1 | 8/2000 |
| EP | 2562188 A2 | 2/2013 |

(Continued)

OTHER PUBLICATIONS

SLC6A6 solute carrier family 6 member 6 [*Homo sapiens* (human)]—Gene ID: 6533, updated on Aug. 6, 2017—NCBI (pp. 1-11; Aug. 8, 2017).*

(Continued)

*Primary Examiner* — Lynn A Bristol
(74) *Attorney, Agent, or Firm* — Birch, Stewart, Kolasch & Birch, LLP

(57) ABSTRACT

The present invention aims to provide a pharmaceutical composition for cancer treatment, which comprises a novel monoclonal antibody binding to SLC6A6 or its extracellular region and a chemotherapeutic agent conjugated therewith, as well as a therapeutic method in which the monoclonal antibody or a therapeutic agent composed of the monoclonal antibody conjugated with a chemotherapeutic agent is used in combination with a chemotherapeutic agent. The present invention provides a pharmaceutical composition comprising an antibody conjugate configured such that a monoclonal antibody having higher affinity than conventional antibodies and recognizing native SLC6A6 or a native polypeptide of an extracellular region of SLC6A6 is conjugated with an anticancer agent or the like having activity against cancer and other hyperproliferative diseases.

1 Claim, 17 Drawing Sheets
(2 of 17 Drawing Sheet(s) Filed in Color)
Specification includes a Sequence Listing.

(56) References Cited

FOREIGN PATENT DOCUMENTS

| EP | 2735571 A2 | 5/2014 |
|---|---|---|
| JP | 2010-511388 A | 4/2010 |
| JP | 2010-532169 A | 10/2010 |
| WO | WO 2004/110345 A2 | 12/2004 |
| WO | WO 2012/029990 A1 | 3/2012 |
| WO | WO 2012/057328 A1 | 5/2012 |
| WO | WO 2012/156018 A1 | 11/2012 |
| WO | WO 2013/133450 A1 | 9/2013 |

OTHER PUBLICATIONS

Satofuka et al. (Biochemical and Biophysical Research Communications 450 (2014) 99-104; . Epub May 24, 2014).*
Extended European Search Report for European Application No. 15737917.3, dated Nov. 7, 2017.
Bengala et al., "Cardiac toxicity of trastuzumab in metastatic breast cancer patients previously treated with high-dose chemotherapy: a retrospective study", British Journal of Cancer, vol. 94, 2006, pp. 1016-1020.
International Search Report issued in PCT/JP2015/051586, dated Apr. 14, 2015.
Written Opinion of the International Searching Authority (PCT/ISA/237) issued in PCT/JP2015/051586, dated Apr. 14, 2015.
Presta et al., "Humanization of an Anti-Vascular Endothelial Growth Factor Monoclonal Antibody for the Therapy of Solid Tumors and Other Disorders", Cancer-Research, vol. 57, Oct. 15, 1997, pp. 4593-4599.
Saltz et al., "Phase II Trial of Cetuximab in Patients With Refractory Colorectal Cancer That Expresses the Epidermal Growth Factor Receptor", Journal of Clinical Oncology, vol. 22, No. 7, Apr. 1, 2004, pp. 1201-1208.
Satofuka et al., "Immunization method for multi-pass membrane proteins using highly metastatic cell lines", Biochemical and Biophysical Research Communications.; vol. 450, No. 1, May 24, 2014, pp. 99-104.
Todaro et al., "Colon Cancer Stem Cells: Promise of Targeted Therapy", Gastroentrology, vol. 138, No. 6, 2010, pp. 2151-2162.
Woelk et al., "The ubiquitination code: a signalling problem", Cell Division, vol. 2, No. 11, Mar. 13, 2007, pp. 1-12.

* cited by examiner

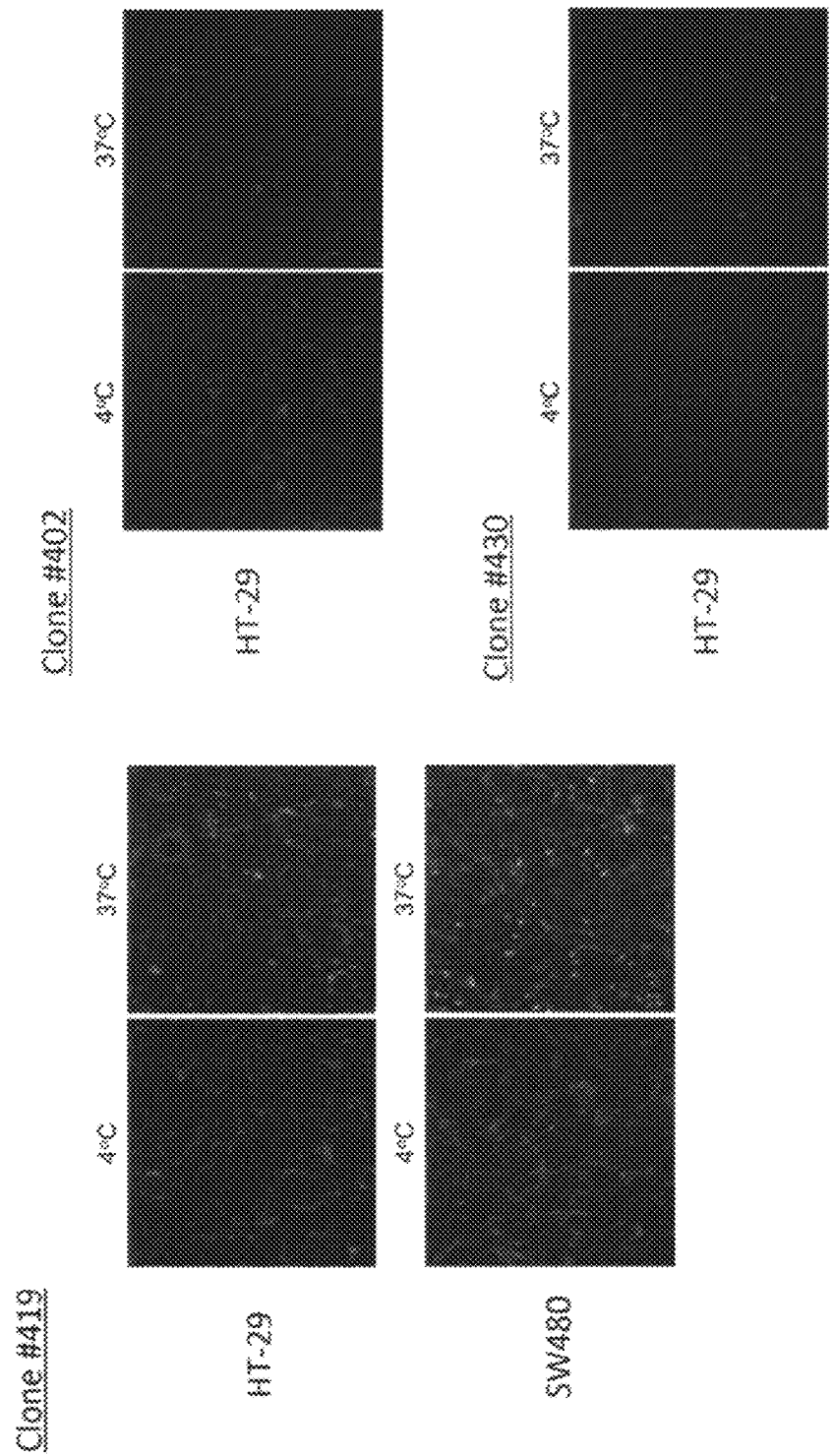

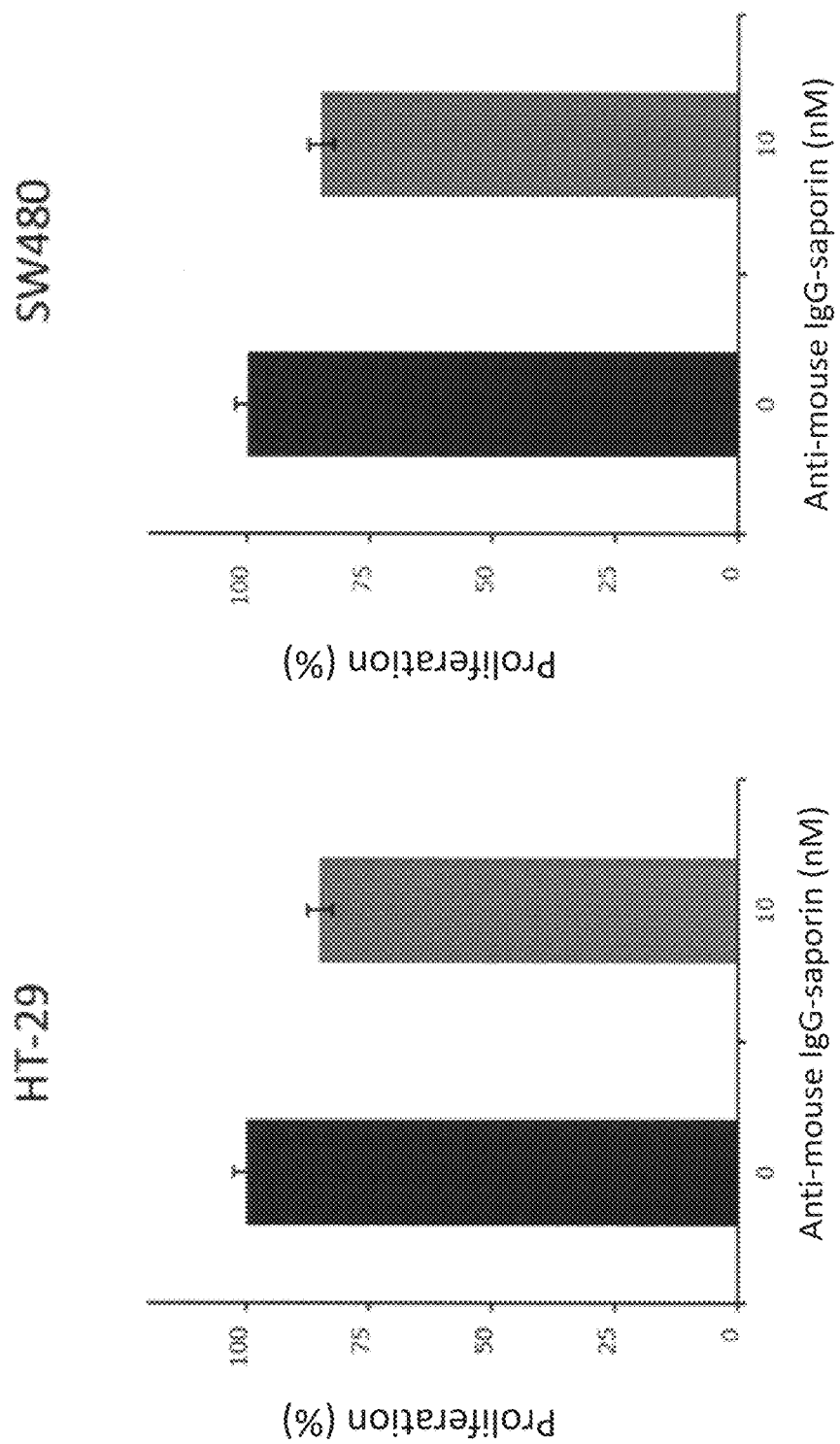

SEQUENCE LISTING

```
<160> NUMBER OF SEQ ID NOS: 42

<210> SEQ ID NO 1
<211> LENGTH: 6516
<212> TYPE: DNA
<213> ORGANISM: Homo sapiens

<400> SEQUENCE: 1
gagagctgcc tgctcagaca acagacacgc gaggtcagga agaagccgct tataaattac      60
cgcttccttc gcgccgccgc caacgccgag ccccgaggac cgcaagccca gaggacaagc     120
tgcgccaaga gggagtgcgg agcgttcacc cagcgggtca gagagcgagc gggcaggcag     180
cccccggccg gcggaacccg gcacagccga gcagagcgcg ggcggcgccg cagccacccc     240
agatccagaa ccagaaccac agcccttctg aggagctccc aaacaaagca aggagatggc     300
caccaaggag aagctgcagt gtctgaaaga tttccacaag gacatcctga agccctcacc     360
agggaagagc ccaggcacgc ggcctgagga cgaggctgag ggaaaacctc gcagaggga     420 gaagtggtct agcaagatcg actttgtgct ctctgtggct ggcggcttcg tgggcttggg     480
caacgtctgg cgcttcccgt acctctgcta caagaatggt ggaggtgcgt ttctcatacc     540
gtattttatt ttcctgtttg ggagcggcct gcctgtgttt tcttggaga tcatcatagg     600 ccagtacacc tctgaagggg gcatcacctg ctgggaaaag atctgcccct tgttctctgg     660
tatcggctat gcctccgttg taattgtgtc cctcctgaat gtctactaca tcgtcatcct     720
ggcctgggcc acatactacc tgttccagtc cttcagaag gagctgcct gggcacactg     780 caaccacagc tggaacacac ctcactgcat ggaggacacc atgcgcaaga caagagtgt     840 ctggatcacc atcagctcca ccaacttcac ctccctgtc atcgagttct gggagcgcaa     900
cgtgctgagc ttgtcccctg gaatcgacca cccaggctct ctgaaatggg acctcgctct    960
ctgccttctt ttagtctggc tagtgtgttt cttctgcatc tggaagggcg tcaggtccac    1020
tgggaaggtc gtcacttca cagccacttt tccattcgcc atgctcctgg tgctgctggt   1080
ccgagggctg acgctgccgg gcgcgggcgc aggcatcaag ttctatctgt atcctgacat   1140
```

```
cacccgcctt gaggacccac aggtgtggat tgacgctggg actcagatat tcttctctta    1200
tgccatctgc ctgggggcta tgacctcgct ggggagctac aacaagtaca agtataactc    1260
gtacagggac tgtatgctgc tgggatgcct gaacagtggt accagttttg tgtctggctt    1320 cgcaatttt tccatcctgg gcttcatggc acaagagcaa ggggtggaca ttgctgatgt    1380
ggctgagtca ggtcctggcc tggccttcat tgcctaccca aaagctgtga caatgatgcc    1440
gctgcccaca ttttggtcca ttcttttttt tattatgctt ctcttgcttg gactggatag    1500
ccagtttgtt gaagttgaag acagatcac atccttggtt gatctttacc catccttcct     1560
aaggaagggt tatcgtcggg aaatcttcat cgccttcgtg tgtagcatca gctacctgct    1620
ggggctgacg atggtgacgg agggtggcat gtatgtgttt cagctctttg actactatgc    1680
agctagcggt gtatgccttt tgtgggttgc attctttgaa tgttttgtta ttgcctggat    1740
atatggaggt gataaccttt atgatggtat tgaggacatg attggctatc ggcccgggcc    1800
ctggatgaag tacagctggg ctgtgatcac tccagttctc tgtgttggat gtttcatctt    1860
ctcgctcgtc aagtacgtac ccctgaccta caacaaaaca tacgtgtacc ccaactgggc    1920
cattgggctg gctggagcc tggccctttc ctccatgctc tgcgttccct tggtcatcgt     1980
catccgcctc tgccagactg aggggccgtt ccttgtgaga gtcaagtacc tgctgacccc    2040
aagggaaccc aaccgctggg ctgtggagcg cgagggagcc acaccttaca actctcgcac    2100
cgtcatgaac ggcgctctcg tgaaaccgac ccacatcatt gtggagacca tgatgtgagc    2160
tctctcgggt cgacggggcc ggcggctttc ctgctgttta ctaacattag attctcatag    2220
gaccaggttt acagagcttt atatttgcac taggatttt tttttttgt aattgtcaca     2280 gaaaatgtaa ttgtgggtat gtgtgcgtgc gtgtgtgtgt gtgtgtgtat cgtgtgtgtg    2340
tgttttgttt tgatttgggg gatattttgt acaaaaagaa aacccacggg aagatgtccg    2400
tggagaggca gagctttcat actgaattag atgtatttta tgggaatttg gtaaattttt    2460
ctttgtattt ttttttttac atataagtat atatacactt agagattgtc atatacttt     2520 accacttgaa ttgatcttct tgccagcaat agatctcatt ttcaaaagca attcttcggt    2580
gctgtgtagc tggcagaaag ttctgtccag taaacgcagg atggaatttt cctgggactc    2640
tacacccatc ttaaggtggt ataccttcca aatcctggtt cagatggaag aaatagcagg    2700
agagaggacc cattagctgg cagacccagg gggaagaaag gagggctgtg aggagatacc    2760
tcattaaact tggcttagtg aagaagagag atgccaaagg aatgaaccaa cccttcacat    2820
aaaggagact ggctgaagct gaatgaggag gccctatagc agaagtctga ttctaagagc    2880
agtagaaact tgtaccagaa gcaaaatccc acttttaatt ttgagatggt gagtggatag    2940
tcagtagacc gtcagaacca ctggccgaga agggagctgc tagagatcca agaaggctgg    3000
caggagtgag gctcacaact cagcctcgca agaggtggca gaggcacagg aggccacagt    3060
ccttcctggg gcattccagg cagagaagga gcagaggctc tcccggcagg agctggggtc    3120
tcagggctca gatgagtctg ttgcatttga atggggtcat agcaggttct ggtcattccc    3180
caagcaacat ctcagcatct cttaaagttg cctgcaggaa tgaagcatga catacctgtt    3240
gagggactag gggagtggtg gggaggtgag tggaccaaag gatataggcc ccaggcatgc    3300
agatgggccc ggtgtcgggg aggggtgctt tctttcctca tctccccact ccccactctc    3360
agcctgggag actcctgcca agccctcatt aaagatgcca ccctgggctg ccctggcacc    3420
tagcaaggca caccaagaac agcttttgag tctgtatcct ccactggggg aagtgctccc    3480
agttcagaac aagggcagcc cgtggtgctg acctaggata taacaaagct cttcacttca    3540
```

-continued

```
aaaccccctgc aatagctggg tttacagaca tttaccacct gcggacccaa aagagaaggc    3600
ctaggagagt tttctagaag gttgggattg tcagggtcct ggcccctcag aactggcttg    3660
atcaagggcc ttatgtggag cagaggttgt ctctgaacca ggagagaagg tactatacct    3720
ttcaaatccc cagggcagac acaccccccac ccagccccta tttggaccta aactgtgcca    3780
tttgaacagt cacttccaag ctcagtctaa atgaaaccga aacgtgacca cgcacaaagg    3840
cagtcactgc ctcgaggggt gcagaccgca gaattttcac agcaggggct cttggaaccc    3900
tggaaacccc cttcttaaat tgggaggag gagtatgcct ttggtgtccc cctcccaagg     3960
ggcaattctg aacccatct ttggcaggca tacatatttc actgtttcca aagctatcta    4020
ctctgccaaa caacacccag tcctattcca aactctcaac gattctatct tgttcctgtt    4080
tttctatgta tttatggttg ccgttttgtgt ctgatttgat tttactgttt tttccctgat    4140
tttatggagt agcattgtga cctgttttcc tttgtcttat ataactttag taaactaacc    4200
actgtcaatg attgagggca ggtggcacgt ggggaagagg ggacttggca cgcagtggct    4260
acctgggcat ttgtggtcat ttcagttttcc atctccccag cgggggctcc ctgggtgaaa    4320
ggccacagta ttttggggttg gtaggcaaat tgcaacattc tggacatggc ctgaggaagg    4380
cctcttctta taagattctc agaccaaatt ctagaccaaa gacacaggca gaccaagtcc    4440
ccaggcccccg cctggaagga agtcgttcct caactctccc caaggcacct gtctccaatc    4500
agagccctct cgcccagcca gccctggctc tgtgtgcaga gcatagctct gcgagtacct    4560
gtgtaataat gctcaacctt catgtctccg tataaacgaa actttccatg agagctcatg    4620
actctggtcc acctgtctat agagaatggg caaagtcctt cacctgcttt ctgcttggga    4680
tgggtcagaa atgctgatgc ccgcacatag cccagccagc cagatctgga aaggaagcga    4740
gggggttgtt taaatcaatt ttttaagatg aagaagtggg agacactgcg ttgagatggg    4800
ccatgctagg gccacagaga tttcctgacg gtcagggaga aagggcctc cagggtccccc    4860
taacccaacg cccttgttgt aaatgaggta actgaggctc agggaggcac tgtgagccag    4920
gaatggattt tcttgaaaca gctctagctg caggttctcc gaggtaggtg cagggaatgg    4980
tgagtgtcta accagggcta catccagcaa catcctcaag gtcttcctga caaccaaaga    5040
caagcctta tggaaaagga aatgcgctcc cctccatgtt cagggatgag gggagcagca    5100
gcagccacac tcccaccatc ctcacagaat tcctggaccc atgcggtggc tccgtgagct    5160
gggtgactcc agcctcacct gcacacccca gccctgcacg gggccctcct tcctcccagc    5220
agcccttggt gagctaggaa ttgagatccc tgtttgtgaa agagggaact gaggtgcaga    5280
gaagccagag gtgtgccaga tccttaggca ggatttagat gaagtcgccc tggctccaga    5340
ctgaccccga ggctctgcgg ggagtttcca ggcagcagga agtggccttg gatgctctcc    5400
ttccaggaca gcataacccc tgggccatgt gcagctcctt cactgccccc tggatcccca    5460
gcataccccc aaagacagtg gggaaacaca aggggagagc acagcatggc ccctccagcc    5520
cacttcaggg cactcttgta tcacccgggt accgccacac tggtcccccca cccagccagc    5580
atctcccagc acagcccctc tccctgggga atgctctgg gtagccagtc taaaggcaga    5640
ggcacctaac tgctccccgc agcccacccc acccaagatt cagacacaag ccaggaaagg    5700
acccaagaga aaatccttca aggtggcctg aggtcccatc cctccctcag acccatgtgg    5760
tcccaggcca ggctgcctgg gacacggtaa ataccactgt gtgcaaaaat cgaagtacaa    5820
aaccacaaga ctaaacaaaa caaacccaga gagccaaact tgtagaggtg ggcagtccag    5880
aaagcagggg gcagccctcc ccctttcctt ctctccctga tcctcagaat atatattgtt    5940
```

-continued

```
gtaataggaa gcattttgc attgttctct tgtgggtgtc actacagaca tgttctggcg    6000
tgttctccga gggatggagc atcctgttat atatttgact tcaaattgag atgttggctt    6060 cattttttt ttttacccaa ttaatctccc aatccctagc aactgtgact ctgtatttag    6120
cacaagagaa agctgagaat gtgggtcttg cctccttcca gaaatatgtc tggctcatca    6180 ggacatttt ttaaaacttc aaaatatttt taagatattt taaactttta taaaaaaaa    6240 atcaaccaac aagagacttt tctgaggagg aacatttgta tttgaacaag atccttggtg    6300
tgtagttcag tcttgcagta tacaagcttt tgtgtataaa tgttttatga tatgattccc    6360
tgtattttgc aggggttttt ttctcttttg cttttagat aaatatgtat atcaatattt    6420
taaattcatc tttgctttt ttagaggagt ttgtaatcac cttataacat gaaaataaac    6480 atttccttt taacatccaa aaaaaaaaa aaaaaa                                6516
```

<210> SEQ ID NO 2
<211> LENGTH: 620
<212> TYPE: PRT
<213> ORGANISM: Homo sapiens

<400> SEQUENCE: 2

```
Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
            20                  25                  30

Glu Ala Glu Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Ile Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Val
        115                 120                 125

Val Ile Val Ser Leu Leu Asn Val Tyr Tyr Ile Val Ile Leu Ala Trp
    130                 135                 140

Ala Thr Tyr Tyr Leu Phe Gln Ser Phe Gln Lys Glu Leu Pro Trp Ala
145                 150                 155                 160

His Cys Asn His Ser Trp Asn Thr Pro His Cys Met Glu Asp Thr Met
                165                 170                 175

Arg Lys Asn Lys Ser Val Trp Ile Thr Ile Ser Ser Thr Asn Phe Thr
            180                 185                 190

Ser Pro Val Ile Glu Phe Trp Glu Arg Asn Val Leu Ser Leu Ser Pro
        195                 200                 205

Gly Ile Asp His Pro Gly Ser Leu Lys Trp Asp Leu Ala Leu Cys Leu
    210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Ala
            260                 265                 270
```

Gly Ile Lys Phe Tyr Leu Tyr Pro Asp Ile Thr Arg Leu Glu Asp Pro
            275                 280                 285

Gln Val Trp Ile Asp Ala Gly Thr Gln Ile Phe Phe Ser Tyr Ala Ile
        290                 295                 300

Cys Leu Gly Ala Met Thr Ser Leu Gly Ser Tyr Asn Lys Tyr Lys Tyr
305                 310                 315                 320

Asn Ser Tyr Arg Asp Cys Met Leu Leu Gly Cys Leu Asn Ser Gly Thr
                325                 330                 335

Ser Phe Val Ser Gly Phe Ala Ile Phe Ser Ile Leu Gly Phe Met Ala
            340                 345                 350

Gln Glu Gln Gly Val Asp Ile Ala Asp Val Ala Glu Ser Gly Pro Gly
        355                 360                 365

Leu Ala Phe Ile Ala Tyr Pro Lys Ala Val Thr Met Met Pro Leu Pro
370                 375                 380

Thr Phe Trp Ser Ile Leu Phe Phe Ile Met Leu Leu Leu Leu Gly Leu
385                 390                 395                 400

Asp Ser Gln Phe Val Glu Val Glu Gly Gln Ile Thr Ser Leu Val Asp
                405                 410                 415

Leu Tyr Pro Ser Phe Leu Arg Lys Gly Tyr Arg Arg Glu Ile Phe Ile
            420                 425                 430

Ala Phe Val Cys Ser Ile Ser Tyr Leu Leu Gly Leu Thr Met Val Thr
        435                 440                 445

Glu Gly Gly Met Tyr Val Phe Gln Leu Phe Asp Tyr Tyr Ala Ala Ser
450                 455                 460

Gly Val Cys Leu Leu Trp Val Ala Phe Phe Glu Cys Phe Val Ile Ala
465                 470                 475                 480

Trp Ile Tyr Gly Gly Asp Asn Leu Tyr Asp Gly Ile Glu Asp Met Ile
                485                 490                 495

Gly Tyr Arg Pro Gly Pro Trp Met Lys Tyr Ser Trp Ala Val Ile Thr
            500                 505                 510

Pro Val Leu Cys Val Gly Cys Phe Ile Phe Ser Leu Val Lys Tyr Val
        515                 520                 525

Pro Leu Thr Tyr Asn Lys Thr Tyr Val Tyr Pro Asn Trp Ala Ile Gly
530                 535                 540

Leu Gly Trp Ser Leu Ala Leu Ser Ser Met Leu Cys Val Pro Leu Val
545                 550                 555                 560

Ile Val Ile Arg Leu Cys Gln Thr Glu Gly Pro Phe Leu Val Arg Val
                565                 570                 575

Lys Tyr Leu Leu Thr Pro Arg Glu Pro Asn Arg Trp Ala Val Glu Arg
            580                 585                 590

Glu Gly Ala Thr Pro Tyr Asn Ser Arg Thr Val Met Asn Gly Ala Leu
        595                 600                 605

Val Lys Pro Thr His Ile Ile Val Glu Thr Met Met
610                 615                 620

<210> SEQ ID NO 3
<211> LENGTH: 222
<212> TYPE: DNA
<213> ORGANISM: Homo sapiens

<400> SEQUENCE: 3
gcctgggcca catactacct gttccagtcc ttccagaagg agctgccctg ggcacactgc      60
aaccacagct ggaacacacc tcactgcatg gaggacacca tgcgcaagaa caagagtgtc     120

```
tggatcacca tcagctccac caacttcacc tccctgtca tcgagttctg ggagcgcaac    180
gtgctgagct tgtccctgg aatcgaccac ccaggctctc tg                      222
```

<210> SEQ ID NO 4
<211> LENGTH: 74
<212> TYPE: PRT
<213> ORGANISM: Homo sapiens

<400> SEQUENCE: 4

```
Ala Trp Ala Thr Tyr Tyr Leu Phe Gln Ser Phe Gln Lys Glu Leu Pro
1               5                   10                  15

Trp Ala His Cys Asn His Ser Trp Asn Thr Pro His Cys Met Glu Asp
            20                  25                  30

Thr Met Arg Lys Asn Lys Ser Val Trp Ile Thr Ile Ser Ser Thr Asn
        35                  40                  45

Phe Thr Ser Pro Val Ile Glu Phe Trp Glu Arg Asn Val Leu Ser Leu
    50                  55                  60

Ser Pro Gly Ile Asp His Pro Gly Ser Leu
65                  70
```

<210> SEQ ID NO 5
<211> LENGTH: 31
<212> TYPE: DNA
<213> ORGANISM: Artificial
<220> FEATURE:
<223> OTHER INFORMATION: Synthetic DNA

<400> SEQUENCE: 5

```
ataggatccg gcctgggcca catactacct g                                  31
```

<210> SEQ ID NO 6
<211> LENGTH: 32
<212> TYPE: DNA
<213> ORGANISM: Artificial
<220> FEATURE:
<223> OTHER INFORMATION: Synthetic DNA

<400> SEQUENCE: 6

```
tatgaattcg ctttcagaga gcctgggtgg tc                                 32
```

<210> SEQ ID NO 7
<211> LENGTH: 45
<212> TYPE: DNA
<213> ORGANISM: Artificial
<220> FEATURE:
<223> OTHER INFORMATION: Synthetic DNA

<400> SEQUENCE: 7

```
ctaatacgac tcactatagg gcaagcagtg gtatcaacgc agagt                   45
```

<210> SEQ ID NO 8
<211> LENGTH: 22
<212> TYPE: DNA
<213> ORGANISM: Artificial
<220> FEATURE:
<223> OTHER INFORMATION: Synthetic DNA

<400> SEQUENCE: 8

```
ctaatacgac tcactatagg gc                                            22
```

<210> SEQ ID NO 9
<211> LENGTH: 34
<212> TYPE: DNA
<213> ORGANISM: Artificial
<220> FEATURE:
<223> OTHER INFORMATION: Synthetic DNA

<400> SEQUENCE: 9 ccagggggcca gtggatagac cgatggggct gttg                              34

<210> SEQ ID NO 10
<211> LENGTH: 26
<212> TYPE: DNA
<213> ORGANISM: Artificial
<220> FEATURE:
<223> OTHER INFORMATION: Synthetic DNA

<400> SEQUENCE: 10
gcacctccag atgttaactg ctcact                                        26

<210> SEQ ID NO 11
<211> LENGTH: 993
<212> TYPE: DNA
<213> ORGANISM: Artificial
<220> FEATURE:
<223> OTHER INFORMATION: Synthetic DNA

<400> SEQUENCE: 11
gctagcacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tga                               993

<210> SEQ ID NO 12
<211> LENGTH: 29
<212> TYPE: DNA
<213> ORGANISM: Artificial
<220> FEATURE:
<223> OTHER INFORMATION: Synthetic DNA

<400> SEQUENCE: 12
tttgaattcg ctagcaccaa gggcccatc                                     29

```
<210> SEQ ID NO 13
<211> LENGTH: 35
<212> TYPE: DNA
<213> ORGANISM: Artificial
<220> FEATURE:
<223> OTHER INFORMATION: Synthetic DNA

<400> SEQUENCE: 13
tttgcggccg ctcatttacc cggagacagg gagag                              35

<210> SEQ ID NO 14
<211> LENGTH: 50
<212> TYPE: DNA
<213> ORGANISM: Artificial
<220> FEATURE:
<223> OTHER INFORMATION: Synthetic DNA

<400> SEQUENCE: 14
catgggttgg agcctcatct tgctcttcct tgtcgctgtt gctacgcgtg              50

<210> SEQ ID NO 15
<211> LENGTH: 59
<212> TYPE: DNA
<213> ORGANISM: Artificial
<220> FEATURE:
<223> OTHER INFORMATION: Synthetic DNA

<400> SEQUENCE: 15
ggatccacgc gtagcaacag cgacaaggaa gagcaagatg aggctccaac ccatggtac    59

<210> SEQ ID NO 16
<211> LENGTH: 38
<212> TYPE: DNA
<213> ORGANISM: Artificial
<220> FEATURE:
<223> OTHER INFORMATION: Synthetic DNA

<400> SEQUENCE: 16
tttacgcgtg tcctgtccca ggtccagctg cagcagtc                           38

<210> SEQ ID NO 17
<211> LENGTH: 34
<212> TYPE: DNA
<213> ORGANISM: Artificial
<220> FEATURE:
<223> OTHER INFORMATION: Synthetic DNA

<400> SEQUENCE: 17
tttgctagct gcagagacag tgaccagagt ccct                               34

<210> SEQ ID NO 18
<211> LENGTH: 343
<212> TYPE: DNA
<213> ORGANISM: Artificial
<220> FEATURE:
<223> OTHER INFORMATION: Synthetic DNA

<400> SEQUENCE: 18
caccaagctg gaaatcaaac gtacggtggc tgcaccatct gtcttcatct tcccgccatc   60
tgatgagcag ttgaaatctg gaactgcctc tgttgtgtgc ctgctgaata acttctatcc  120
cagagaggcc aaagtacagt ggaaggtgga taacgccctc caatcgggta actcccagga  180
gagtgtcaca gagcaggaca gcaaggacag cacctacagc ctcagcagca ccctgacgct  240
```

| | |
|---|---|
| gagcaaagca gactacgaga aacacaaagt ctacgcctgc gaagtcaccc atcagggcct | 300 |
| gagctcgccc gtcacaaaga gcttcaacag gggagagtgt tag | 343 |

<210> SEQ ID NO 19
<211> LENGTH: 29
<212> TYPE: DNA
<213> ORGANISM: Artificial
<220> FEATURE:
<223> OTHER INFORMATION: Synthetic DNA

<400> SEQUENCE: 19

| | |
|---|---|
| tttgaattcc gtacggtggc tgcaccatc | 29 |

<210> SEQ ID NO 20
<211> LENGTH: 30
<212> TYPE: DNA
<213> ORGANISM: Artificial
<220> FEATURE:
<223> OTHER INFORMATION: Synthetic DNA

<400> SEQUENCE: 20

| | |
|---|---|
| tttgcggccg cctaacactc tcccctgttg | 30 |

<210> SEQ ID NO 21
<211> LENGTH: 31
<212> TYPE: DNA
<213> ORGANISM: Artificial
<220> FEATURE:
<223> OTHER INFORMATION: Synthetic DNA

<400> SEQUENCE: 21

| | |
|---|---|
| tttggatcca ccatgaacat gctcactcag c | 31 |

<210> SEQ ID NO 22
<211> LENGTH: 28
<212> TYPE: DNA
<213> ORGANISM: Artificial
<220> FEATURE:
<223> OTHER INFORMATION: Synthetic DNA

<400> SEQUENCE: 22

| | |
|---|---|
| tttcgtacgt ttgatttcca gcttggtg | 28 |

<210> SEQ ID NO 23
<211> LENGTH: 1398
<212> TYPE: DNA
<213> ORGANISM: Artificial
<220> FEATURE:
<223> OTHER INFORMATION: Synthetic DNA

<400> SEQUENCE: 23

| | |
|---|---|
| atgggttgga gcctcatctt gctcttcctt gtcgctgttg ctacgcgtgt cctgtcccag | 60 |
| gtcaaactgc agcagtctgg acctgagctg gtaaagcctg gggcttcagt gaagatgtcc | 120 |
| tgcaaggctt ctggatacac attcactagc tatgttatgc actgggtgaa gcagaagcct | 180 |
| gggcagggcc ttgagtggat tggatatatt aatccttaca atgatggtac taagtacaat | 240 |
| gagaagttca aggcaaggc cacactgact tcagacaaat cctccagcac agcctacatg | 300 |
| gagctcagca gcctgacctc tgaggactct gcggtctatt actgtgcaag gaggaaggcc | 360 |
| tggtttgctt actggggcca agggactctg gtcactgtct ctgcagctag caccaagggc | 420 |
| ccatcggtct tccccctggc accctcctcc aagagcacct ctgggggcac agcggccctg | 480 |
| ggctgcctgg tcaaggacta cttccccgaa ccggtgacgg tgtcgtggaa ctcaggcgcc | 540 |

```
ctgaccagcg gcgtgcacac cttcccggct gtcctacagt cctcaggact ctactccctc    600
agcagcgtgg tgaccgtgcc ctccagcagc ttgggcaccc agacctacat ctgcaacgtg    660
aatcacaagc ccagcaacac caaggtggac aagaaagttg agcccaaatc ttgtgacaaa    720
actcacacat gcccaccgtg cccagcacct gaactcctgg ggggaccgtc agtcttcctc    780
ttccccccaa aacccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caagggcag   1080 ccccgagaac cacaggtgta cacctgcccc catcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaatga                                                  1398
```

<210> SEQ ID NO 24
<211> LENGTH: 465
<212> TYPE: PRT
<213> ORGANISM: Artificial
<220> FEATURE:
<223> OTHER INFORMATION: Synthetic DNA

<400> SEQUENCE: 24

```
Met Gly Trp Ser Leu Ile Leu Leu Phe Leu Val Ala Val Ala Thr Arg
1               5                   10                  15

Val Leu Ser Gln Val Lys Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Arg Lys Ala Trp Phe Ala Tyr Trp Gly Gln Gly
        115                 120                 125

Thr Leu Val Thr Val Ser Ala Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205
```

```
Ser Ser Leu Gly Thr Gln Thr Tyr Ile Cys Asn Val Asn His Lys Pro
    210                 215                 220
Ser Asn Thr Lys Val Asp Lys Val Glu Pro Lys Ser Cys Asp Lys
225                 230                 235                 240
Thr His Thr Cys Pro Pro Cys Pro Ala Pro Glu Leu Leu Gly Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
        275                 280                 285
Pro Glu Val Lys Phe Asn Trp Tyr Val Asp Gly Val Glu Val His Asn
    290                 295                 300
Ala Lys Thr Lys Pro Arg Glu Glu Gln Tyr Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Ala Leu Pro Ala Pro Ile Glu Lys
            340                 345                 350
Thr Ile Ser Lys Ala Lys Gly Gln Pro Arg Glu Pro Gln Val Tyr Thr
        355                 360                 365
Leu Pro Pro Ser Arg Asp Glu Leu Thr Lys Asn Gln Val Ser Leu Thr
    370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
        435                 440                 445
Ala Leu His Asn His Tyr Thr Gln Lys Ser Leu Ser Leu Ser Pro Gly
    450                 455                 460
Lys
465

<210> SEQ ID NO 25
<211> LENGTH: 705
<212> TYPE: DNA
<213> ORGANISM: Artificial
<220> FEATURE:
<223> OTHER INFORMATION: Synthetic DNA

<400> SEQUENCE: 25
atgaacatgc tcactcagct cctgggatta ctgctgctct ggtttgcagg tggtaaatgt      60
gacattcaga tgacccagtc tcctgcctcc cagtctgcat ctctgggaga aagtgtcacc    120
atcacatgcc tggcaagtca gaccattggt acatggttag catggtatca gcagaaacca    180
gggaaatctc ctcagctcct gatttatgct gcaaccagct ggcagatggg gtcccatca     240 aggttcagtg gtagtggatc tggcacaaaa ttttctttca agatcagcag cctacaggct    300
gaagattttg taagttatta ctgtcaacaa ctttacagta ctcctctgac gttcggtgga    360
ggcaccaagc tggaaatcaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
```

```
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                    705
```

<210> SEQ ID NO 26
<211> LENGTH: 234
<212> TYPE: PRT
<213> ORGANISM: Artificial
<220> FEATURE:
<223> OTHER INFORMATION: Synthetic DNA

<400> SEQUENCE: 26

```
Met Asn Met Leu Thr Gln Leu Leu Gly Leu Leu Leu Leu Trp Phe Ala
1               5                   10                  15

Gly Gly Lys Cys Asp Ile Gln Met Thr Gln Ser Pro Ala Ser Gln Ser
            20                  25                  30

Ala Ser Leu Gly Glu Ser Val Thr Ile Thr Cys Leu Ala Ser Gln Thr
        35                  40                  45

Ile Gly Thr Trp Leu Ala Trp Tyr Gln Gln Lys Pro Gly Lys Ser Pro
    50                  55                  60

Gln Leu Leu Ile Tyr Ala Ala Thr Ser Leu Ala Asp Gly Val Pro Ser
65                  70                  75                  80

Arg Phe Ser Gly Ser Gly Ser Gly Thr Lys Phe Ser Phe Lys Ile Ser
                85                  90                  95

Ser Leu Gln Ala Glu Asp Phe Val Ser Tyr Tyr Cys Gln Gln Leu Tyr
            100                 105                 110

Ser Thr Pro Leu Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 27
<211> LENGTH: 1401
<212> TYPE: DNA
<213> ORGANISM: Artificial
<220> FEATURE:
<223> OTHER INFORMATION: Synthetic DNA

<400> SEQUENCE: 27

```
atgggttgga gcctcatctt gctcttcctt gtcgctgttg ctacgcgtgt cctgtcccag    60
gtcaaactgc agcagtctgg acctgagctg gtgaagcctg ggcttcagt gaaagtatcc    120 tgcacggctt ctggttatgc attcactcaa tacaacttgt actgggtgaa gctcagacat    180
ggaaagtgcc ctaaatggat cggatctatt gatccttaca ttggtggtac cacctacaac    240
```

```
cagcaattca aggacaaggt cacattgact gttgacaagt cttccagcac ggcctacttg    300
catctcaaca gcctgacatc tgaagactct gcaatctatt actgtgcaag atggtgggac    360
ggatatttcg atgtctgggg cgcagggacc acggtcaccg tctcctcagc tagcaccaag    420
ggcccatcgg tcttcccect ggcacccetcc tccaagagca cctctggggg cacagcggec    480 ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagaaag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggatgagct gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct tcctctacag caagctcacc gtggacaaga gcaggtggca gcagggggaac   1320 gtcttctcat gctccgtgat gcatgaggct ctgcacaacc actacacgca gaagagcctc   1380
tccctgtctc cgggtaaatg a                                             1401
```

<210> SEQ ID NO 28
<211> LENGTH: 466
<212> TYPE: PRT
<213> ORGANISM: Artificial
<220> FEATURE:
<223> OTHER INFORMATION: Synthetic DNA

<400> SEQUENCE: 28

```
Met Gly Trp Ser Leu Ile Leu Leu Phe Leu Val Ala Val Ala Thr Arg
1               5                   10                  15

Val Leu Ser Gln Val Lys Leu Gln Gln Ser Gly Pro Glu Leu Val Lys
            20                  25                  30

Pro Gly Ala Ser Val Lys Val Ser Cys Thr Ala Ser Gly Tyr Ala Phe
        35                  40                  45

Thr Gln Tyr Asn Leu Tyr Trp Val Lys Leu Arg His Gly Lys Cys Pro
    50                  55                  60

Lys Trp Ile Gly Ser Ile Asp Pro Tyr Ile Gly Thr Thr Tyr Asn
65                  70                  75                  80

Gln Gln Phe Lys Asp Lys Val Thr Leu Thr Val Asp Lys Ser Ser Ser
                85                  90                  95

Thr Ala Tyr Leu His Leu Asn Ser Leu Thr Ser Glu Asp Ser Ala Ile
            100                 105                 110

Tyr Tyr Cys Ala Arg Trp Trp Asp Gly Tyr Phe Asp Val Trp Gly Ala
        115                 120                 125

Gly Thr Thr Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160
```

```
Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
        180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 29
<211> LENGTH: 714
<212> TYPE: DNA
<213> ORGANISM: Artificial
<220> FEATURE:
<223> OTHER INFORMATION: Synthetic DNA

<400> SEQUENCE: 29
atggattttc aggtgcagat tttcagcttc ctgctaatca gtgcctcagt catttgtcc      60 agaggacaga ttgttctcac ccagtctcca gcaatcatgt ctgcttctct aggggaacgg     120
gtcaccttga cctgcactgc cagctcaagt gtaatttcca gatacttgca ctggtaccag     180
gtgaagccag atcctccccc aaactctgg atttatagca catccaacct ggcttctgga     240
gtcccaactc gcttcagtgg cagtgggtct gggacctctt actctctcac aatcagtaac     300
```

```
atggaggctg aagatgctgc cacttattac tgccaccagt atcatcgttc cccgctcacg    360
ttcggtgctg ggaccaagct ggagctgaca cgtacggtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttag          714
```

<210> SEQ ID NO 30
<211> LENGTH: 237
<212> TYPE: PRT
<213> ORGANISM: Artificial
<220> FEATURE:
<223> OTHER INFORMATION: Synthetic DNA

<400> SEQUENCE: 30

Met Asp Phe Gln Val Gln Ile Phe Ser Phe Leu Leu Ile Ser Ala Ser
1               5                   10                  15

Val Ile Leu Ser Arg Gly Gln Ile Val Leu Thr Gln Ser Pro Ala Ile
            20                  25                  30

Met Ser Ala Ser Leu Gly Glu Arg Val Thr Leu Thr Cys Thr Ala Ser
        35                  40                  45

Ser Ser Val Ile Ser Arg Tyr Leu His Trp Tyr Gln Val Lys Pro Gly
    50                  55                  60

Ser Ser Pro Lys Leu Trp Ile Tyr Ser Thr Ser Asn Leu Ala Ser Gly
65                  70                  75                  80

Val Pro Thr Arg Phe Ser Gly Ser Gly Ser Gly Thr Ser Tyr Ser Leu
                85                  90                  95

Thr Ile Ser Asn Met Glu Ala Glu Asp Ala Ala Thr Tyr Tyr Cys His
            100                 105                 110

Gln Tyr His Arg Ser Pro Leu Thr Phe Gly Ala Gly Thr Lys Leu Glu
        115                 120                 125

Leu Thr Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 31
<211> LENGTH: 1407
<212> TYPE: DNA
<213> ORGANISM: Artificial
<220> FEATURE:
<223> OTHER INFORMATION: Synthetic DNA

<400> SEQUENCE: 31

```
atgggttgga gcctcatctt gctcttcctt gtcgctgttg ctacgcgtgt cctgtcccag      60
atccagctgc agcagtctgg acctgagctg gtgaagcctg ggcttcagt gaaagtctcc     120
tgcaaggctt ttggttatgc attcactaga cacaatatgt actgggtgaa gcagaggcat     180
ggaaagtgcc ttgagtggat tggatatatt gatcctttca atggtggtac tagctacaac     240
cagaagttca gggcaaggc cacattgact gttgacaagt cctccagcac agcctacatg     300
catctcaaca gcctgacatc tgaggactct gcagtctatt actgtgcaag agtttatggt     360
aactacgcct ggtttgctta ctggggccaa gggactctgg tcactgtctc tgcagctagc     420
accaagggcc catcggtctt ccccctggca ccctcctcca gagcacctc tggggggcaca     480
gcggccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct gggcaccca gacctacatc     660
tgcaacgtga atcacaagcc cagcaacacc aaggtggaca gaaagttga gcccaaatct     720
tgtgacaaaa ctcacacatg cccaccgtgc ccagcacctg aactcctggg gggaccgtca     780
gtcttcctct tccccccaaa acccaaggac accctcatga tctcccggac ccctgaggtc     840
acatgcgtgg tggtggacgt gagccacgaa gaccctgagg tcaagttcaa ctggtacgtg     900
gacggcgtgg aggtgcataa tgccaagaca aagccgcggg aggagcagta caacagcacg     960
taccgtgtgg tcagcgtcct caccgtcctg caccaggact ggctgaatgg caaggagtac    1020
aagtgcaagg tctccaacaa agccctccca gcccccatcg agaaaaccat ctccaaagcc    1080
aaagggcagc cccgagaacc acaggtgtac accctgcccc catcccggga tgagctgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaatga                                         1407
```

<210> SEQ ID NO 32
<211> LENGTH: 468
<212> TYPE: PRT
<213> ORGANISM: Artificial
<220> FEATURE:
<223> OTHER INFORMATION: Synthetic DNA

<400> SEQUENCE: 32

```
Met Gly Trp Ser Leu Ile Leu Leu Phe Leu Val Ala Val Ala Thr Arg
1               5                   10                  15

Val Leu Ser Gln Ile Gln Leu Gln Gln Ser Gly Pro Glu Leu Val Lys
            20                  25                  30

Pro Gly Ala Ser Val Lys Val Ser Cys Lys Ala Phe Gly Tyr Ala Phe
        35                  40                  45

Thr Arg His Asn Met Tyr Trp Val Lys Gln Arg His Gly Lys Cys Leu
    50                  55                  60

Glu Trp Ile Gly Tyr Ile Asp Pro Phe Asn Gly Gly Thr Ser Tyr Asn
65                  70                  75                  80

Gln Lys Phe Lys Gly Lys Ala Thr Leu Thr Val Asp Lys Ser Ser Ser
                85                  90                  95
```

Thr Ala Tyr Met His Leu Asn Ser Leu Thr Ser Glu Asp Ser Ala Val
            100                 105                 110

Tyr Tyr Cys Ala Arg Val Tyr Gly Asn Tyr Ala Trp Phe Ala Tyr Trp
        115                 120                 125

Gly Gln Gly Thr Leu Val Thr Val Ser Ala Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 33
<211> LENGTH: 717
<212> TYPE: DNA
<213> ORGANISM: Artificial
<220> FEATURE:
<223> OTHER INFORMATION: Synthetic DNA

<400> SEQUENCE: 33

```
atgggcatca aaatggagtc acagattcag gtctttgtat tcgtgtttct ctggttgtct      60
ggtgttgacg gagacattgt gatgacccag tctcacaaat tcatgtccac atcagtagga     120
gacagggtca gcatcacctg caaggccagt caggatgtga gtactgctgt agcctggtat     180
caacagatac caggacaatc tcctaaacta ctgatttact cgtcatccta ccggtacact     240
ggagtccctg atcgcttcac tggcagtgga tctgggacgg atttcacttt caccatcagc     300
agtgtgcagg ctgaagacct ggcagtttat tactgtcagc aacattataa tactccgtgg     360
acgttcggtg gaggcaccaa gctggaaatc aaacgtacgg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc     660
acccatcagg gcctgagctc gcccgtcaca aagagcttca caggggaga gtgttag        717
```

<210> SEQ ID NO 34
<211> LENGTH: 238
<212> TYPE: PRT
<213> ORGANISM: Artificial
<220> FEATURE:
<223> OTHER INFORMATION: Synthetic DNA

<400> SEQUENCE: 34

```
Met Gly Ile Lys Met Glu Ser Gln Ile Gln Val Phe Val Phe Val Phe
1               5                   10                  15

Leu Trp Leu Ser Gly Val Asp Gly Asp Ile Val Met Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Ser Thr Ala Val Ala Trp Tyr Gln Gln Ile Pro
    50                  55                  60

Gly Gln Ser Pro Lys Leu Leu Ile Tyr Ser Ser Ser Tyr Arg Tyr Thr
65                  70                  75                  80

Gly Val Pro Asp Arg Phe Thr Gly Ser Gly Ser Gly Thr Asp Phe Thr
                85                  90                  95

Phe Thr Ile Ser Ser Val Gln Ala Glu Asp Leu Ala Val Tyr Tyr Cys
            100                 105                 110

Gln Gln His Tyr Asn Thr Pro Trp Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205
```

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 35
<211> LENGTH: 1416
<212> TYPE: DNA
<213> ORGANISM: Artificial
<220> FEATURE:
<223> OTHER INFORMATION: Synthetic DNA

<400> SEQUENCE: 35
atgggttgga gcctcatctt gctcttcctt gtcgctgttg ctacgcgtgt cctgtcccag     60
gtccaactgc agcagcctgg ggctgagttt gtgaagcctg ggacttcagt gaagctgtcc    120
tgcaaggctt ctggctacaa cttcaccagg tactggataa actgggtgaa gctgaggcct    180
ggacaaggcc ttgagtggat tggaaatatt tatcctgcta ctaatggtat taactacaat    240
gagaagttca gagcaaggc cacactgact gtggacacat tctccagcac agcctacatg    300
caactcagca gtctggcatc tgaggactct ggtctctatt actgtgcaag atgtaaaacg    360
atgttgtcac gatgtgcctg gtttccttac tggggccaag ggactctggt cactgtctcc    420
gcagctagca ccaagggccc atcggtcttc ccctggcac cctcctccaa gagcacctct    480
gggggcacag cggccctggg ctgcctggtc aaggactact ccccgaacc ggtgacggtg    540 tcgtggaact caggcgccct gaccagcggc gtgcacacct tcccggctgt cctacagtcc    600
tcaggactct actccctcag cagcgtggtg accgtgccct ccagcagctt gggcacccag    660
acctacatct gcaacgtgaa tcacaagccc agcaacacca aggtggacaa gaaagttgag    720
cccaaatctt gtgacaaaac tcacacatgc ccaccgtgcc cagcacctga actcctgggg    780
ggaccgtcag tcttcctctt ccccccaaaa cccaaggaca cctcatgat ctcccggacc    840 cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgtgtggt cagcgtcctc accgtcctgc accaggactg gctgaatggc   1020
aaggagtaca agtgcaaggt ctccaacaaa gccctcccag cccccatcga gaaaaccatc   1080
tccaaagcca agggcagcc ccgagaacca caggtgtaca ccctgccccc atcccgggat   1140
gagctgacca agaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaaga gcctctccct gtctccgggt aaatga                              1416

<210> SEQ ID NO 36
<211> LENGTH: 471
<212> TYPE: PRT
<213> ORGANISM: Artificial
<220> FEATURE:
<223> OTHER INFORMATION: Synthetic DNA

<400> SEQUENCE: 36

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Phe Val Lys
            20                  25                  30

```
Pro Gly Thr Ser Val Lys Leu Ser Cys Lys Ala Ser Gly Tyr Asn Phe
            35                  40                  45
Thr Arg Tyr Trp Ile Asn Trp Val Lys Leu Arg Pro Gly Gln Gly Leu
 50                  55                  60
Glu Trp Ile Gly Asn Ile Tyr Pro Ala Thr Asn Gly Ile Asn Tyr Asn
 65                  70                  75                  80
Glu Lys Phe Lys Ser Lys Ala Thr Leu Thr Val Asp Thr Phe Ser Ser
                85                  90                  95
Thr Ala Tyr Met Gln Leu Ser Ser Leu Ala Ser Glu Asp Ser Gly Leu
                100                 105                 110
Tyr Tyr Cys Ala Arg Cys Lys Thr Met Leu Ser Arg Cys Ala Trp Phe
            115                 120                 125
Pro Tyr Trp Gly Gln Gly Thr Leu Val Thr Val Ser Ala Ala Ser Thr
            130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
            195                 200                 205
Val Val Thr Val Pro Ser Ser Leu Gly Thr Gln Thr Tyr Ile Cys
            210                 215                 220
Asn Val Asn His Lys Pro Ser Asn Thr Lys Val Asp Lys Lys Val Glu
225                 230                 235                 240
Pro Lys Ser Cys Asp Lys Thr His Thr Cys Pro Pro Cys Pro Ala Pro
            245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
            290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
            355                 360                 365
Glu Pro Gln Val Tyr Thr Leu Pro Pro Ser Arg Asp Glu Leu Thr Lys
            370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
            405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
            435                 440                 445
```

```
Cys Ser Val Met His Glu Ala Leu His Asn His Tyr Thr Gln Lys Ser
    450                 455                 460
Leu Ser Leu Ser Pro Gly Lys
465                 470

<210> SEQ ID NO 37
<211> LENGTH: 705
<212> TYPE: DNA
<213> ORGANISM: Artificial
<220> FEATURE:
<223> OTHER INFORMATION: Synthetic DNA

<400> SEQUENCE: 37
atgatgtcct ctgctcagtt ccttggtctc ctgttgctct gttttcaagg ttccagatgt     60
gatatccaaa tgactcagac tacatcctcc ctgtctgcct ctctgggaga cagagtcacc    120
atcaattgca gggcaagtca ggacattagt aattatttaa actggtatca gcagaaacca    180
gatggaactg ttaaactcct gatctacgac acatcaagat acactcaag agtcccatca     240 aggttcagtg gcagtgggtc tggaacagat tattctctca ccattagcaa cctggagcaa    300
gaagatattg ccacttactt ttgccaacag gtaatatgc ttccgtggac gttcggtgga     360
ggcaccaagc tggaaatcaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                    705

<210> SEQ ID NO 38
<211> LENGTH: 234
<212> TYPE: PRT
<213> ORGANISM: Artificial
<220> FEATURE:
<223> OTHER INFORMATION: Synthetic DNA

<400> SEQUENCE: 38

Met Met Ser Ser Ala Gln Phe Leu Gly Leu Leu Leu Cys Phe Gln
1               5                  10                  15

Gly Ser Arg Cys Asp Ile Gln Met Thr Gln Thr Thr Ser Ser Leu Ser
            20                  25                  30

Ala Ser Leu Gly Asp Arg Val Thr Ile Asn Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Asp Thr Ser Arg Leu His Ser Arg Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Met Leu Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160
```

Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
        180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 39
<211> LENGTH: 1410
<212> TYPE: DNA
<213> ORGANISM: Artificial
<220> FEATURE:
<223> OTHER INFORMATION: Synthetic DNA

<400> SEQUENCE: 39
atgggttgga gcctcatctt gctcttcctt gtcgctgttg ctacgcgtgt cctgtccgag      60
gtccagctgc aacagtctgg acctgaggtg gtgaagcctg accttcact gaggatgtcc     120 tgcaaggcct ctggttactt tttcactggc aattctatga attgggtgaa gagacccat     180 ggacggagcc ttgagtggat tggacttatt gatctttcca atggtgaaac tcgcttcaat     240
cagaagttca agggcaaggc cactttaact gtggacaagt catccggcac agcctacatg     300
gaactcctca atctgacatc tgaggactct gcagtctatt actgtgcaag caggtctgcc     360
atgattatgc cctgtttttc tcattggggc caggggactc tggtcactgt ctctgcagct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc cccatcccg ggatgagctg     1140 accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                     1410

<210> SEQ ID NO 40
<211> LENGTH: 469
<212> TYPE: PRT
<213> ORGANISM: Artificial

<220> FEATURE:
<223> OTHER INFORMATION: Synthetic DNA

<400> SEQUENCE: 40

Met Gly Trp Ser Leu Ile Leu Leu Phe Leu Val Ala Val Ala Thr Arg
1               5                   10                  15

Val Leu Ser Glu Val Gln Leu Gln Gln Ser Gly Pro Glu Val Val Lys
            20                  25                  30

Pro Gly Pro Ser Leu Arg Met Ser Cys Lys Ala Ser Gly Tyr Phe Phe
        35                  40                  45

Thr Gly Asn Ser Met Asn Trp Val Lys Lys Thr His Gly Arg Ser Leu
    50                  55                  60

Glu Trp Ile Gly Leu Ile Asp Leu Ser Asn Gly Glu Thr Arg Phe Asn
65                  70                  75                  80

Gln Lys Phe Lys Gly Lys Ala Thr Leu Thr Val Asp Lys Ser Ser Gly
                85                  90                  95

Thr Ala Tyr Met Glu Leu Leu Asn Leu Thr Ser Glu Asp Ser Ala Val
            100                 105                 110

Tyr Tyr Cys Ala Ser Arg Ser Ala Met Ile Met Pro Cys Phe Ser His
        115                 120                 125

Trp Gly Gln Gly Thr Leu Val Thr Val Ser Ala Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
    435                 440                 445

Val Met His Glu Ala Leu His Asn His Tyr Thr Gln Lys Ser Leu Ser
450                 455                 460

Leu Ser Pro Gly Lys
465

<210> SEQ ID NO 41
<211> LENGTH: 705
<212> TYPE: DNA
<213> ORGANISM: Artificial
<220> FEATURE:
<223> OTHER INFORMATION: Synthetic DNA

<400> SEQUENCE: 41
atggagacac attctcaggt ctttgtatac atgttgctgt ggttgtctgg tattgaagga      60
gacattgtga tgacccagtc tcacaacttc atgtccacat caattggaga cagggtcaac     120
atcacctgca aggccagtca ggatgtggct actgctgttg cctggtttca acagaaacca     180
ggtcaatctc ctaaactcct aatttactgg acgtccaccc ggcacactgg agtccctgat     240
cgcttcacag gcagtggata tgggacagat ttcactctca ccattagcca tgtgcagtct     300
gaagacttgg ccgattattt ctgtcaacaa tatgacacct atccgtacac gttcggaggg     360
gggaccaagt tggagataaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacccctgacg   600 ctgagcaaag cagactacga gaaacacaaa gtctacgcct gcgaagtcac ccatcagggc    660
ctgagctcgc ccgtcacaaa gagcttcaac aggggagagt gttag                    705

<210> SEQ ID NO 42
<211> LENGTH: 234
<212> TYPE: PRT
<213> ORGANISM: Artificial
<220> FEATURE:
<223> OTHER INFORMATION: Synthetic DNA

<400> SEQUENCE: 42

Met Glu Thr His Ser Gln Val Phe Val Tyr Met Leu Leu Trp Leu Ser
1               5                   10                  15

Gly Ile Glu Gly Asp Ile Val Met Thr Gln Ser His Asn Phe Met Ser
            20                  25                  30

Thr Ser Ile Gly Asp Arg Val Asn Ile Thr Cys Lys Ala Ser Gln Asp
        35                  40                  45

Val Ala Thr Ala Val Ala Trp Phe Gln Gln Lys Pro Gly Gln Ser Pro
    50                  55                  60

Lys Leu Leu Ile Tyr Trp Thr Ser Thr Arg His Thr Gly Val Pro Asp
65                  70                  75                  80

Arg Phe Thr Gly Ser Gly Tyr Gly Thr Asp Phe Thr Leu Thr Ile Ser
                85                  90                  95

His Val Gln Ser Glu Asp Leu Ala Asp Tyr Phe Cys Gln Gln Tyr Asp
            100                 105                 110

-continued

```
Thr Tyr Pro Tyr Thr Phe Gly Gly Thr Lys Leu Glu Ile Lys Arg
        115                 120             125

Thr Val Ala Ala Pro Ser Val Phe Ile Phe Pro Pro Ser Asp Glu Gln
    130             135                 140

Leu Lys Ser Gly Thr Ala Ser Val Val Cys Leu Leu Asn Asn Phe Tyr
145             150                 155                     160

Pro Arg Glu Ala Lys Val Gln Trp Lys Val Asp Asn Ala Leu Gln Ser
                165             170                     175

Gly Asn Ser Gln Glu Ser Val Thr Glu Gln Asp Ser Lys Asp Ser Thr
            180             185                     190

Tyr Ser Leu Ser Ser Thr Leu Thr Leu Ser Lys Ala Asp Tyr Glu Lys
        195             200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

THERAPEUTIC PHARMACEUTICAL COMPOSITION EMPLOYING ANTI-SLC6A6 ANTIBODY

TECHNICAL FIELD

The present invention relates a pharmaceutical composition, which comprises a monoclonal antibody recognizing an extracellular domain of SLC6A6. More specifically, the present invention relates an antibody conjugate configured such that a monoclonal antibody recognizing an extracellular domain of SLC6A6 is conjugated with an anticancer agent or the like having activity against cancer and other hyperproliferative diseases, as well as a pharmaceutical composition for treatment of cancers including colorectal cancer, which comprises such a conjugate.

BACKGROUND ART

Cancer ranks high in the causes of death in the world. Above all, colorectal cancer is a disease being at a higher position in the mortality of cancer. In Japan, the number of colorectal cancer patients has been suddenly increasing in recent years, and about 60,000 patients suffer from colorectal cancer every year. In the number of deaths classified by organ system, colorectal cancer ranks third after gastric cancer and lung cancer. Colorectal cancer has a five-year survival rate of about 90% or more when remaining only in the colon or rectum, and is therefore known as a cancer for which early diagnosis leads to a higher healing rate. In spite of this fact, colorectal cancer is a high-mortality cancer. This is because colorectal cancer not only has high morbidity, but also shows a sudden increase in mortality with the progression of cancer, i.e., its five-year survival rate is reduced to 70% upon metastasis to lymph nodes and reduced to 25% or less upon distant metastasis to the lung or liver. For treatment of such colorectal cancer, surgical treatment and chemotherapy are commonly used, while attempts have also been made to search for cancer-specific new therapies since the recent appearance of molecular targeted drugs.

As antibody drugs approved in Japan for use as molecular targeted drugs for colorectal cancer, Avastin and Erbitux are known. They are antibody drugs targeted at growth factors such as vascular endothelial growth factor (VEGF) and epidermal growth factor (EGF). Avastin is approved for use in progressive and recurrent colorectal cancer for which curative resection is impossible. Avastin works by a mechanism of action which involves binding to VEGF to prevent its binding to VEGF receptors, thereby inhibiting vascularization and blocking nutrition to tumor tissues.

Erbitux is intended to stop the proliferation of cancer cells through binding to EGF receptors (EGFR) and thereby inhibiting EGF-mediated cell proliferation signals. Moreover, another mechanism of action also appears to work, i.e., antibody biding to the surface of cancer cells will cause antibody-dependent cellular cytotoxicity (ADCC) mediated by natural killer cells (NK cells) and/or macrophages, etc., whereby the cancer cells will be killed.

When compared to normal cells, cancer cells are characterized by having high proliferative ability, having no limit on the number of cell divisions, and causing invasion and/or metastasis to surrounding tissues. Recent studies have indicated that some limited number, but not all, of the cancer cells in cancer tissue have such properties. Namely, these limited number of cancer cells have self-replication ability (i.e., the ability to produce completely the same cells as themselves) and pluripotency (i.e., the ability to differentiate into many different cell types), which are characteristics common to stem cells including embryonic stem cells and somatic stem cells. Due to these characteristics, cancer cells would act not only to maintain the same cells as themselves in cancer tissue through self-replication, but also to generate the great majority of surrounding cancer cells as a result of differentiation. Such a limited number of cancer cells are called cancer stem cells, and there has been proposed a hypothesis that cancer occurs and progresses from these stem cell-like cells (cancer stem cell hypothesis).

Currently known cancer stem cell markers include molecular markers such as CD133, CD24, CD44 and so on (Non-patent Document 1: GASTROENTEROLOGY, 138, 2151-2162, 2010). However, antibodies against these markers bind to only some cancer stem cells and are therefore regarded as having no efficacy as therapeutic agents. On the other hand, LGR5 has a mechanism to activate Wnt/β-catenin signals through interaction with R-spondin and is therefore suggested to have the potential to be used as a cancer stem cell marker (Patent Document 1: JP 2010-532169 A).

Cancer stem cells are considered to be a major factor for cancer recurrence and/or metastasis, and the importance of targeting cancer stem cells in cancer treatment has been pointed out. However, cancer stem cells constitute only a few percentages in tumor tissue, and hence therapeutic agents designed to target only cancer stem cells would not be able to kill cancer cells in general. Namely, for cancer medication, it is an important problem to develop a new therapy targeting a marker which is expressed at an extremely higher level in cancer stem cells than in normal tissues and is also expressed in common cancer cells.

Molecular targeted drugs, typified by antibodies, are superior agents in terms of killing cancer cells upon specifically recognizing cancer. However, molecular targeted drugs will cause serious side effects in some cases when antibodies also bind to normal cells. For example, Herceptin, which is a therapeutic agent for breast cancer, may cause not only headache, asthenia, nausea and vomiting, but also interstitial pneumonia, bone marrow inhibition, hepatic disorders, renal disorders and cerebrovascular disorders. Moreover, in tissue staining, Herceptin is also known to strongly react with normal cardiomyocytes to thereby cause severe cardiac disorders (Non-patent Document 2: British Journal of Cancer, 94, 1016-1020, 2006). Further, Herceptin is an antibody drug targeted at Her2, and hence there remains a problem in that Herceptin is effective only for patients who express Her2.

In the case of Avastin, which is a therapeutic agent for colorectal cancer, its side effects include hemorrhage, thrombosis, gastrointestinal perforation, delayed wound healing, increased blood pressure and so on, among which thrombosis and gastrointestinal perforation are fatal side effects (Non-patent Document 3: Cancer Research, 57, 4593-4599, 1997). Side effects known for Erbitux include skin disorders and so on, which are not fatal but cause itching and white pustules, resulting in mental and physical burdens on patients (Non-patent Document 4: Journal of Clinical Oncology, 22, 1201-1208, 2004). Moreover, Erbitux also has a problem in that it has no effect on canceration caused by a change in signals downstream of EGFR (e.g., K-ras mutation).

Drug delivery systems are also widely known, which are designed to transport a drug by means of the ability of molecular targeted drugs (e.g., antibodies) to bind to the cell surface. In particular, recent efforts have been made to effectively deliver a drug to the surface of cancer cells and thereby more effectively kill the cancer cells, and attempts have been made to cause uptake of antibody molecules into cells for this purpose. Antibody molecules are not taken up into cells in normal cases because they cannot permeate through the cell membrane. However, certain types of antibodies are known to be taken up into cells via a mechanism called internalization through biding to membrane protein molecules on the cell membrane.

EGF receptors (EGFR), when bound to its ligand EGF (i.e., a molecule binding to these receptors), are transported into cells by clathrin-mediated endocytosis or the like, localized in endosomes and then degraded in lysosomes (Non-patent Document 5: Cell Division, 2, 11, 2007). During this process, certain types of antibodies are also known to be taken up into cells upon binding to EGF receptors, as in the case where the ligand binds to these receptors. By means of this mechanism, attempts have been started to develop a therapy such that a drug is linked to an antibody and the antibody is efficiently transported into cells.

Membrane proteins include not only receptors binding to their ligands, but also transport proteins (hereinafter referred to as transporters) which allow active or passive transport of low molecular compounds such as amino acids and sugars. These molecules have been considered not to cause internalization because they are responsible for allowing permeation of molecules inside and outside of cells.

WO2012/029990 (Patent Document 2) shows that SLC6A6 is expressed in colorectal cancer, and a monoclonal antibody recognizing its extracellular domain can be used to detect colorectal cancer and therefore can be used as a diagnostic agent. SLC6A6 (solute carrier family 6 (neurotransmitter transporter, taurine), member 6) is a 12-transmembrane protein consisting of 620 amino acids and has been registered at NCBI (the National Center for Biotechnology Information) under Reference Sequences [RefSeq] ID: NM_003043 and NP_003034.2 (SEQ ID NO: 1: nucleotide sequence (CDS: 296 to 2158), SEQ ID NO: 2: amino acid sequence). SLC6A6 is involved in taurine uptake into cells and transports taurine together with sodium ions and chloride ions.

Moreover, Patent Document 2 shows that the SLC6A6 gene is expressed in all 5 cases of colorectal cancer tissue, whereas gene transcription is not observed in 5 cases of normal tissue, as identified by in situ hybridization techniques. Further, it is shown that two clones (4B9b and 5H12d) of the obtained monoclonal antibodies each have an epitope between amino acid residues 145 and 213 in the SLC6A6 protein.

Antibody drugs against cancer still have problems, e.g., in that they will cause serious side effects and are effective only for limited patients. Thus, there has been a demand for new development of cancer-specific molecular targets and pharmaceutical preparations with fewer side effects.

PRIOR ART DOCUMENTS

Patent Documents

[Patent Document 1] JP 2010-532169 A
[Patent Document 2] WO2012/029990

Non-Patent Documents

[Non-patent Document 1] GASTROENTEROLOGY, 138, 2151-2162, 2010
[Non-patent Document 2] British Journal of Cancer, 94, 1016-1020, 2006
[Non-patent Document 3] Cancer Research, 57, 4593-4599, 1997
[Non-patent Document 4] Journal of Clinical Oncology, 22, 1201-1208, 2004
[Non-patent Document 5] Cell Division, 2, 11, 2007

SUMMARY OF THE INVENTION

Problem to be Solved by the Invention

In general, surgical treatment of cancer has problems not only in that it is difficult to treat metastatic lesions, but also in that it involves invasion and occurrence of complications. Moreover, chemotherapy and radiation therapy have problems of side effects. Further, existing antibody drugs not only cause side effects, but also have no effect on some cancers. For these reasons, there has been a demand for the development of cancer-specific molecular targets and new pharmaceutical preparations with fewer side effects.

The present invention aims to provide a pharmaceutical composition which comprises an antibody or an antigen-binding fragment thereof, more specifically a pharmaceutical composition which comprises an antibody conjugate composed of an antibody or an antigen-binding fragment thereof in combination with one or more chemotherapeutic agents, and particularly a pharmaceutical composition for cancer treatment.

Means to Solve the Problem

As a result of repeating extensive and intensive efforts to solve the problems stated above, the inventors of the present invention have obtained a new monoclonal antibody containing an epitope in the same region as that of the anti-SLC6A6 monoclonal antibodies disclosed in WO2012/029990 and having increased affinity. SLC6A6, which is a membrane protein overexpressed in cancer tissues, is also useful as a cancer marker. The inventors of the present invention have found that SLC6A6 is expressed at a higher level in cancer stem cells serving as a major factor for cancer recurrence and/or metastasis than in common cancer cells. In addition, the inventors of the present invention have found that the antibody alone does not exert the effect of killing cancer cells, whereas the antibody bound to SLC6A6 is taken up into cells. Moreover, as a result of developing a conjugate composed of the antibody and a chemotherapeutic agent(s) linked thereto, the inventors of the present invention have found that cancer cells can be killed effectively, and thereby have completed the present invention.

Namely, the present invention is as follows.

[1] A pharmaceutical composition for cancer treatment, which comprises a monoclonal antibody or an antigen-binding fragment thereof, each binding to a three-dimensionally structured epitope within the extracellular region of SLC6A6.

[2] The pharmaceutical composition according to [1] above, wherein the monoclonal antibody is conjugated with an anticancer agent, a toxin or a radioisotope.

[3] A pharmaceutical composition for cancer treatment, which comprises an antibody conjugate configured such that a monoclonal antibody or an antigen-binding fragment thereof, each binding to a three-dimensionally structured epitope within the extracellular region of SLC6A6, is conjugated with an anticancer agent, a toxin or a radioisotope.

[4] The pharmaceutical composition according to any one of [1] to [3] above, wherein the epitope comprises a polypeptide shown in at least one selected from (a) to (c) shown below:

(a) a polypeptide which consists of the amino acid sequence shown in SEQ ID NO: 4;
(b) a polypeptide which consists of an amino acid sequence with substitution, deletion and/or insertion of one or several amino acids in the amino acid sequence shown in SEQ ID NO: 4 and which serves as an extracellular region of SLC6A6; and
(c) a polypeptide which consists of an amino acid sequence sharing a homology of 70% or more with the amino acid sequence shown in SEQ ID NO: 4 and which serves as an extracellular region of SLC6A6.

[5] The pharmaceutical composition according to any one of [1] to [4] above, wherein the monoclonal antibody is at least one selected from the group consisting of:
(a) an antibody which comprises a heavy chain variable region comprising amino acid sequences located at positions 50 to 54, positions 69 to 86 and positions 118 to 125 in SEQ ID NO: 24 as heavy chain CDR1, CDR2 and CDR3, respectively, and a light chain variable region comprising amino acid sequences located at positions 44 to 54, positions 70 to 76 and positions 109 to 116 in SEQ ID NO: 26 as light chain CDR1, CDR2 and CDR3, respectively;
(b) an antibody which comprises a heavy chain variable region comprising amino acid sequences located at positions 50 to 54, positions 69 to 86 and positions 118 to 126 in SEQ ID NO: 28 as heavy chain CDR1, CDR2 and CDR3, respectively, and a light chain variable region comprising amino acid sequences located at positions 46 to 57, positions 73 to 79 and positions 112 to 119 in SEQ ID NO: 30 as light chain CDR1, CDR2 and CDR3, respectively;
(c) an antibody which comprises a heavy chain variable region comprising amino acid sequences located at positions 50 to 54, positions 69 to 86 and positions 118 to 128 in SEQ ID NO: 32 as heavy chain CDR1, CDR2 and CDR3, respectively, and a light chain variable region comprising amino acid sequences located at positions 48 to 58, positions 74 to 80 and positions 113 to 120 in SEQ ID NO: 34 as light chain CDR1, CDR2 and CDR3, respectively;
(d) an antibody which comprises a heavy chain variable region comprising amino acid sequences located at positions 50 to 54, positions 69 to 86 and positions 118 to 131 in SEQ ID NO: 36 as heavy chain CDR1, CDR2 and CDR3, respectively, and a light chain variable region comprising amino acid sequences located at positions 44 to 54, positions 70 to 76 and positions 109 to 116 in SEQ ID NO: 38 as light chain CDR1, CDR2 and CDR3, respectively;
(e) an antibody which comprises a heavy chain variable region comprising amino acid sequences located at positions 50 to 54, positions 69 to 86 and positions 118 to 129 in SEQ ID NO: 40 as heavy chain CDR1, CDR2 and CDR3, respectively, and a light chain variable region comprising amino acid sequences located at positions 44 to 54, positions 70 to 76 and positions 109 to 116 in SEQ ID NO: 42 as light chain CDR1, CDR2 and CDR3, respectively; and
(f) an antibody which comprises a heavy chain variable region comprising amino acid sequences located at positions 50 to 54, positions 69 to 86 and positions 118 to 126 in SEQ ID NO: 44 as heavy chain CDR1, CDR2 and CDR3, respectively, and a light chain variable region comprising amino acid sequences located at positions 46 to 57, positions 73 to 79 and positions 112 to 119 in SEQ ID NO: 46 as light chain CDR1, CDR2 and CDR3, respectively.

[6] The pharmaceutical composition according to any one of [1] to [4] above, wherein the monoclonal antibody binds to an epitope recognized by the monoclonal antibody or fragment thereof according to [5] above.

[7] The pharmaceutical composition according to any one of [1] to [6] above, wherein the monoclonal antibody is a chimeric antibody or a humanized antibody.

[8] The pharmaceutical composition according to any one of [1] to [7] above, wherein the toxin is at least one selected from the group consisting of diphtheria toxin, *Pseudomonas* endotoxin and exotoxin, Staphylococcal enterotoxin A, fungal, plant, antiviral proteins, saporin, gelonin, momordin, trichosanthin, barley toxin, *Aleurites fordii* proteins, dianthin proteins, *Phytolacca americana* proteins, *Momordica charantia* inhibitor, curcin, crotin, *Sapaonaria officinalis* inhibitor, gelonin, mitogellin, restrictocin, phenomycin, neomycin, and trichothecene.

[9] The pharmaceutical composition according to any one of [1] to [7] above, wherein the anticancer agent is a pharmaceutical agent for treatment of colorectal cancer, breast cancer or uterine cancer.

[10] The pharmaceutical composition according to any one of [1] to [9] above, which is intended for treatment of colorectal cancer, breast cancer or uterine cancer.

[11] The pharmaceutical composition according to any one of [1] to [10] above, which further comprises at least one anticancer agent.

Effects of the Invention

The present invention provides a monoclonal antibody specifically binding to the extracellular region of SLC6A6. Moreover, the present invention provides an antibody conjugate comprising an anti-SLC6A6 monoclonal antibody or an antigen-binding fragment thereof and at least one anticancer agent, toxin or radioisotope linked thereto, as well as a pharmaceutical composition comprising such an antibody conjugate. Since the monoclonal antibody of the present invention specifically binds to cancer cells expressing SLC6A6 and is thereby internalized in these cells, the antibody conjugate and the pharmaceutical composition according to the present invention are useful for cancer treatment, particularly for use as a pharmaceutical composition for colorectal cancer treatment. The antibody may be humanized or chimeric, and it is therefore possible to reduce side effects upon application to humans.

Moreover, SLC6A6 is expressed at an extremely higher level in cancer stem cells than in normal tissues and is also expressed in common cancer cells. Thus, the present invention provides a new therapeutic agent or method for cancer, which is designed to target not only cancer stem cells, but also cancer cells in general.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 11A shows the results analyzed for antibody uptake into cells.

FIG. 14A shows the results indicating that toxicity is exerted in cells as a result of internalization of monoclonal antibody.

DESCRIPTION OF EMBODIMENTS

Figure 1:
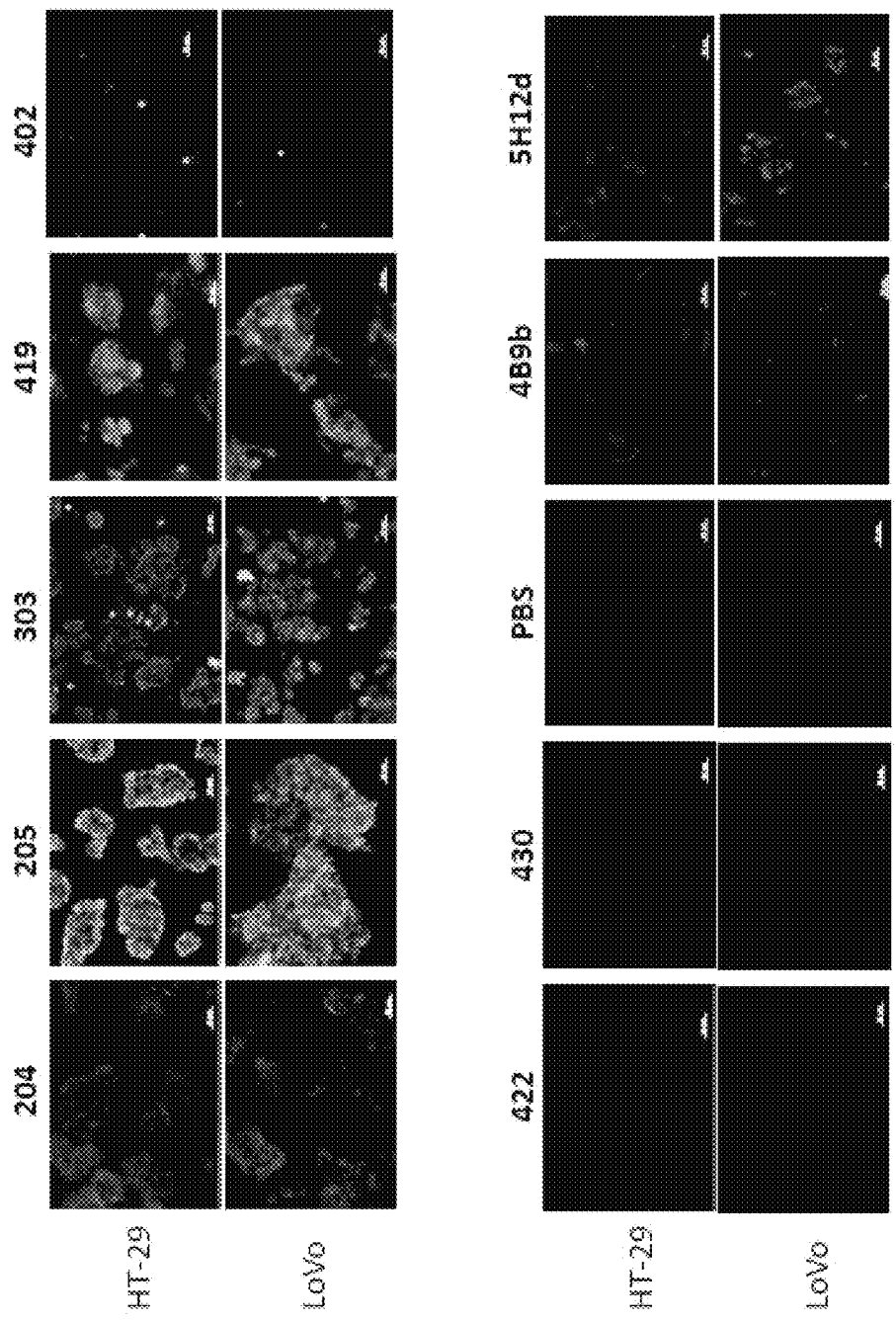
FIG. 1 shows immunohistological staining in two lines of colorectal cancer cells (HT-29 and LoVo) for monoclonal antibody clones 204, 205, 303, 419, 402, 422 and 430.

The present invention will be described in more detail below. It should be noted that the present invention is not limited to the following embodiments and can be implemented with modifications, as appropriate, within the spirit of the present invention. In addition, all reference documents cited herein, including patents, patent applications and other documents, are incorporated herein by reference in their entirety.

The present invention is based on the finding that the membrane protein SLC6A6 is a protein overexpressed in cancer tissues and is a useful marker as a target of treatment. Further, the present invention is also based on the finding that SLC6A6 is expressed at a higher level in cancer stem cells serving as a major factor for cancer recurrence and/or metastasis than in common cancer cells. In the present invention, there is provided an antibody having higher affinity than conventional anti-SLC6A6 antibodies. Moreover, it has been found that such an antibody of the present invention allows effective delivery of anticancer agents or the like to cancer cells and further allows their uptake into the cells.

The present invention relates to a pharmaceutical composition comprising a monoclonal antibody or an antigen-binding fragment thereof, which recognizes the extracellular region of a molecule called SLC6A6 (solute carrier family 6 (neurotransmitter transpoter, taurine), member 6). Since SLC6A6 is expressed in colorectal cancer, this antibody specifically binds to particularly colorectal cancer cells.

More specifically, the present invention relates to a pharmaceutical composition comprising an antibody conjugate, whose mechanism of action involves using an antibody conjugate comprising the above antibody linked (hereinafter expressed as "conjugated") with an anticancer agent (e.g., a chemotherapeutic agent), a toxin or a radioisotope to thereby cause uptake of the chemotherapeutic agent or the like into cancer cells. Thus, the pharmaceutical composition of the present invention is useful for treatment of cancer, particularly colorectal cancer.

1. The Monoclonal Antibody of the Present Invention
(1) The Monoclonal Antibody of the Present Invention The monoclonal antibody to be used in the pharmaceutical composition of the present invention (hereinafter also referred to as "the monoclonal antibody of the present invention") is capable of recognizing native SLC6A6. The term "native" is intended to mean being in a state of retaining the intact three-dimensional structure which is taken by the intended protein in an in vivo environment.

Moreover, the monoclonal antibody of the present invention is capable of recognizing the extracellular region of SLC6A6. More specifically, the monoclonal antibody of the present invention binds to a three-dimensionally structured epitope within the extracellular region of SLC6A6. In particular, it is capable of recognizing a region covering amino acid residues 143 to 216 of SLC6A6 (SEQ ID NO: 4) as an extracellular region.

Within the range of retaining the binding activity to a polypeptide having the amino acid sequence shown in SEQ ID NO: 4, i.e., as long as a target polypeptide has functions as the extracellular region of SLC6A6, the monoclonal antibody of the present invention may also recognize a mutated polypeptide comprising substitution, deletion or insertion of one or several (e.g., 2 to 20, preferably 2 to 10, more preferably 2, 3, 4 or 5) amino acids in the amino acid sequence shown in SEQ ID NO: 4 or a mutated polypeptide sharing a homology of 70% or more, preferably 80% or more, 90% or more, 95% or more, or 98% or more with the amino acid sequence shown in SEQ ID NO: 4.

Moreover, the monoclonal antibody of the present invention may recognize a polypeptide having functions as the extracellular region of SLC6A6 and being a polypeptide encoded by a polynucleotide consisting of the nucleotide sequence shown in SEQ ID NO: 3, a polypeptide encoded by a polynucleotide comprising the nucleotide sequence shown in SEQ ID NO: 3, a mutated polypeptide encoded by a polynucleotide sharing a homology of 70% or more, preferably 80% or more, 90% or more, 95% or more, 98% or more, or 99% or more with the nucleotide sequence shown in SEQ ID NO: 3, or a mutated polypeptide encoded by a polynucleotide comprising a nucleotide sequence hybridizable under high stringent conditions with the nucleotide sequence shown in SEQ ID NO: 3. For this purpose, hybridization may be accomplished in a known manner (e.g., Molecular Cloning 2nd Ed (Cold Spring Harbor Lab. Press, 1989). High stringent conditions refer to so-called conditions under which a specific hybrid is formed and any non-specific hybrid is not formed. For example, high stringent conditions refer to conditions at a sodium concentration of 10 mM to 300 mM, preferably 20 mM to 100 mM and at a temperature of 25° C. to 70° C., preferably 42° C. to 55° C.

The extracellular region of SLC6A6 is predicted to be responsible for binding with taurine and transport of taurine into cells. Confirmation of whether or not a mutated polypeptide has functions as an extracellular domain of SLC6A6 will be able to be accomplished by forcing the mutated polypeptide to be expressed in animal cells or the like and analyzing taurine uptake by the activation method (J. Membr. Biol, 76, 1-15, 1983).

Alternatively, since the monoclonal antibody of the present invention binds to SLC6A6, among the above mutated polypeptides, those to which the monoclonal antibody of the present invention can bind indicate that the antibody maintains its binding activity to a polypeptide having the amino acid sequence shown in SEQ ID NO: 4, i.e., they fall within polypeptides having functions as the extracellular region of SLC6A6.

Binding between a mutated polypeptide and the monoclonal antibody of the present invention may be confirmed by ELISA, immunoprecipitation, western blotting, etc.

Moreover, the extracellular region of SLC6A6 corresponds to a cell surface site of a marker protein whose expression is increased in cancer cells. Confirmation of whether or not a mutated polypeptide has functions as an extracellular domain of SLC6A6 may be accomplished by comparing the expression of the mutated polypeptide between normal cells and cancer cells by means of immunostaining, ELISA, immunoprecipitation, western blotting, FACS, etc.

The monoclonal antibody of the present invention is of subclass IgG, unlike the SLC6A6 antibodies of subclass IgM disclosed in WO2012/029990, and is shown to have higher affinity against SLC6A6 when analyzed by immunohistological staining and/or with a flow cytometer. Moreover, the monoclonal antibody of the present invention has the property of being taken up into cells through a mechanism called internalization.

The monoclonal antibody of the present invention also recognizes proteins encoded by mRNA variants of slc6a6. The monoclonal antibody of the present invention can bind not only to full-length SLC6A6, but also to partially deficient mutants thereof, and is therefore capable of binding to a wide range of SLC6A6-expressing cancer cells.

In the present invention, various genetic engineering and protein engineering procedures can be used to prepare antigen-binding fragments which are portions of the monoclonal antibody, for example, antibody fragments, antibody-like molecules (e.g., low molecular antibody, genetically recombinant antibody, modified antibody), or a protein fused with the monoclonal antibody. More specifically, examples include H chain, L chain, Fv, Fab, Fab', F(ab')2, scFv, sdFv, sc(Fv)2, (scFv)2, DiAbody, chimeric antibody, humanized antibody, human antibody, single chain antibody, multi-specific antibody (e.g., bispecific antibody), labeled antibody and so on. All of them fall within the monoclonal antibody of the present invention as long as they are molecules having the ability to bind to the extracellular region of SLC6A6.

SLC6A6 recognized by the monoclonal antibody of the present invention is a molecular marker which is expressed in cancer cells, but not in normal cells, in a population of cells to be detected and which further shows higher expression in cancer stem cells than in cancer cells. Thus, the antibody binds to both cancer and cancer stem cells, and binds more to cancer stem cells.

In the context of the present invention, the term "cancer cells" is intended to mean a population of cells characterized by having high proliferative ability, having no limit on the number of cell divisions, and causing invasion and/or metastasis to surrounding tissues, when compared to normal cells.

In the context of the present invention, the term "cancer stem cells" is intended to mean cells with stem cell properties among cancer cells. Stem cells refer to cells retaining the ability to differentiate even after cell divisions. When stained with a Hoechst fluorescent dye (Hoechst 33342) and detected by flow cytometry using a UV laser (wavelength: about 350 nm) as an excitation light, cancer stem cells are confirmed as cells enriched in the side population (SP) fraction. In contrast to the main population (MP) fraction which is stained with the Hoechst fluorescent dye, the SP fraction refers to a fraction which is not or weakly stained because the dye is effluxed into the extracellular environment through ABC transporters or the like (The American Journal of Pathology, 178, 4, 1805-1813, 2011).

In the context of the present invention, the term "normal cells" refers to cells having normal functions in vivo or in tissue activities. Such normal cells may include somatic stem cells, but are preferably mature cells.

The monoclonal antibody of the present invention is preferably one which is ubiquitously expressed in cancer cells of multiple cancer types and more strongly binds to cancer stem cells, and is able to bind to multiple cancer types. Preferred are multiple cancer types of cellular or tissue origin (e.g., heart, brain, placenta, lung, liver, skeletal muscle, kidney, pancreas, spleen, thymus, prostate, testis, ovary, small intestine, leukocytes, colon, stomach, bone marrow, colon and rectum, and peripheral blood mononuclear cells), and more preferred are cancer cells from colorectal cancer, breast cancer and uterine cancer.

Further, the monoclonal antibody of the present invention does not bind to normal cells. Preferably, the monoclonal antibody of the present invention does not bind to normal cells in at least one or more of heart, brain, placenta, lung, skeletal muscle, kidney, spleen, thymus, prostate, testis, ovary, small intestine, leukocytes, colon, bone marrow, colon and rectum, and peripheral blood mononuclear cells, by way of example.

Preferred cell lines (hybridomas) producing the monoclonal antibody of the present invention are, for example:

"mouse-mouse hybridoma 204" (hereinafter referred to as "204");

"mouse-mouse hybridoma 205" (hereinafter referred to as "205");

"mouse-mouse hybridoma 303" (hereinafter referred to as "303");

"mouse-mouse hybridoma 419" (hereinafter referred to as "419");

"mouse-mouse hybridoma 402" (hereinafter referred to as "402");

"mouse-mouse hybridoma 422" (hereinafter referred to as "422"); and

"mouse-mouse hybridoma 430" (hereinafter referred to as "430").

The present invention provides these hybridomas and antibodies produced therefrom. When these hybridomas are cultured, it is possible to prepare homogeneous monoclonal antibodies.

The antibody produced from 205 comprises a heavy chain variable region comprising an amino acid sequence located at positions 21 to 135 in SEQ ID NO: 24 and a light chain variable region comprising an amino acid sequence located at positions 21 to 127 in SEQ ID NO: 26.

Alternatively, the antibody produced from 205 comprises a heavy chain variable region comprising amino acid sequences located at positions 50 to 54, positions 69 to 86 and positions 118 to 125 in SEQ ID NO: 24 as heavy chain CDR1, CDR2 and CDR3, respectively, and a light chain variable region comprising amino acid sequences located at positions 44 to 54, positions 70 to 76 and positions 109 to 116 in SEQ ID NO: 26 as light chain CDR1, CDR2 and CDR3, respectively.

The antibody produced from 402 comprises a heavy chain variable region comprising an amino acid sequence located at positions 21 to 136 in SEQ ID NO: 28 and a light chain variable region comprising an amino acid sequence located at positions 23 to 130 in SEQ ID NO: 30.

Alternatively, the antibody produced from 402 comprises a heavy chain variable region comprising amino acid sequences located at positions 50 to 54, positions 69 to 86 and positions 118 to 126 in SEQ ID NO: 28 as heavy chain CDR1, CDR2 and CDR3, respectively, and a light chain variable region comprising amino acid sequences located at positions 46 to 57, positions 73 to 79 and positions 112 to 119 in SEQ ID NO: 30 as light chain CDR1, CDR2 and CDR3, respectively.

The antibody produced from 419 comprises a heavy chain variable region comprising an amino acid sequence located at positions 21 to 138 in SEQ ID NO: 32 and a light chain variable region comprising an amino acid sequence located at positions 25 to 131 in SEQ ID NO: 34.

Alternatively, the antibody produced from 419 comprises a heavy chain variable region comprising amino acid sequences located at positions 50 to 54, positions 69 to 86 and positions 118 to 128 in SEQ ID NO: 32 as heavy chain CDR1, CDR2 and CDR3, respectively, and a light chain variable region comprising amino acid sequences located at positions 48 to 58, positions 74 to 80 and positions 113 to 120 in SEQ ID NO: 34 as light chain CDR1, CDR2 and CDR3, respectively.

The antibody produced from 303 comprises a heavy chain variable region comprising an amino acid sequence located at positions 21 to 141 in SEQ ID NO: 36 and a light chain variable region comprising an amino acid sequence located at positions 21 to 127 in SEQ ID NO: 38.

Alternatively, the antibody produced from 205 comprises a heavy chain variable region comprising amino acid sequences located at positions 50 to 54, positions 69 to 86 and positions 118 to 131 in SEQ ID NO: 36 as heavy chain CDR1, CDR2 and CDR3, respectively, and a light chain variable region comprising amino acid sequences located at positions 44 to 54, positions 70 to 76 and positions 109 to 116 in SEQ ID NO: 38 as light chain CDR1, CDR2 and CDR3, respectively.

The antibody produced from 422 comprises a heavy chain variable region comprising an amino acid sequence located at positions 21 to 139 in SEQ ID NO: 40 and a light chain variable region comprising an amino acid sequence located at positions 21 to 127 in SEQ ID NO: 42.

Alternatively, the antibody produced from 205 comprises a heavy chain variable region comprising amino acid sequences located at positions 50 to 54, positions 69 to 86 and positions 118 to 129 in SEQ ID NO: 40 as heavy chain CDR1, CDR2 and CDR3, respectively, and a light chain variable region comprising amino acid sequences located at positions 44 to 54, positions 70 to 76 and positions 109 to 116 in SEQ ID NO: 42 as light chain CDR1, CDR2 and CDR3, respectively.

The antibody produced from 430 comprises a heavy chain variable region comprising an amino acid sequence located at positions 21 to 136 in SEQ ID NO: 44 and a light chain variable region comprising an amino acid sequence located at positions 23 to 130 in SEQ ID NO: 46.

Alternatively, the antibody produced from 205 comprises a heavy chain variable region comprising amino acid sequences located at positions 50 to 54, positions 69 to 86 and positions 118 to 126 in SEQ ID NO: 44 as heavy chain CDR1, CDR2 and CDR3, respectively, and a light chain variable region comprising amino acid sequences located at positions 46 to 57, positions 73 to 79 and positions 112 to 119 in SEQ ID NO: 46 as light chain CDR1, CDR2 and CDR3, respectively.

The monoclonal antibody of the present invention may be an antibody whose heavy chain has an amino acid sequence sharing an identity of at least 70%, 75%, 80%, 81%, 82%, 83%, 84%, 85%, 86%, 87%, 88%, 89%, 90%, 91%, 92%, 93%, 94%, 95%, 96%, 97%, 98% or 99% with the amino acid sequence shown in SEQ ID NO: 24, 28, 32, 36, 40 or 44 and whose light chain has an amino acid sequence sharing an identity of at least 70%, 75%, 80%, 81%, 82%, 83%, 84%, 85%, 86%, 87%, 88%, 89%, 90%, 91%, 92%, 93%, 94%, 95%, 96%, 97%, 98% or 99% with the amino acid sequence shown in SEQ ID NO: 26, 30, 34, 38, 42 or 46.

Further, the monoclonal antibody of the present invention may be an antibody:

whose heavy chain variable region comprises an amino acid sequence sharing an identity of at least 75%, 80%, 81%, 82%, 83%, 84%, 85%, 86%, 87%, 88%, 89%, 90%, 91%, 92%, 93%, 94%, 95%, 96%, 97%, 98% or 99% with an amino acid sequence located at positions 21 to 135 in SEQ ID NO: 24, with an amino acid sequence located at positions 21 to 136 in SEQ ID NO: 28, with an amino acid sequence located at positions 21 to 138 in SEQ ID NO: 32, with an amino acid sequence located at positions 21 to 141 in SEQ ID NO: 36, with an amino acid sequence located at positions 21 to 139 in SEQ ID NO: 40 or with an amino acid sequence located at positions 21 to 136 in SEQ ID NO: 44; and whose light chain variable region comprises an amino acid sequence sharing an identity of at least 75%, 80%, 81%, 82%, 83%, 84%, 85%, 86%, 87%, 88%, 89%, 90%, 91%, 92%, 93%, 94%, 95%, 96%, 97%, 98% or 99% with an amino acid sequence located at positions 21 to 127 in SEQ ID NO: 26, with an amino acid sequence located at positions 23 to 130 in SEQ ID NO: 30, with an amino acid sequence located at positions 25 to 131 in SEQ ID NO: 34, with an amino acid sequence located at positions 21 to 127 in SEQ ID NO: 38, with an amino acid sequence located at positions 21 to 127 in SEQ ID NO: 42 or with an amino acid sequence located at positions 23 to 130 in SEQ ID NO: 46.

Further, the monoclonal antibody of the present invention may be an antibody:

whose heavy chain variable region comprises amino acid sequences sharing an identity of at least 80%, 81%, 82%, 83%, 84%, 85%, 86%, 87%, 88%, 89%, 90%, 91%, 92%, 93%, 94%, 95%, 96%, 97%, 98% or 99% with amino acid sequences located at positions 50 to 54, positions 69 to 86 and positions 118 to 125 in SEQ ID NO: 24, with amino acid sequences located at positions 50 to 54, positions 69 to 86 and positions 118 to 126 in SEQ ID NO: 28, with amino acid sequences located at positions 50 to 54, positions 69 to 86 and positions 118 to 128 in SEQ ID NO: 32, with amino acid sequences located at positions 50 to 54, positions 69 to 86 and positions 118 to 131 in SEQ ID NO: 36, with amino acid sequences located at positions 50 to 54, positions 69 to 86 and positions 118 to 129 in SEQ ID NO: 40 or with amino acid sequences located at positions 50 to 54, positions 69 to 86 and positions 118 to 126 in SEQ ID NO: 44, as heavy chain CDR1, CDR2 and CDR3, respectively; and whose light chain variable region comprises amino acid sequences sharing an identity of at least 80%, 81%, 82%, 83%, 84%, 85%, 86%, 87%, 88%, 89%, 90%, 91%, 92%, 93%, 94%, 95%, 96%, 97%, 98% or 99% with amino acid sequences located at positions 44 to 54, positions 70 to 76 and positions 109 to 116 in SEQ ID NO: 26, with amino acid sequences located at positions 46 to 57, positions 73 to 79 and positions 112 to 119 in SEQ ID NO: 30, with amino acid sequences located at positions 48 to 58, positions 74 to 80 and positions 113 to 120 in SEQ ID NO: 34, with amino acid sequences located at positions 44 to 54, positions 70 to 76 and positions 109 to 116 in SEQ ID NO: 38, with amino acid sequences located at positions 44 to 54, positions 70 to 76 and positions 109 to 116 in SEQ ID NO: 42 or with amino acid sequences located at positions 46 to 57, positions 73 to 79 and positions 112 to 119 in SEQ ID NO: 46, as light chain CDR1, CDR2 and CDR3, respectively.

Moreover, an amino acid sequence sharing a given identity with the amino acid sequence of SEQ ID NO: 24, 26, 28, 30, 32, 34, 36, 38, 40, 42, 44 or 46 may be encoded by a nucleotide sequence sharing a given identity, e.g., an identity of at least 75%, 80%, 81%, 82%, 83%, 84%, 85%, 86%, 87%, 88%, 89%, 90%, 91%, 92%, 93%, 94%, 95%, 96%, 97%, 98% or 99% with the nucleotide sequence of SEQ ID NO: 21, 23, 25, 27, 29, 31, 33, 35, 37, 39, 41, 43 or 45, respectively.

The monoclonal antibody of the present invention having these features is obtained by immunization procedures where cells engineered to express a membrane protein are allowed to be engrafted, as disclosed in WO2010/098471, unlike commonly used procedures for monoclonal antibody preparation. The monoclonal antibody of the present invention is expected to be difficult to prepare by procedures commonly used by those skilled in the art. This is because: (1) when a surfactant is used to prepare a membrane protein for use as an antigen, the membrane protein will lose its three-dimensional structure, whereas when no surfactant is used, aggregation will occur between hydrophobic regions in the membrane protein; and
(2) no immune response is induced because the expression level on the cell surface is low or because the extracellular region is small.

The monoclonal antibody of the present invention has acquired advantageous features over conventional antibodies as a result of inventive modifications made by the inventors of the present invention to procedures for antibody preparation (particularly immunization procedures).

The monoclonal antibody of the present invention has the following features.

The antibody of the present invention can recognize native SLC6A6 because it is prepared based on the three-dimensional structure originally possessed by SLC6A6. For this reason, the antibody of the present invention has very strong binding ability in comparison with a conventional antibody (HPA015028) which recognizes the same epitope, and hence the antibody of the present invention achieves sufficient binding to SLC6A6 on the cell membrane, which has been difficult with conventional antibodies. Moreover, unlike a conventional monoclonal antibody (sc-166640) which recognizes the intramembrane and intracellular regions of SLC6A6, the antibody of the present invention has a recognition site in the extracellular region, and is therefore capable of binding to living cells and can be used as a carrier for therapeutic agents or anticancer agents.

In addition, conventional antibodies are polyclonal antibodies and have been difficult to produce continuously as homogeneous antibodies, whereas the antibody of the present invention is a monoclonal antibody and hence can be mass-produced with high reproducibility. In terms of these features, the antibody of the present invention can be used for cancer treatment.

Moreover, the monoclonal antibody in the present invention is preferably a monoclonal antibody against SLC6A6 produced from the above hybridoma 204, 205, 303, 419, 402, 422 or 430 (hereinafter referred to as 204, 205, 303, 419, 402, 422 or 430 antibody, respectively), with 402 antibody or 430 antibody being particularly preferred. Moreover, the present invention is not limited only to monoclonal antibodies produced from the above hybridomas, and any other antibodies also fall within the monoclonal antibody against SLC6A6 in the present invention as long as they bind to an epitope which is recognized by monoclonal antibodies produced from these hybridomas. As used herein, the term "epitope" refers to an epitope which is recognized by monoclonal antibodies produced from the above hybridomas (i.e., amino acid residues 145 to 213 in the amino acid sequence of SLC6A6, or a partial region thereof).

The monoclonal antibody against SLC6A6 in the present invention may be a chimeric antibody, a humanized antibody or a complete human antibody. A humanized antibody, e.g., a mouse-human chimeric antibody, may be prepared by isolating antibody genes from mouse cells producing an antibody against SLC6A6 protein and causing recombination between its heavy chain (H chain) constant region and human IgG H chain constant region gene, followed by introduction into mouse myeloma cells. On the other hand, a human antibody may be prepared by immunizing the SLC6A6 protein into mice whose immune system has been replaced with the human immune system, as disclosed in WO2010/098471. Moreover, a protein fused with a monoclonal antibody may be prepared using the antigen-binding variable region of the antibody and another protein through existing procedures for gene recombination. Alternatively, it may be prepared by crosslinking the monoclonal antibody and the protein via a crosslinker.

Thus, a human-mouse chimeric antibody of the monoclonal antibody against SLC6A6 produced from the above hybridoma 204, 205, 303, 419, 402, 422 or 430 also falls within the scope of the present invention. For example, human-mouse chimeric antibody 205 comprises a heavy chain comprising the amino acid sequence shown in SEQ ID NO: 24 and a light chain comprising the amino acid sequence shown in SEQ ID NO: 26, human-mouse chimeric antibody 402 comprises a heavy chain comprising the amino acid sequence shown in SEQ ID NO: 28 and a light chain comprising the amino acid sequence shown in SEQ ID NO: 30, human-mouse chimeric antibody 419 comprises a heavy chain comprising the amino acid sequence shown in SEQ ID NO: 32 and a light chain comprising the amino acid sequence shown in SEQ ID NO: 34, human-mouse chimeric antibody 303 comprises a heavy chain comprising the amino acid sequence shown in SEQ ID NO: 36 and a light chain comprising the amino acid sequence shown in SEQ ID NO: 38, human-mouse chimeric antibody 422 comprises a heavy chain comprising the amino acid sequence shown in SEQ ID NO: 40 and a light chain comprising the amino acid sequence shown in SEQ ID NO: 42, and human-mouse chimeric antibody 430 comprises a heavy chain comprising the amino acid sequence shown in SEQ ID NO: 44 and a light chain comprising the amino acid sequence shown in SEQ ID NO: 46. Likewise, such a human-mouse chimeric antibody may be a human-chimeric antibody comprising a heavy chain variable region comprising mouse antibody-derived CDRs and a light chain variable region comprising mouse antibody-derived CDRs.

(2) The Antibody Conjugate of the Present Invention

In another embodiment of the present invention, the monoclonal antibody of the present invention (including an antigen-binding fragment thereof) is conjugated with at least one anticancer agent, toxin or radioisotope. Such a monoclonal antibody of the present invention conjugated with an anticancer agent(s), a toxin(s) or a radioisotope(s) also falls within the scope of the present invention. Moreover, an antibody conjugate comprising the monoclonal antibody of the present invention and at least one anticancer agent, toxin or radioisotope (hereinafter also referred to as the antibody conjugate of the present invention) also falls with the scope of the present invention. The monoclonal antibody of the present invention used in the antibody conjugate of the present invention is preferably, for example, the 204, 205, 303, 419, 402, 422 or 430 antibody or a chimeric antibody thereof, and more preferably the 402 antibody or the 430 antibody or a chimeric antibody thereof.

For example, in yet another embodiment of the present invention, there is provided an antibody conjugate comprising the monoclonal antibody of the present invention and a radioisotope, wherein the monoclonal antibody of the present invention forms a conjugate with a detectable radioisotope. Such a detectable radioisotope may be for example $^{3}H$, $^{14}C$, $^{35}S$, $^{90}Y$, $^{99}Tc$, $^{111}In$, $^{125}I$, $^{131}I$, $^{177}Lu$, $^{166}Ho$ or $^{153}Sm$.

For example, in yet another embodiment of the present invention, there is provided an antibody conjugate comprising the monoclonal antibody of the present invention and an anticancer agent or a toxin, wherein the monoclonal antibody of the present invention forms a conjugate with the anticancer agent or toxin. The above anticancer agent is preferably a chemotherapeutic agent. On the other hand, examples of a toxin include diphtheria toxin, *Pseudomonas* endotoxin and exotoxin, Staphylococcal enterotoxin A, fungal (e.g., α-sarcine, restrictocin), plant (e.g., abrin, ricin, modeccin, viscumin, pokeweed), antiviral proteins, saporin, gelonin, momordin, trichosanthin, barley toxin, *Aleurites fordii* proteins, dianthin proteins, *Phytolacca americana* proteins (PAPI, PAPII and PAP-S), *Momordica charantia* inhibitor, curcin, crotin, *Sapaonaria officinalis* inhibitor, gelonin, mitogellin, restrictocin, phenomycin, neomycin, and trichothecene, etc.

"Chemotherapeutic agents" are chemical compounds useful in cancer treatment, regardless of their mechanism of action. The types of chemotherapeutic agents include, but are not limited to, alkylating agents, antimetabolites, spindle poison plant alkaloids, cytotoxic/antitumor antibiotics, topoisomerase inhibitors, antibodies, photosensitizers and kinase inhibitors. Chemotherapeutic agents include not only compounds used for "targeting therapy" but also compounds used for conventional chemotherapy. Examples of chemotherapeutic agents include erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-MyersSquibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethaneamide, NOLVADEX®, ISTUBAL®, VALODEX®), and doxorubicin (ADRIAMYCIN®), Akti-1/2, HPPD and rapamycin.

Other examples of chemotherapeutic agents include DM1 (N2'-deacetyl-N2'-(3-mercapto-1-oxopropyl)-maytansine), DM4 (N2'-deacetyl-N2'-(4-mercapto-4-methyl-1-oxopentyl)-maytansine), MMAE (Monomethyl auristatin E), oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), SN-38, tipifarnib (ZARNESTRA™, Johnson & Johnson), ABRAXANE™ (cremophor-free), an albumin-modified nanoparticle formulation of paclitaxel (American Pharmaceutical Partners, Schaumberg, vandetanib (rINN, ZD6474, ZACTIMA®, AstraZeneca), chlorambucil, AG1478, AG1571 (SU5271; Sugen), temsirolimus (TORISEL®, Wyeth), pazopanib (GlaxoSmithKline), canfosfamide (TELCYTA®, Telik), thiotepa, and cyclophosphamide (CYTOXAN®, NEOSAR®); alkyl sulfonates such as busulphan, improsulfan and piposulfan; aziridines such as benzodopa, carboquone, meturedopa, and uredopa; ethyleneimines and methylamelamines including altretamine, triethylenemelamine, triethylenephosphoramide, triethylenethiophosphaoramide and trimethylolomelamine; acetogenins (particularly bullatacin and bullatacinone); camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CBI-TM1); eleutherobin; pancratistatin; sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide and uracil mustard; nitrosureas such as carmustine, chlorozotocin, fotemustine, lomustine, nimustine and ranimustine; antibiotics such as enediyne antibiotics (e.g., calicheamicin, calicheamicin gamma 1I and calicheamicin omega I1 (see, e.g., Agnew Chem Intl. Ed. Engl., 33:183-186 (1994)); dynemicin, dynemicinA; bisphosphonates such as clodronate; esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycin, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin and trimetrexate; purine analogs such as fludarabine, 6-mercaptopurine, thiamiprine and thioguanine; pyrimidine analogs such as ancitabine, azacitidine, 6-azauridine, carmofur, cytarabine, dideoxyuridine, doxifluridine, enocitabine and floxuridine; androgens such as calusterone, dromostanolone propionate, epitiostanol, mepitiostane, testolactone; antiadrenal agents such as aminoglutethimide, mitotane and trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilone; etoglucid; gallium nitrate; hydroxyurea; lentinan; lonidamine; maytansinoids such as maytansine and ansamitocin; mitoguazone; mitoxantrone; mopidamol; nitracrine; pentostatin; phenamet; pirarubicin; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); mitoxantrone; vincristine; vinorelbine (NAVELBINE®); navelbine; novantrone; teniposide; edatrexate; daunomycin; aminopterin; capecitabine (XELODA®, Roche); ibandronate; CPT-11; topoisomerase inhibitor RFS2000; difluoromethylornithine (DMFO); retinoids such as retinoic acid; as well as pharmaceutically acceptable salts, acids and derivatives of the above members.

Also included in the definition of "chemotherapeutic agents" are: (i) anti-hormonal agents that act to regulate or inhibit the action of hormones on tumors, e.g., anti-estrogens and selective estrogen receptor modulators (SERMs), as exemplified by tamoxifen (NOLVADEX® tamoxifen citrate), raloxifene, droloxifene, 4-hydroxytamoxifen, trioxifene, keoxifene, LY117018, onapristone and FARESTON® (toremifene citrate); (ii) aromatase inhibitors that inhibit the enzyme aromatase, which regulates estrogen production in the adrenal glands, as exemplified by 4(5)-imidazoles, aminoglutethimide, MEGASE® (megestrol acetate), AROMASIN® (exemestane, Pfizer), formestanie, fadrozole, RIVISOR® (vorozole), FEMARA® (letrozole, Novartis) and ARIMIDEX® (anastrozole, AstraZeneca); (iii) anti-androgens, as exemplified by flutamide, nilutamide, bicalutamide, leuprolide, and goserelin; as well as troxacitabine (a 1,3-dioxolane nucleoside cytosine analog); (iv) protein kinase inhibitors, as exemplified by MEK inhibitors (WO2007/044515); (v) lipid kinase inhibitors; (vi) antisense oligonucleotides, particularly those which inhibit the expression of genes in signaling pathways implicated in aberrant cell proliferation, e.g., PKC-α, Raf and H-Ras, as exemplified by oblimersen (GENASENSE®, Genta Inc.); (vii) ribozymes, as exemplified by VEGF expression inhibitors (e.g., ANGIOZYME®) and HER2 expression inhibitors; (viii) gene therapy vaccines, as exemplified by vaccines such as ALLOVECTIN®, LEUVECTIN® and VAXID®; PROLEUKIN® rIL-2; topoisomerase 1 inhibitors such as LURTOTECAN®; ABARELIX® rmRH; (ix) anti-angiogenic agents, as exemplified by bevacizumab (AVASTIN®, Genentech); as well as pharmaceutically acceptable salts, acids or derivatives of the above members. Also included in the definition of "chemotherapeutic agents" are therapeutic antibodies, as exemplified by alemtuzumab (Campath), bevacizumab (Avastin®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody-drug conjugate, gemutuzumab ozogamicin (MYLOTARG®, Wyeth).

Human monoclonal antibodies or humanized monoclonal antibodies with therapeutic potential as chemotherapeutic agents to be combined with the anti-SLC6A6 monoclonal antibody include alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemutuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab and visilizumab.

In the antibody conjugate of the present invention, a preferred anticancer agent is 5-FU, doxorubicin or SN-38.

A "metabolite" is a product produced through metabolism in the body of a specific compound or salt thereof. Metabolites of a compound may be identified using routine techniques known in the art, and their activity may be determined using tests such as those described herein. Such products may result from, e.g., oxidation, reduction, hydrolysis, amidation, deamidation, esterification, deesterification, enzymatic cleavage and the like, of the administered compound. Thus, the present invention includes metabolites of the compound of the present invention, including compounds produced by a method which involves contacting the compound of the present invention with a mammal for a period of time sufficient to yield metabolites thereof.

For preparation of conjugates, various techniques can be used that are well known to those skilled in the art in the field to which the present invention pertains. For example, a conjugate is prepared by initial modification of reactive moieties on an antibody, such as lysine amino groups, or cysteine groups (which are generated by reduction of native disulfide bonds or by engineering of additional non-native cysteine residues onto the antibody using molecular biological techniques). Alternatively, an antibody is first modified with a heterobifunctional linker reagent, as exemplified by SPDB, SMCC and SIAB (U.S. Pat. No. 6,913,758 and U.S. Patent Publication No. 20050169933), to thereby incorporate a linker having a reactive group such as mixed pyridyldisulfide, maleimide or haloacetamide. The incorporated reactive linker group in the antibody is then conjugated with a cytotoxic agent containing a reactive moiety such as a thiol group. Another conjugation route is by reaction of a cytotoxic agent derivative containing a thiol-reactive group (e.g., haloacetamide or maleimide) with thiol groups on a cell-binding agent. Further, conjugation is also possible through N-succinylimide or maleimide which reacts with amino groups or carboxyl groups on the antibody. Another conjugation route involves reacting an antibody with an oxidant to form an aldehyde-bearing antibody, reacting the aldehyde-bearing antibody with a PEG maleimide/hydrazide bifunctional linker to form a thiol-reactive antibody, and reacting the thiol-reactive antibody with a thiolated signal-generating moiety to form an antibody-signal-generating moiety conjugate. In a specific embodiment, reacting an antibody with an oxidant to form an aldehyde-bearing antibody comprises oxidizing a glycosylated region of the antibody (with periodate, bromine or iodine) to form the aldehyde-bearing antibody.

The monoclonal antibody of the present invention may be directly or indirectly linked (conjugated) with an anticancer agent, a toxin or a radioisotope. Indirect conjugation includes conjugation via a linker and conjugation via an antibody or an antibody fragment, which binds to the monoclonal antibody of the present invention. For example, an antibody conjugate formed by binding between an antibody conjugated with a labeling substance (e.g., a fluorescent label) and the monoclonal antibody of the present invention also falls within the present invention.

2. The Pharmaceutical Composition of the Present Invention

In the present invention, there is provided a pharmaceutical composition comprising the monoclonal antibody of the present invention (including an antigen-binding fragment thereof). In this pharmaceutical composition, the monoclonal antibody of the present invention is conjugated with an anticancer agent, a toxin or a radioisotope, as described above. Thus, in yet another embodiment of the present invention, there is provided a pharmaceutical composition comprising the antibody conjugate of the present invention.

The monoclonal antibody of the present invention recognizes SLC6A6 expressed in cancer cells and is internalized after binding to SLC6A6. For this reason, the pharmaceutical composition of the present invention comprising the monoclonal antibody of the present invention (including an antibody conjugate thereof) is useful as a pharmaceutical composition for cancer treatment, preferably as a pharmaceutical composition for colorectal cancer treatment.

Moreover, the pharmaceutical composition of the present invention may also be used as a therapeutic agent for cancer. The therapeutic agent for cancer intended in the present invention comprises an SLC6A6 antibody conjugated with an anticancer agent, a toxin or a radioisotope or an antibody conjugate, or alternatively, comprises an SLC6A6 antibody optionally combined with a pharmaceutically acceptable anticancer agent or carrier, as appropriate. Alternatively, the therapeutic agent for cancer intended in the present invention may be used in combination with other modes of therapy.

Moreover, the monoclonal antibody of the present invention not only recognizes SLC6A6 expressed in cancer cells, but is also taken up into the cells through the mechanism of internalization after binding to SLC6A6 on the cell membrane. Thus, the pharmaceutical composition of the present invention can be used for killing cancer cells expressing SLC6A6 and/or for labeling cancer cells with a radioisotope.

In particular, in the case of comprising an antibody conjugate comprising a chemotherapeutic agent and the monoclonal antibody of the present invention, the chemotherapeutic agent conjugated with the antibody can also be taken up into cancer cells, so that the pharmaceutical composition of the present invention is useful for killing cancer cells in a cancer patient.

In the present invention, cancer treatment includes killing cancer cells, reducing the size of cancer, suppressing or arresting the rate of cancer growth, or suppressing or arresting the progression of cancer, by way of example.

The pharmaceutical composition of the present invention may further comprise at least one anticancer agent. As an anticancer agent to be used in combination, the same chemotherapeutic agent as that contained in the pharmaceutical composition of the present invention may be used, or alternatively, a different chemotherapeutic agent may be used. The dose and mode of administration of such an anticancer agent may be determined as appropriate by those skilled in the art.

The pharmaceutical composition of the present invention may be administered to any type of cancer where SLC6A6 is expressed, and examples include malignant melanoma, malignant lymphoma, digestive organ cancer, lung cancer, esophageal cancer, gastric cancer, colorectal cancer, rectal cancer, colon cancer, urinary tract tumor, gallbladder cancer, bile duct cancer, biliary tract cancer, breast cancer, liver cancer, pancreatic cancer, testicular tumor, maxillary cancer, tongue cancer, lip cancer, oral cancer, pharyngeal cancer, laryngeal cancer, renal cancer, ovarian cancer, uterine cancer, prostate cancer, thyroid cancer, brain tumor, Kaposi's sarcoma, angioma, leukemia, polycythemia vera, neuroblastoma, retinoblastoma, myeloma, urinary bladder tumor, sarcoma, osteosarcoma, myosarcoma, skin cancer, basal cell carcinoma, skin appendage carcinoma, skin metastatic cancer, skin melanoma and so on. Preferred are colorectal cancer, gastric cancer, bladder cancer, renal cancer, uterine cancer and breast cancer, and more preferred are colorectal cancer, breast cancer and uterine cancer.

The pharmaceutical composition of the present invention may be administered in any mode, including oral administration, parenteral administration (e.g., subcutaneous administration, intracutaneous administration, mucosal administration, intrarectal administration, intravaginal administration, topical administration to the affected area, dermal administration), or direct administration to the affected area, etc.

The dose of the pharmaceutical composition of the present invention may generally be determined as appropriate for the age and body weight of a subject (patient) to be administered, the type and progression of disease, the route of administration, the frequency of administration, the period of administration, etc., in consideration of the mixing ratio of the active ingredient in the formulation. Such an active ingredient may be exemplified by an anticancer agent, a toxin or a radioisotope, which is to be conjugated with the monoclonal antibody of the present invention, etc.

Detailed explanation will be given below for the case where the pharmaceutical composition of the present invention is used as a parenteral formulation.

For use as a parenteral formulation, the pharmaceutical composition of the present invention may usually be formulated into any dosage form, such as intravenous injections (including drip infusions), intramuscular injections, intraperitoneal injections, subcutaneous injections, suppositories, etc.

In the case of various types of injections, for example, they may be provided in the form of unit dose ampules or multi-dose containers or as freeze-dried powders which are dissolved again in a diluent before use. Such a parenteral formulation may comprise not only the active ingredient mentioned above, but also various known excipients and/or additives as appropriate for each dosage form as long as the effect of the above active ingredient is not impaired. In the case of various types of injections, examples of excipients and/or additives include water, glycerol, propylene glycol, and aliphatic polyalcohols such as polyethylene glycol, etc.

The dose (daily dose) of such a parenteral formulation is not limited in any way. For example in the case of various types of injections, the above active ingredient (antibody) is generally used at a dose of preferably 1 to 15 mg/day, more preferably 2 to 12 mg/day, per kg body weight of a subject (patient) to be applied.

For use as an oral formulation, the pharmaceutical composition of the present invention may usually be formulated into any dosage form, such as tablets, capsules, granules, powders, pills, troches, solutions for internal use, suspensions, emulsions, syrups, etc., or may be formulated into a dried product which is dissolved again before use.

The pharmaceutical composition of the present invention may optionally comprise pharmaceutically acceptable additives. Specific examples of pharmaceutically acceptable additives include, but are not limited to, antioxidants, preservatives, colorants, flavors, diluents, emulsifiers, suspending agents, solvents, fillers, extenders, buffering agents, delivery vehicles, diluents, carriers, excipients and/or pharmaceutical adjuvants, etc.

The present invention provides a kit comprising the monoclonal antibody of the present invention for use in treatment of cancer, e.g., colorectal cancer. The kit of the present invention has no particular limitation on its constituent materials as long as it comprises the monoclonal antibody of the present invention conjugated with an anticancer agent, a toxin or a radioisotope. In addition to the monoclonal antibody of the present invention conjugated with an anticancer agent, a toxin or a radioisotope, the kit of the present invention may further comprise water, a buffer, a container, a syringe, an instruction manual and so on. The monoclonal antibody of the present invention is provided, e.g., in an aqueous solution state or in a lyophilized state, and may be reconstituted into an appropriate state before use. Moreover, the kit of the present invention may comprise at least one additional anticancer agent. The use of the kit of the present invention allows effective treatment of cancer.

Moreover, the present invention also provides a therapeutic method for cancer, which comprises administering the monoclonal antibody of the present invention to a subject. In the therapeutic method of the present invention, the monoclonal antibody of the present invention forms a conjugate with an anticancer agent, a toxin or a radioisotope. Namely, the therapeutic method of the present invention may comprise administering the antibody conjugate of the present invention to a subject. Moreover, in the therapeutic method for cancer of the present invention, an additional anticancer agent(s) may be used in combination. Further, the present invention includes the monoclonal antibody of the present invention for use in cancer treatment, wherein the monoclonal antibody of the present invention is conjugated with an anticancer agent, a toxin or a radioisotope. Moreover, the present invention also includes the conjugate of the present invention for use in cancer treatment.

EXAMPLES

The present invention will be further described in more detail by way of the following examples, although the present invention is not limited only to these examples.

Example 1

Obtaining of Anti-SLC6A6 Monoclonal Antibodies
(1) Cells

In the Example section of the present application, DLD-1, HCT116, Colo320 and WiDr were obtained from DS Pharma. Caco-2, COLO201, HCT15, HT-29, LOVO, SW480, SW620, 293T and MDA-MB231 were obtained from American Type Culture Collection (ATCC Accession No. HTB-26).

Culture and subculture were conducted at 37° C. under 5% $CO_2$ for 48 to 72 hours in RPMI 1640 medium (Sigma) containing 10% (v/v) serum (Hyclone) for MDA-MB231, SW620, DLD-1, Colo201 and Colo320, in E-MEM medium (Sigma) for WiDr, in McCoy's5A medium (Sigma) for HCT116, and in DMEM medium (Sigma) for HT-29, LoVo, SW480, 293T and the other cells, such that cell confluency did not exceed 80% in each case.

(2) Cells for Immunization

In the same manner as shown in Example 2 of WO2012/029990, the human SLC6A6 gene was integrated into pEF6 vector to thereby prepare an expression vector. This SLC6A6 expression vector was transformed into MDA-MB231 using FUGENE6 (Roche). Operations were conducted as described in the manufacturer's instructions attached to this kit. The cells were cultured in the medium supplemented with blasticidin S hydrochloride at 10 μg/mL, and the medium was replaced every 3 to 5 days to select drug-resistant cells. For selection of SLC6A6-overexpressing cells from among the resulting resistant strains, the non-transformed cells and the transformed cells were each seeded in 96-well plates at 80% confluency and cultured at 37° C. under 5% $CO_2$ for 16 hours.

After removing the culture supernatant from each well, a 10% (v/v) neutral buffered formalin solution (WAKO) was added in 100 μL volumes and reacted for 10 minutes at room temperature. After removing the formalin solution, the plates were washed three times with PBS(−) and then air-dried to thereby prepare cell-immobilized plates for the respective cases.

Anti-c-myc antibody (santa cruz, clone 9E10) was diluted to 1 μg/mL with TBS-T (25 mM Tris, 150 mM NaCl, 0.05% (v/v) Tween 20, pH 7.4) and added as a primary antibody to the immobilized plates in a volume of 100 μL per well, followed by reaction at room temperature for 1 hour. Each well was washed three times with 200 μL of TBS-T.

For use as a secondary antibody, anti-mouse IgG polyclonal antibody-HRP label (BETHYL) was diluted 5000-fold with TBS-T. The above antibody dilution was added in a volume of 100 μL per well and reacted at room temperature for 30 minutes. Each well was washed three times with 200 μL of TBS-T.

Orthophenylenediamine (Sigma) was diluted with 20 mM phosphate-citrate buffer (pH 5.0) to give a final concentration of 0.5 mg/mL and mixed with 1/2,000 volumes of 35% (w/w) aqueous hydrogen peroxide (WAKO). The resulting mixture was added as a substrate solution in a volume of 100 μL per well and reacted at room temperature for 10 minutes. 25 μL of 3 N sulfuric acid (WAKO) was added to stop the reaction. The absorbance at 492 nm was measured with a plate reader (SpectraMaxPure 384, Molecular Devices) to observe signals, thereby selecting strains showing higher signals than non-transformed MDA-MB231. Clones showing the highest expression were used as cells for immunization.

(3) Transplantation of Cells

Cells cultured in a 10 cm dish to reach 90% confluency were collected with trypsin (GIBCO) and washed twice with PBS(—) (0.01 M sodium-phosphate buffer, 0.138 M NaCl, 0.0027 M KCl, pH 7.4). The washed cells were suspended in growth factor reduced Matrigel (Becton Dickinson) to give a final density of $8.6 \times 10^7$ cells/mL and stored on ice until use for transplantation.

Chloral hydrate (Sigma) was dissolved at a concentration of 3.5% (w/v) in physiological saline to prepare a 3.5% solution of chloral hydrate in physiological saline. Nude mice at 6 to 8 weeks of age (BALB/cALcl-nu/nu line (CLEA Japan, Inc., Japan)) were anesthetized by being intraperitoneally administered with 0.2 mL of the 3.5% solution of chloral hydrate in physiological saline. Into the fourth mammary glands in each mouse, the cells suspended in the Matrigel were transplanted at $1 \times 10^6$ cells per mammary gland via a 24 G injection needle, such that the cells did not extend off the mammary gland. Each mouse received two transplantations, one at left and another at right fourth mammary gland in the trunk.

(4) Expression and Purification of SLC6A6 Partial Protein for Screening

From the full-length gene for SLC6A6 introduced into pEF6 vector in Example 1(2), DNA (SEQ ID NO: 3) encoding a region covering amino acid residues 143 to 216 (SEQ ID NO: 4) in the extracellular region was subcloned into pET32 vector. The following primers were used for PCR.

```
Primer sequences
Forward:
                                 (SEQ ID NO: 5)
ATAGGATCCGGCCTGGGCCACATACTACCTG Reverse:
                                 (SEQ ID NO: 6)
TATGAATTCGCTTTCAGAGAGCCTGGGTGGTC
```

The PCR reaction was accomplished by preincubation at 94° C. for 2 minutes and subsequent 30 cycles of denaturation at 98° C. for 10 seconds, annealing at 58° C. for 30 seconds and elongation at 68° C. for 30 seconds to amplify a gene fragment. The resulting amplified fragment was integrated into pET32 vector (Novagen) by means of the restriction enzymes (EcoRI and BamHI) located on the primers.

The amplified fragment was confirmed for its nucleotide sequence by DNA sequencing, indicating that the same extracellular region gene sequence as found in the database was integrated and a His tag sequence was added to the C-terminal end.

BL21(DE3) (Invitrogen) was transformed with this vector and cultured in LB medium (1% (w/v) tryptone (Sigma), 0.5% (w/v) yeast extract (Sigma), 0.5% (w/v) NaCl (Sigma)) supplemented with 1% (w/v) glucose. After the medium turbidity reached 0.6 at a wavelength of 600 nm, 1 mM IPTG (WAKO) was added and culture was continued for 16 hours. The microbial cells were collected by centrifugation and then homogenized by ultrasonication to obtain a fraction containing the extracellular region of SLC6A6 as an insoluble protein.

About 10 mg of the sample was dissolved in Buffer A (1 M guanidine hydrochloride (Sigma), 10 mM DTT (Sigma), 10 mM EDTA (Sigma)) and reacted at 37° C. for 1 hour. The reacted product was gently added to 1 L of Buffer B (50 mM Tris, 150 mM NaCl, 5% glycerol, 0.4 mM oxidized glutathione (Sigma), pH 8.5), followed by stirring at 4° C. for 18 hours. The dissolved sample was applied to a Ni sepharose column (GE) and eluted with Buffer C (50 mM potassium phosphate buffer, 150 mM NaCl, 200 mM imidazole, pH 8.0), followed by dialysis against imidazole-free Buffer C to obtain a partial protein of the extracellular region of SLC6A6 in a purified state.

(5) Antiserum Analysis

The recombinant protein obtained in (4) above (10 μg/ml) was dispensed in 100 μL volumes into MaxiSorp 96-well plates (Nunc) and adsorbed onto the plates at room temperature for 1 hour. After adsorption, each well was washed with TBS-T (TBS-T (25 mM Tris, 150 mM NaCl, 0.05% (v/v) Tween 20, pH 7.4) and charged with skimmed milk (GIBCO), which had been diluted to 5% with TBS-T, to conduct blocking for 30 minutes at room temperature. After each well was washed three times with 200 μL of TBS-T, mouse plasma samples collected from the tail vein were each diluted 1/2000-fold with TBS-T and added to the ELISA plates in a volume of 100 μL per well, followed by reaction at room temperature for 1 hour. Each well was washed three times with 200 μL of TBS-T.

For use as a secondary antibody, anti-mouse IgG polyclonal antibody-HRP label (BETHYL) was diluted 5000-fold with TBS-T. The above antibody dilution was added in a volume of 100 μL per well and reacted at room temperature for 30 minutes. Each well was washed three times with 200 μL of TBS-T.

Orthophenylenediamine (Sigma) was diluted with 20 mM carbonate-citrate buffer (pH 5.0) to give a final concentration of 0.5 mg/mL and mixed with 1/2000 volumes of 35% (w/w) aqueous hydrogen peroxide (WAKO). The resulting mixture was added as a substrate solution in a volume of 100 μL per well and reacted at room temperature for 10 minutes. 25 μL of 3 N sulfuric acid (WAKO) was added to stop the reaction. The absorbance at 492 nm was measured with a plate reader (SpectraMaxPure 384, Molecular Devices) to analyze antibody titers, which were then used for selection of mice to be used for cell fusion.

(6) Cell Fusion

Mouse spleen lymphocytes were electrically fused with mouse myeloma cell line P3X63-Ag8 (ATCC Accession No. CRL-1580). For cell fusion, $1 \times 10^8$ spleen cells were mixed with $0.25 \times 10^8$ cells of the myeloma cell line and suspended in EP Buffer (0.3 M mannitol, 0.1 mM $CaCl_2$, 0.1 mM $MgCl_2$) to give a cell density of $0.25 \times 10^8$ cells/mL, followed by cell fusion with an electro cell fusion generator LF201 (Nepa Gene Co., Ltd., Japan). Fusion conditions were set in accordance with the manufacturer's recommended protocols.

The fused cells were suspended in HAT medium (Invitrogen) and dispensed into thirty 96-well plates in a volume of 100 μL per well. During culture, 200 μL, of HAT medium was added to each well. After culture for 11 to 16 days, the plates were observed under a microscope, indicating that 5 to 12 colonies were formed per well.

(7) Obtaining of Monoclonal Antibodies

At 3 to 7 months after transplantation, spleen cells were collected from the mice and used to prepare hybridoma cells in the same manner as shown in (6) above. For selection of antibodies recognizing SLC6A6, the same procedure as shown in (5) above was used to select clones. As a primary antibody, the culture supernatant of each hybridoma was used. For use as a secondary antibody, anti-mouse IgG1 polyclonal antibody-HRP label, anti-mouse IgG2a polyclonal antibody-HRP label and anti-mouse IgG2b polyclonal antibody-HRP label (Bethyl) were mixed together in equal amounts and diluted 100000-fold with TBST to ensure that only clones of subclass IgG were detected. In this way, hybridomas producing desired antibodies were selected.

The thus obtained monoclonal antibody-producing hybridoma cells were cultured in ten 10 cm dishes to reach 90% confluency and then cultured for 10 days in a 1:1 mixture of HT medium (Invitrogen) and EX CELL Sp2/0 (Nichirei Bioscience Inc., Japan). The culture supernatants were collected and purified with a Protein G column. The Protein G column (GE Healthcare) was used in a volume of 0.5 mL relative to 100 mL of the culture supernatant. The cultured solutions were each passed at a flow rate of 1 to 3 ml/min through the Protein G column which had been equilibrated with PBS(−), followed by washing with 6 mL of washing buffer (25 mM Tris-HCl (pH 7.4), 140 mM NaCl, 10 mM KCl). Then, antibody proteins were eluted with 1 mL of elution buffer (0.1 M glycine-HCl (pH 2.5) or 0.1 M glycine-HCl (pH 3.0)) and neutralized with 0.5 M Tris-HCl (pH 7.4) to be within pH 7.0 to 7.4. The antibodies were concentrated with Amicon Ultra 30 (Millipore) and the buffer was replaced with PBS(−). The antibody clones obtained from the resulting seven hybridoma clones and the anti-SLC6A6 antibodies "4B9b" and "5H12d" disclosed in WO2012/029990 are summarized in Table 1 below for their subclass and their results of ELISA measured in the same manner as shown in (5) above.

TABLE 1

| Antibody No. | Subclass | ELISA reactivity |
|---|---|---|
| 204 | IgG2a | ++++ |
| 205 | IgG2b | +++ |
| 303 | IgG2a | +++ |
| 419 | IgG2a | +++ |
| 402 | IgG2a | + |
| 422 | IgG1 | + |
| 430 | IgG2a | + |
| 4B9h | IgM | ++ |
| 5H12d | IgM | ++ |

The hybridoma "4B9b" producing the antibody "4B9b" was internationally deposited under Accession No. "FERM BP-11413" by Bio Matrix Research Inc. (105 Higashifukai, Nagareyama-shi, Chiba 270-0101, Japan) on Jul. 21, 2010 with the International Patent Organism Depositary, the National Institute of Advanced Industrial Science and Technology in Japan (Central 6, 1-1-1 Higashi, Tsukuba-shi, Ibaraki 305-8566, Japan) under the Budapest Treaty. Likewise, the hybridoma "5H12d" producing the antibody "5H12d" was internationally deposited under Accession No. "FERM BP-11414" by Bio Matrix Research Inc. (105 Higashifukai, Nagareyama-shi, Chiba 270-0101, Japan) on Jul. 21, 2010 with the International Patent Organism Depositary, the National Institute of Advanced Industrial Science and Technology in Japan (Central 6, 1-1-1 Higashi, Tsukuba-shi, Ibaraki 305-8566, Japan) under the Budapest Treaty (the above date in each hybridoma represents its initial deposit date). For expression of mouse IgG-converted antibody "4B9b," an H chain expression vector and an L chain expression vector were obtained as described in PCT/JP2013/56884 and used for this purpose. For expression of human IgG-converted "mouse-human chimeric 4B9b antibody," an H chain expression vector and an L chain expression vector were obtained as described in PCT/JP2013/56884 and used for this purpose.

(8) Immunocytological Staining

The seven types of antibody clones "204," "205," "303," "419," "402," "422" and "430" obtained in (7) above were analyzed for their reactivity to colorectal cancer cells (HT-29 and LoVo). Moreover, as controls for comparison purposes, the anti-SLC6A6 antibodies "4B9b" and "5H12d" disclosed in WO2012/029990 were also analyzed in the same manner. Hereinafter, antibodies produced by hybridoma cells are also represented by their respective clone numbers.

HT-29 and LoVo cells were cultured to reach 80% confluency and then seeded onto cover slips coated with Cell-matrix Type I-A (Nitta Gelatin Inc., Japan). After culture for 2 days, the cells were fixed with 10% neutral buffered formalin (WAKO). After being treated with 0.3% (v/v) aqueous hydrogen peroxide for 20 minutes, the cover slips were washed three times with TBST and treated with TBST containing 5% (w/v) skimmed milk, followed by addition of the antibodies purified in (7) above at a concentration of 10 μg/mL and reaction at 4° C. for 16 hours. After washing three times with TBST, anti-mouse IgG polyclonal antibody-Alexa Fluor 488 label or anti-mouse IgM polyclonal antibody-Alexa Fluor 488 label was reacted as a secondary antibody at room temperature for 30 minutes. After washing three times with TBST, the cover slips were sealed with Mounting Medium (Vector Shield).

FIG. 1 shows the results analyzed for the fluorescence intensity of each antibody under the same conditions. Signals were observed in all the clones (204, 205, 303, 419, 402, 422 and 430), and signals were clearly observed particularly in the clones 204, 205, 303, 419 and 402. When compared to antibodies of subclass IgM such as 4B9b and 5H12d, the clone 205, 303 and 419 antibodies were found to result in significantly higher signals and therefore have higher affinity. In this example, clones having higher titers than conventional SLC6A6 antibodies were able to be obtained.

Example 2

(1) FACS Analysis 293T cells (which are human fetal renal cells) were cultured to reach 90% confluency. After being washed twice with PBS(−), the cells were detached with a scraper and collected into 1.5 mL tubes. The 204, 205 and 419 antibodies were each added to the tubes at a final concentration of 10 μg/mL, followed by reaction for 60 minutes. As a control for comparison purposes, 4B9b was added at the same concentration, followed by reaction. After the cells were washed twice with PBS(−) supplemented with 2% FBS (PBS+2% FBS), Alexa Fluor 488-labeled goat-anti-mouse IgG (Invitrogen) was added as a 1/1000 dilution in PBS+2% FBS, followed by reaction for 30 minutes. After being washed twice with PBS+2% FBS, the cells were analyzed by FACS Verse (BD). The results obtained are shown in FIG. 2.

Figure 2:
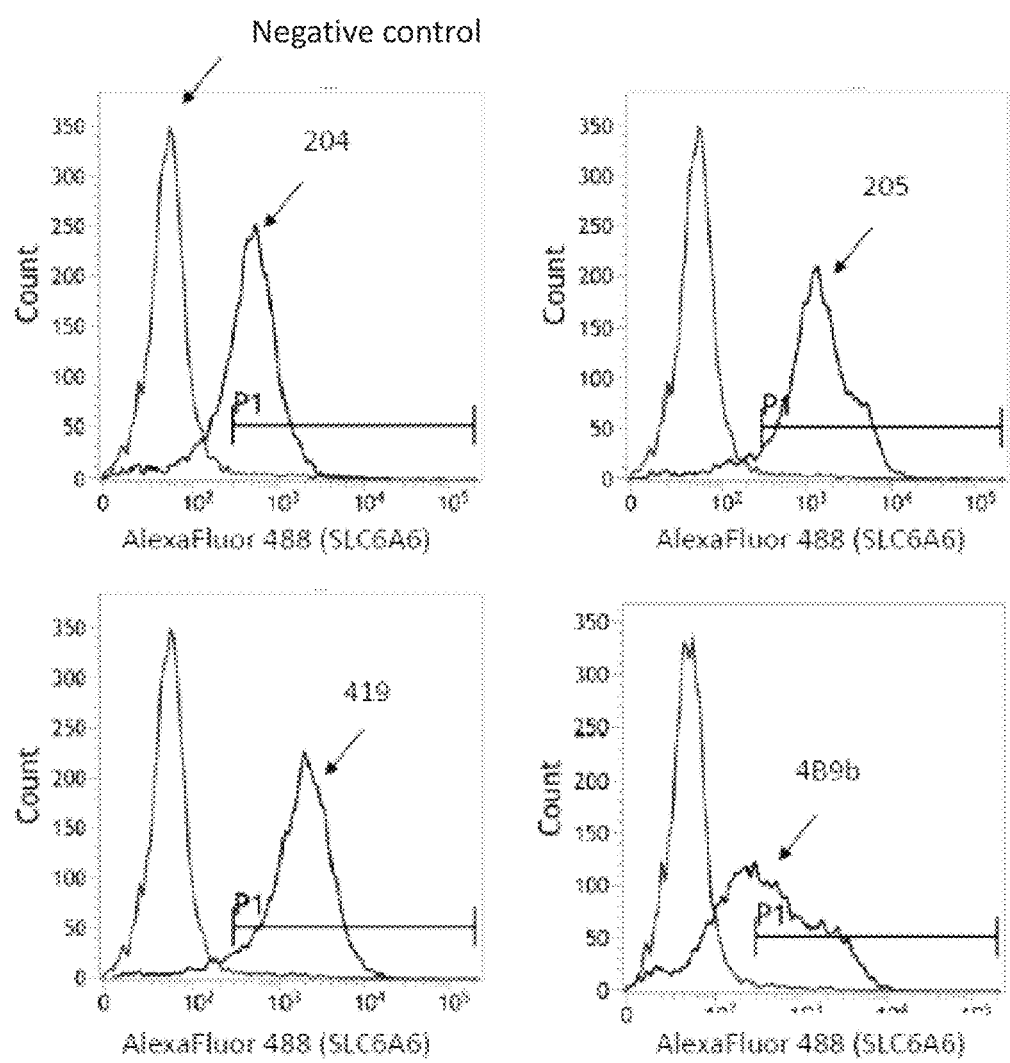
FIG. 2 shows the results analyzed for the activity of monoclonal antibodies produced from hybridoma cells, as measured by FACS using human renal epithelial cells (293T cells).

As can be seen from FIG. 2, the 204, 205 and 419 antibodies were found to more strongly react with 293T cells than 4B9b. Since 293T cells express SLC6A6, it is indicated that the SLC6A6 antibodies of the present invention recognize SLC6A6 in its native structure. Moreover, it is also indicated that the SLC6A6 antibodies of the present invention are able to bind to native SLC6A6 with higher affinity than the conventional SLC6A6 antibody.

Example 3

FACS Analysis

The monoclonal antibodies obtained in Example 1(7), i.e., the antibody clone 204, 205, 303, 419, 402, 422 and 430 antibodies were analyzed for their reactivity to HCT116 cells (which are human colorectal cancer cells) in the same manner as shown in Example 2. The results obtained are shown in FIG. 3.

Figure 3:
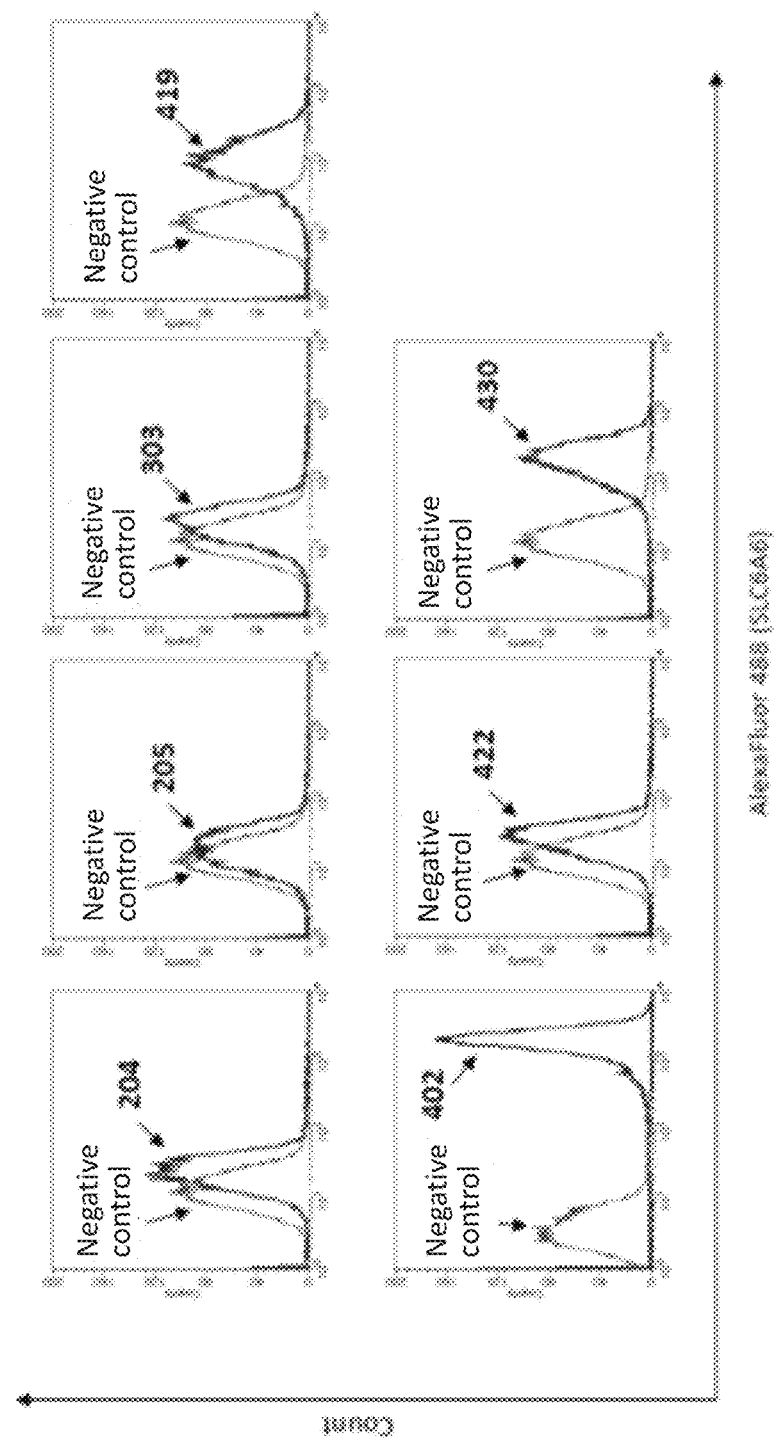
FIG. 3 shows the FACS analysis of antibody clones 204, 205, 303, 419, 402, 422 and 430 using colorectal cancer cells (HCT116).

As can be seen from FIG. 3, the antibody clone 204, 205, 303, 419, 402, 422 and 430 antibodies were found to accurately react with human colorectal cancer cells HCT116.

The antibody clone 205, 419, 402 and 430 antibodies were analyzed for their reactivity to SW480 and HT-29 cells (which are human colorectal cancer cells) in the same manner as shown in Example 2. The results obtained are shown in FIG. 4.

Figure 4:
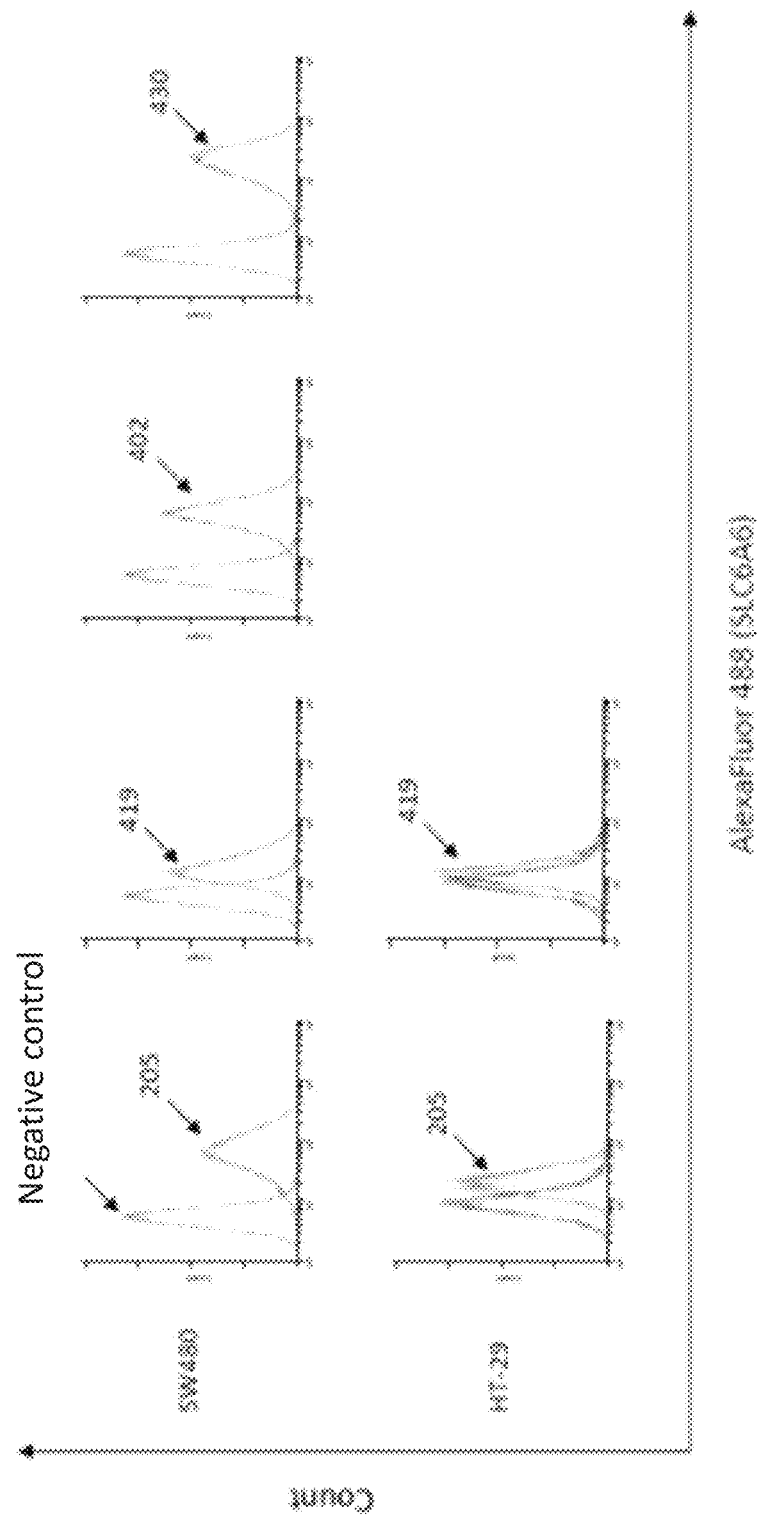
FIG. 4 shows the FACS analysis of antibody clones 205, 419, 402 and 430 using two lines of colorectal cancer cells (SW480 and HT-29).

As can be seen from FIG. 4, the antibody clone 205, 419, 402 and 430 antibodies were also found to accurately react with these two types of cell lines.

In a case where a monoclonal antibody is used as ADC, which is a conjugate with an anticancer agent, a toxin, a radioisotope or the like, an antibody more strongly recognizing the native structure of a protein is preferred for this purpose. This is because cells are alive in cancer tissues and therefore SLC6A6 expressed by cancer cells also retains its native structure. Namely, FACS analysis in Example 3 will be more suitable than the procedure shown in Example 1(5) or 1(8) for the purpose of selecting an antibody clone suitable for use as ADC.

Example 4

(1) Immunohistological Staining 51 cases of colorectal cancer tissue and 8 cases of normal colorectal mucosa were immunohistologically stained with the mouse antibody (clone 205). Paraffin-embedded slices of human colorectal cancer tissues (US Biomax) were deparaffinized with xylene and rehydrated with ethanol. After being treated with 0.3% (v/v) aqueous hydrogen peroxide for 20 minutes, the resulting tissue slices were washed three times with TBST and treated with 1 mg/mL Proteinase K at 37° C. for 15 minutes to activate antigens. Using a Histofine SAB-PO universal kit (Nichirei Corporation, Japan), staining was conducted in accordance with the protocols attached thereto. For primary antibody reaction, 10 µg/mL of the 205 antibody was added and reacted at 37° C. for 1 hour. For color development, ImmPACT DAB Substrate (Vector) was added to cause color development for 5 minutes. After washing with distilled water, nuclei were stained with Hematoxylin (WAKO), and the slices were washed with running water, treated sequentially with ethanol and xylene, and then sealed.

Figure 5:
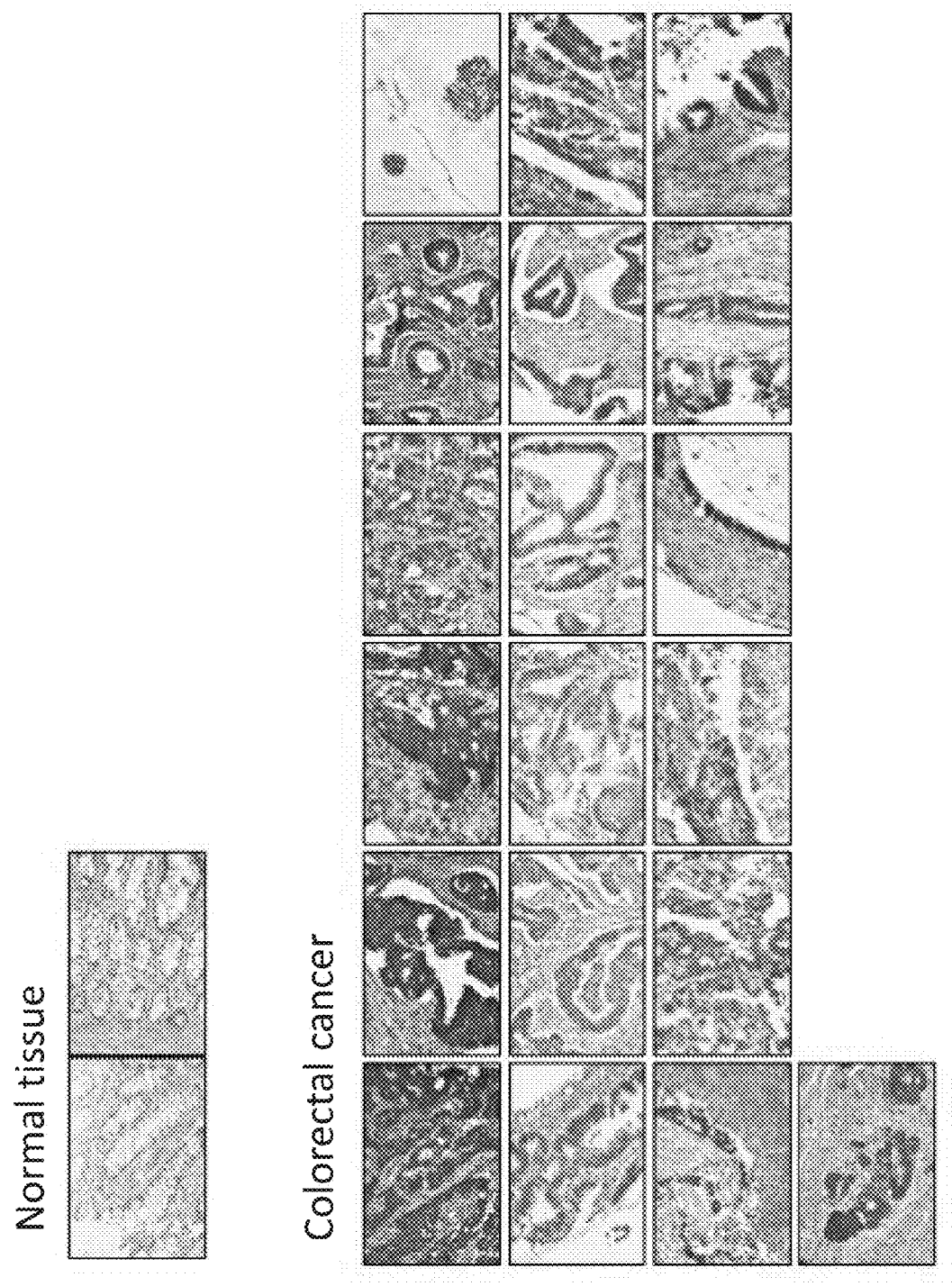
FIG. 5 shows the results (typical examples) of immunohistological staining with anti-SLC6A6 monoclonal antibody (antibody clone 419) in 51 cases of colorectal cancer tissue (Colorectal cancer) and 8 cases of normal colorectal mucosa (Normal tissue).

FIG. 5 shows the results (typical examples) of staining performed on colorectal cancer tissues (Colorectal cancer) and normal tissues (Normal tissue). The stained images were expressed as follows: +++ for strongly positive images; ++ for positive images; + for weakly positive images distinguishable from normal tissue; and − for non-stained images or normal tissue. It should be noted that undetermined cases were expressed as +/−. In the colorectal cancer tissues, when combining the weakly positive, positive and strongly positive cases all together, about 84% (43 cases) were stained with the SLC6A6 antibody of the present invention. In Table 2, the samples used in Example 4 are summarized for their origin and results.

TABLE 2

| No. | Age | Sex | Organ | Diagnosis | pTNM | Stage | Months* | SLC6A6 |
|---|---|---|---|---|---|---|---|---|
| 1 | 67 | M | Descending colon | mucinous adenocarcinoma | T3N2bM0 | III C | — | ++ |
| 2 | 60 | M | Rectum | adenocarcinoma, moderately differentiated | T3N0M0 | II A | — | +/− |
| 3 | 59 | M | Sigmoid colon | adenocarcinoma, well differenciated | T3N0M0 | II A | — | ++ |
| 4 | 58 | F | Rectum | adenocarcinoma, moderately differentiated | T3N2bM0 | III C | — | + |
| 5 | 64 | M | Rectum | adenocarcinoma, moderately differentiated | T3N2aM0 | III B | — | + |
| 6 | 31 | M | Rectum | mucinous adenocarcinoma | T3N2bM0 | III C | — | + |
| 7 | 47 | F | Rectum | adenocarcinoma, well differenciated | T3N1M0 | III B | — | fall off |
| 8 | 46 | F | Rectum | adenocarcinoma, well differenciated | T3N0M0 | II A | — | +/− |
| 9 | 64 | M | Sigmoid colon | adenocarcinoma, well differenciated | T3N1aM0 | III B | — | − |
| 10 | 64 | F | Rectum | adenocarcinoma, moderately differentiated | T2N0M0 | I | — | + |
| 11 | 30 | M | Rectum | adenocarcinoma | T3N1bM0 | III B | — | ++ |
| 12 | 51 | M | Ascending colon | adenocarcinoma, moderately differentiated | T3N0M0 | II A | — | + |
| 13 | 67 | M | Cecum | adenocarcinoma, well differenciated | T3N0M0 | II A | — | ++ |
| 14 | 38 | M | Rectum | adenocarcinoma, well differenciated | T3N0M1a | IV A | — | ++ |
| 15 | 71 | F | Descending colon | mucinous adenocarcinoma | T3N0M0 | II A | — | ++ |
| 16 | 52 | M | Rectum | adenocarcinoma, well differenciated | T4aN0M0 | II B | — | ++ |
| 17 | 63 | M | Transverse colon | adenocarcinoma, moderately differentiated | T3N1bM0 | III B | — | + |
| 18 | 62 | M | Descending colon | adenocarcinoma, moderately differentiated | T3N0M0 | II A | — | + |
| 19 | 60 | M | Sigmoid colon | adenocarcinoma, moderately differentiated | T3N0M0 | II A | — | ++ |
| 20 | 72 | M | Transverse colon | adenocarcinoma, moderately differentiated | T3N2bM0 | III C | — | ++ |
| 21 | 67 | M | Sigmoid colon | adenocarcinoma, moderately differentiated | T3N1bM0 | III B | — | + |
| 22 | 71 | M | Sigmoid colon | adenocarcinoma, moderately differentiated | T4aN2aM0 | III C | — | + |
| 23 | 72 | M | Rectum | adenocarcinoma, well differenciated | T2N0M0 | I | — | + |
| 24 | 68 | M | Ascending colon | mucinous carcinoma | T4aN1bM0 | III B | — | ++ |
| 25 | 54 | M | Ascending colon | adenocarcinoma, poorly differentiated | T3N2bM0 | III C | — | ++ |
| 26 | 57 | M | Sigmoid colon | adenocarcinoma, moderately differentiated | T3N0M0 | II A | — | − |
| 27 | 56 | F | Sigmoid colon | adenocarcinoma, moderately differentiated | T3N2aM0 | III B | — | ++ |
| 28 | 58 | M | Rectum | adenocarcinoma, moderately differentiated | T3N0M0 | II A | — | + |
| 29 | uk | F | Descending colon | adenocarcinoma, well differenciated | T3N1bM1a | IV A | — | + |
| 30 | 41 | F | Sigmoid colon | adenocarcinoma, well differenciated | T3N2aM1b | IV B | — | ++ |
| 31 | 52 | M | Rectum | adenocarcinoma, moderately differentiated | T3N1aM1a | IV A | — | + |
| 32 | 46 | F | Ascending colon | adenocarcinoma, poorly differentiated | T3N2bM0 | III C | — | +/− |
| 33 | 44 | M | Rectum | adenocarcinoma, moderately differentiated | T3N2aM1a | IV A | — | +/− |
| 34 | 47 | F | Sigmoid colon | adenocarcinoma, moderately differentiated | T3N1bM1b | IV B | — | + |
| 35 | 60 | M | Sigmoid colon | adenocarcinoma, moderately differentiated | T3N0M1a | IV A | — | + |
| 36 | 53 | M | Ascending colon | adenocarcinoma, poorly differentiated | T3N1bM1a | IV A | — | + |
| 37 | 39 | F | Sigmoid colon | adenocarcinoma, moderately differentiated | T3N1bM1a | IV A | — | +/− |
| 38 | 36 | F | Ascending colon | adenocarcinoma, moderately differentiated | T3N2bM1b | IV B | — | + |
| 39 | 69 | M | Cecum | adenocarcinoma, moderately differentiated | T2N1bM1a | IV A | — | +++ |

TABLE 2-continued

| No. | Age | Sex | Organ | Diagnosis | pTNM | Stage | Months* | SLC6A6 |
|---|---|---|---|---|---|---|---|---|
| 40 | 50 | M | Transverse | adenocarcinoma, moderately differentiated | T3N2aM1b | IV B | — | +++ |
| 41 | 55 | M | Lung | metastatic carcinoma from #31 | — | — | 45 | +++ |
| 42 | 46 | F | Lymph Node | metastatic carcinoma from #32 | — | — | 0 | +/− |
| 43 | 45 | M | Lung | metastatic carcinoma from #33 | — | — | 17 | + |
| 44 | 47 | F | Ovary | metastatic carcinoma from #34 | — | — | 0 | + |
| 45 | 62 | M | Lung | metastatic carcinoma from #35 | — | — | 36 | + |
| 46 | 53 | M | Liver | metastatic carcinoma from #36 | — | — | 0 | + |
| 47 | 41 | F | Ovary | metastatic carcinoma from #37 | — | — | 17 | + |
| 48 | 35 | F | Uterus | metastatic carcinoma from #38 | — | — | 0 | ++ |
| 49 | 69 | M | Liver | metastatic carcinoma from #39 | — | — | 0 | +++ |
| 50 | 50 | M | Omentum | metastatic carcinoma from #40 | — | — | 0 | +++ |
| 51 | 44 | M | Rectum | normal colon (adjacent to cancer, match of #33) | — | — | . | − |
| 52 | 47 | F | Sigmoid colon | normal colon (adjacent to cancer, match of #34) | — | — | — | − |
| 53 | 54 | M | Sigmoid colon | normal colon (adjacent to cancer, match of #9) | — | — | — | − |
| 54 | 57 | M | Descending colon | normal colon (adjacent to cancer, match of #1) | — | — | — | +/− |
| 55 | 60 | M | Rectum | normal colon (adjacent to cancer, match of 2) | — | — | — | +/− |
| 56 | 59 | M | Sigmoid colon | normal colon (adjacent to cancer, match of #3) | — | — | — | +/− |
| 57 | 58 | F | Rectum | normal colon (adjacent to cancer, match of #4) | — | — | — | +/− |
| 58 | 64 | M | Rectum | normal colon (adjacent to cancer, match of #5) | — | — | — | +/− |
| 59 | 68 | M | Ascending colon | normal colon (adjacent to cancer, match of #24) | — | — | — | +/− |

Example 5

Immunohistological Staining

Figure 6:
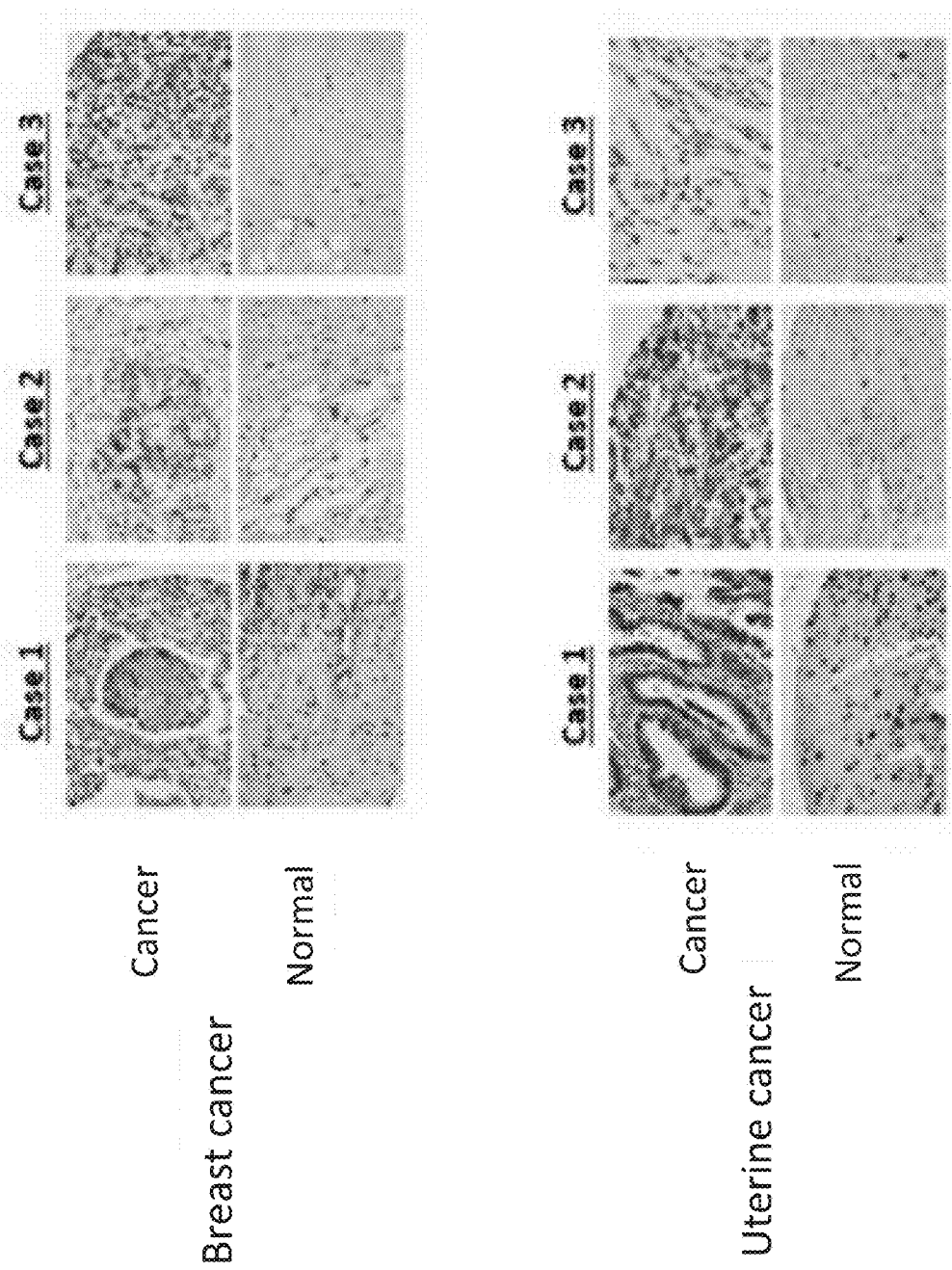
FIG. 6 shows the results of immunohistological staining in tissues of breast and uterine cancers (Cancer) and tissues of their respective normal organs (Normal).

In the same manner as shown in Example 4 above, cancer tissues of breast and uterine cancers (Cancer) and their respective normal tissues (Normal) were immunohistologically stained with the mouse antibody (clone 205). The results obtained are shown in FIG. 6. In both breast cancer and uterine cancer, cancer lesions were also accurately stained with the SLC6A6 antibody of the present invention. All of the 3 cases were found to be positive (100%) in breast cancer, while 2 of the 3 cases were found to be strongly positive (66%) in uterine cancer.

Example 6

Competitive Inhibition Test

Figure 7:
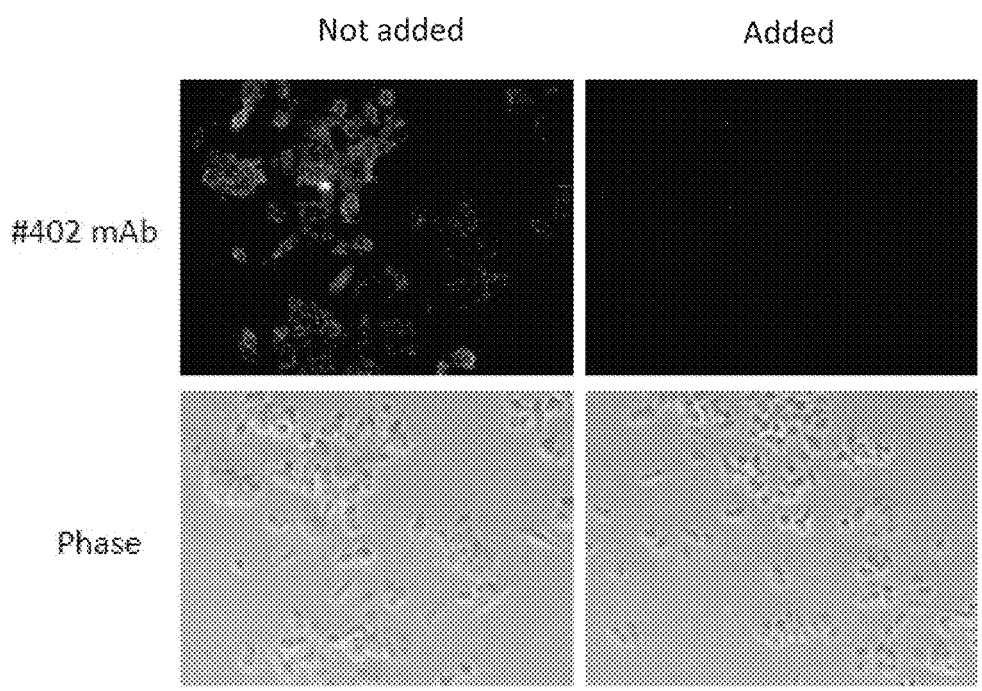
FIG. 7 shows the analysis results indicating that the binding reaction of antibody clone 402 to SLC6A6 on the colorectal cancer cell membrane is competitively inhibited by a partial protein (E. coli recombinant) of the extracellular region of SLC6A6.

Among the monoclonal antibodies obtained above, the antibody clone 402 was analyzed for binding to an extracellular domain of SLC6A6. The antibody clone 402 (10 μg/mL) and the partial protein of the extracellular region of SLC6A6 prepared in Example 1(4) (15 μg/mL) were mixed and reacted at 37° C. for 1 hour. A sample free from the recombinant protein was prepared as a control in the same manner. Each sample was reacted at 4° C. for 1 hour with HCT116 cells cultured on glass, and then reacted with a secondary antibody in the same manner as shown in Example 1(8) for detection. The results obtained are shown in FIG. 7. In FIG. 7, "Phase" represents images observed in visible light under a phase contrast microscope.

FIG. 7 shows that the fluorescence generated upon binding of the antibody clone 402 to HCT116 disappears when the partial protein of the extracellular region of SLC6A6 is added. This indicated that the antibody clone 402 had the ability to react with the extracellular region of SLC6A6. Namely, the antibody clone 402 was demonstrated to specifically react with the extracellular region of SLC6A6.

Example 7

Preparation of Chimeric Antibodies
(1) Cloning of Genes

The hybridoma cells obtained in Example 1 were cultured and their total RNA was extracted with a Qiagen RNeasy Mini kit. From the extracted total RNA (2 μg), cDNA was synthesized by reverse transcription (RT) reaction at 50° C. for 1 hour with SuperScript III reverse transcriptase (Invitrogen), followed by heating at 85° C. for 5 minutes to stop the reaction. The resulting cDNA was used as a template for PCR reaction with the following primers and with KOD PLUS (TOYOBO) to amplify a desired gene.

To amplify an H chain variable region fragment of the antibody, the primers of SEQ ID NO: 7, SEQ ID NO: 8 and SEQ ID NO: 9 were used in PCR reaction (30 cycles of denaturation at 94° C. for 2 minutes, subsequent annealing at 56° C. for 15 seconds and elongation at 68° C. for 45 seconds) to thereby obtain the desired fragment.

Long:
(SEQ ID NO: 7)
5'-CTAATACGACTCACTATAGGGCAAGCAGTGGTATCAACGCAGAGT-3'

Short:
(SEQ ID NO: 8)
5'-CTAATACGACTCACTATAGGGC-3' mIgG2a_CH1_reverse:
(SEQ ID NO: 9)
5'-CCAGGGGCCAGTGGATAGACCGATGGGGCTGTTG-3'

To amplify an L chain leader sequence and an L chain variable region fragment of the antibody, the primers of SEQ ID NO: 7, SEQ ID NO: 8 and SEQ ID NO: 10 were used in PCR reaction (30 cycles of denaturation at 94° C. for 2 minutes, subsequent annealing at 56° C. for 15 seconds and elongation at 68° C. for 45 seconds) to thereby obtain the desired fragment.

mIgkappa_R3:
(SEQ ID NO: 10)
5'-GCACCTCCAGATGTTAACTGCTCACT-3'

The purified PCR amplification fragments were each mixed with 10 mM dNTP Mix (Invitrogen Corporation) and 2× GoTaq Maxter Mix (Promega) and reacted at 70° C. for 15 minutes, followed by ice cooling at 4° C. for 2 minutes to ensure dA addition to the 3'-terminal end. Then, using a pGEM-T-Easy Vector System (Promega), the H chain fragment and the L chain fragment were cloned by the so-called TA cloning method.
(i) Construction of H Chain Expression Vector First, to amplify the H chain constant region of human IgG1, oligo DNA shown in SEQ ID NO: 11 was chemically synthesized, followed by PCR reaction (30 cycles of denaturation at 94° C. for 2 minutes, subsequent annealing at 58° C. for 15 seconds and elongation at 68° C. for 60 seconds) with the primers of SEQ ID NO: 12 and SEQ ID NO: 13 to thereby obtain an H chain constant region fragment of human IgG1.

```
hHchain:
                                              (SEQ ID NO: 11)
5'-GCTAGCACCAAGGGCCCATCGGTCTTCCCCCTGGCACCCTCCTCCA

AGAGCACCTCTGGGGGCACAGCGGCCCTGGGCTGCCTGGTCAAGGACTA

CTTCCCCGAACCGGTGACGGTGTCGTGGAACTCAGGCGCCCTGACCAGC

GGCGTGCACACCTTCCCGGCTGTCCTACAGTCCTCAGGACTCTACTCCC

TCAGCAGCGTGGTGACCGTGCCCTCCAGCAGCTTGGGCACCCAGACCTA

CATCTGCAACGTGAATCACAAGCCCAGCAACACCAAGGTGGACAAGAAA

GTTGAGCCCAAATCTTGTGACAAAACTCACACATGCCCACCGTGCCCAG

CACCTGAACTCCTGGGGGACCGTCAGTCTTCCTCTTCCCCCCAAAACC

CAAGGACACCCTCATGATCTCCCGGACCCCTGAGGTCACATGCGTGGTG

GTGGACGTGAGCCACGAAGACCCTGAGGTCAAGTTCAACTGGTACGTGG

ACGGCGTGGAGGTGCATAATGCCAAGACAAAGCCGCGGGAGGAGCAGTA

CAACAGCACGTACCGTGTGGTCAGCGTCCTCACCGTCCTGCACCAGGAC

TGGCTGAATGGCAAGGAGTACAAGTGCAAGGTCTCCAACAAAGCCCTCC

CAGCCCCCATCGAGAAAACCATCTCCAAAGCCAAAGGGCAGCCCCGAGA

ACCACAGGTGTACACCCTGCCCCCATCCCGGGATGAGCTGACCAAGAAC

CAGGTCAGCCTGACCTGCCTGGTCAAAGGCTTCTATCCCAGCGACATCG

CCGTGGAGTGGGAGAGCAATGGGCAGCCGGAGAACAACTACAAGACCAC

GCCTCCCGTGCTGGACTCCGACGGCTCCTTCTTCCTCTACAGCAAGCTC

ACCGTGGACAAGAGCAGGTGGCAGCAGGGGAACGTCTTCTCATGCTCCG

TGATGCATGAGGCTCTGCACAACCACTACACGCAGAAGAGCCTCTCCCT

GTCTCCGGGTAAATGA-3' hCg1_F(EcoRI-NheI):
                                              (SEQ ID NO: 12)
5'-TTTGAATTCGCTAGCACCAAGGGCCCATC-3' hCgI_R(NotI):
                                              (SEQ ID NO: 13)
5'-TTTGCGGCCGCTCATTTACCCGGAGACAGGGAGAG-3'
```

Secondly, a MluI recognition sequence in pEF6-myc/HisA vector (Invitrogen) was disrupted, and the oligonucleotides of SEQ ID NO: 14 and SEQ ID NO: 15 were annealed and then introduced by using restriction enzymes (KpnI/BamHI) (this vector is designated as pEF6-Leader).

```
Hchain_signal_top(KpnI-BamHI):
                                              (SEQ ID NO: 14)
5'-CATGGGTTGGAGCCTCATCTTGCTCTTCCTTGTCGCTGTTGCTACG

CGTG-3'

Hchain_signal_bottom(KpnI-BamH):
                                              (SEQ ID NO: 15)
5'-GGATCCACGCGTAGCAACAGCGACAAGGAAGAGCAAGATGAGGCTC

CAACCCATGGTAC-3'
```

Then, the amplified human IgG H chain constant region was introduced into pEF6-Leader by using restriction enzymes (EcoRI/NotI) (this vector is designated as pEF6-hHchain-cloning).

Then, to introduce the H chain variable region fragment of the 205 antibody into pEF6-hHchain-cloning, the H chain variable region fragment cloned by the TA cloning method was used as a template for PCR reaction (30 cycles of denaturation at 94° C. for 2 minutes, subsequent annealing at 56° C. for 15 seconds and elongation at 68° C. for 45 seconds) with the primers of SEQ ID NO: 16 and SEQ ID NO: 17 to thereby obtain the H chain variable region fragment.

```
Forward:
                                              (SEQ ID NO: 16)
5'-TTTACGCGTGTCCTGTCCCAGGTCCAGCTGCAGCAGTC-3'

Reverse:
                                              (SEQ ID NO: 17)
5'-TTTGCTAGCTGCAGAGACAGTGACCAGAGTCCCT-3'
```

Subsequently, the amplified H chain variable region fragment was introduced into pEF6-hHchain-cloning by using restriction enzymes (MluI/NheI) (the vector obtained is hereinafter designated as the 205 chimeric H chain expression vector).

(ii) Construction of L Chain Expression Vector

First, to amplify the human kappa chain constant region, oligo DNA shown in SEQ ID NO: 18 was chemically synthesized, followed by PCR reaction (30 cycles of denaturation at 94° C. for 2 minutes, subsequent annealing at 58° C. for 15 seconds and elongation at 68° C. for 30 seconds) with the primers of SEQ ID NO: 19 and SEQ ID NO: 20 to thereby obtain a human kappa chain constant region fragment.

```
hLchain:
                                              (SEQ ID NO: 18)
5'-CACCAAGCTGGAAATCAAACGTACGGTGGCTGCACCATCTGTCTTC

ATCTTCCCGCCATCTGATGAGCAGTTGAAATCTGGAACTGCCTCTGTTG

TGTGCCTGCTGAATAACTTCTATCCCAGAGAGGCCAAAGTACAGTGGAA

GGTGGATAACGCCCTCCAATCGGGTAACTCCCAGGAGAGTGTCACAGAG

CAGGACAGCAAGGACAGCACCTACAGCCTCAGCAGCACCCTGACGCTGA

GCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

TAG-3' hCk_F(EcoRI-BsiWI):
                                              (SEQ ID NO: 19)
5'-TTTGAATTCCGTACGGTGGCTGCACCATC-3' hCk_R(NotI):
                                              (SEQ ID NO: 20)
5'-TTTGCGGCCGCCTAACACTCTCCCCTGTTG-3'
```

Secondly, the amplified human kappa chain constant region was introduced into pEF1-myc/HisA vector (Invitrogen) by using restriction enzymes (EcoRI/NotI) (this vector is designated as pEF1-hLchain-cloning).

Then, to introduce the L chain signal sequence and variable region of the 205 antibody into pEF1-hLchain-cloning, the L chain signal sequence and variable region fragment cloned by the TA cloning method was used as a template for PCR reaction (30 cycles of denaturation at 94°

C. for 2 minutes, subsequent annealing at 58° C. for 15 seconds and elongation at 68° C. for 30 seconds) with the primers of SEQ ID NO: 21 and SEQ ID NO: 22 to thereby obtain the L chain signal sequence and variable region fragment of the 205 antibody.

```
Forward2:
                                      (SEQ ID NO: 21)
5'-TTTGGATCCACCATGAACATGCTCACTCAGC-3'

Reverse2:
                                      (SEQ ID NO: 22)
5'-TTTCGTACGTTTGATTTCCAGCTTGGTG-3'
```

Then, the amplified L chain signal sequence and variable region fragment was introduced into pEF1-hLchain-cloning by using restriction enzymes (BamHI/BsiWI) (this vector is designated as the 205 chimeric L chain expression vector).

The H chain of the thus prepared human-mouse chimeric 205 antibody has the DNA sequence shown in SEQ ID NO: 23 and the amino acid sequence shown in SEQ ID NO: 24. Likewise, the L chain has the DNA sequence shown in SEQ ID NO: 25 and the amino acid sequence shown in SEQ ID NO: 26.

Moreover, human-mouse chimeric antibodies were also prepared for the other antibodies. The H chain of the human-mouse chimeric 402 antibody has the DNA sequence shown in SEQ ID NO: 27 and the amino acid sequence shown in SEQ ID NO: 28. Likewise, the L chain has the DNA sequence shown in SEQ ID NO: 29 and the amino acid sequence shown in SEQ ID NO: 30. Further, the H chain of the human-mouse chimeric 419 antibody has the DNA sequence shown in SEQ ID NO: 31 and the amino acid sequence shown in SEQ ID NO: 32. Likewise, the L chain has the DNA sequence shown in SEQ ID NO: 33 and the amino acid sequence shown in SEQ ID NO: 34. Furthermore, the H chain of the human-mouse chimeric 303 antibody has the DNA sequence shown in SEQ ID NO: 35 and the amino acid sequence shown in SEQ ID NO: 36. Likewise, the L chain has the DNA sequence shown in SEQ ID NO: 37 and the amino acid sequence shown in SEQ ID NO: 38. Furthermore, the H chain of the human-mouse chimeric 422 antibody has the DNA sequence shown in SEQ ID NO: 39 and the amino acid sequence shown in SEQ ID NO: 40. Likewise, the L chain has the DNA sequence shown in SEQ ID NO: 41 and the amino acid sequence shown in SEQ ID NO: 42. Furthermore, the H chain of the human-mouse chimeric 430 antibody has the DNA sequence shown in SEQ ID NO: 43 and the amino acid sequence shown in SEQ ID NO: 44. Likewise, the L chain has the DNA sequence shown in SEQ ID NO: 45 and the amino acid sequence shown in SEQ ID NO: 46.

```
SEQ ID NO: 23:
ATGGGTTGGAGCCTCATCTTGCTCTTCCTTGTCGCTGTTGCTACGCGTGTCCTGTCCCAGGTCAAAC

TGCAGCAGTCTGGACCTGAGCTGGTAAAGCCTGGGGCTTCAGTGAAGATGTCCTGCAAGGCTTCTGG

ATACACATTCACTAGCTATGTTATGCACTGGGTGAAGCAGAAGCCTGGGCAGGGCCTTGAGTGGATT

GGATATATTAATCCTTACAATGATGGTACTAAGTACAATGAGAAGTTCAAAGGCAAGGCCACACTGA

CTTCAGACAAATCCTCCAGCACAGCCTACATGGAGCTCAGCAGCCTGACCTCTGAGGACTCTGCGGT

CTATTACTGTGCAAGGAGGAAGGCCTGGTTTGCTTACTGGGGCCAAGGGACTCTGGTCACTGTCTCT

GCAGCTAGCACCAAGGGCCCATCGGTCTTCCCCCTGGCACCCTCCTCCAAGAGCACCTCTGGGGGCA

CAGCGGCCCTGGGCTGCCTGGTCAAGGACTACTTCCCCGAACCGGTGACGGTGTCGTGGAACTCAGG

CGCCCTGACCAGCGGCGTGCACACCTTCCCGGCTGTCCTACAGTCCTCAGGACTCTACTCCCTCAGC

AGCGTGGTGACCGTGCCCTCCAGCAGCTTGGGCACCCAGACCTACATCTGCAACGTGAATCACAAGC

CCAGCAACACCAAGGTGGACAAGAAAGTTGAGCCCAAATCTTGTGACAAAACTCACACATGCCCACC

GTGCCCAGCACCTGAACTCCTGGGGGGACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCCTGAGG

TCAAGTTCAACTGGTACGTGGACGGCGTGGAGGTGCATAATGCCAAGACAAAGCCGCGGGAGGAGCA

GTACAACAGCACGTACCGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAAACCATCTCCAAAGCCA

AAGGGCAGCCCCGAGAACCACAGGTGTACACCCTGCCCCCATCCCGGGATGAGCTGACCAAGAACCA

GGTCAGCCTGACCTGCCTGGTCAAAGGCTTCTATCCCAGCGACATCGCCGTGGAGTGGGAGAGCAAT

GGGCAGCCGGAGAACAACTACAAGACCACGCCTCCCGTGCTGGACTCCGACGGCTCCTTCTTCCTCT

ACAGCAAGCTCACCGTGGACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGGGTAAATGA

SEQ ID NO: 24:
MGWSLILLFLVAVATRVLSQVKLQQSGPELVKPGASVKMSCKASGYTFTSYVMHWVKQKPGQGLEWI

GYINPYNDGTKYNEKFKGKATLTSDKSSSTAYMELSSLTSEDSAVYYCARRKAWFAYWGQGTLVTVS
```

AASTKGPSVFPLAPSSKSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKSLSLSPGK*

SEQ ID NO: 25:
ATGAACATGCTCACTCAGCTCCTGGGATTACTGCTGCTCTGGTTTGCAGGTGGTAAATGTGACATTC

AGATGACCCAGTCTCCTGCCTCCCAGTCTGCATCTCTGGGAGAAAGTGTCACCATCACATGCCTGGC

AAGTCAGACCATTGGTACATGGTTAGCATGGTATCAGCAGAAACCAGGGAAATCTCCTCAGCTCCTG

ATTTATGCTGCAACCAGCTTGGCAGATGGGGTCCCATCAAGGTTCAGTGGTAGTGGATCTGGCACAA

AATTTTCTTTCAAGATCAGCAGCCTACAGGCTGAAGATTTTGTAAGTTATTACTGTCAACAACTTTA

CAGTACTCCTCTGACGTTCGGTGGAGGCACCAAGCTGGAAATCAAACGTACGGTGGCTGCACCATCT

GTCTTCATCTTCCCGCCATCTGATGAGCAGTTGAAATCTGGAACTGCCTCTGTTGTGTGCCTGCTGA

ATAACTTCTATCCCAGAGAGGCCAAAGTACAGTGGAAGGTGGATAACGCCCTCCAATCGGGTAACTC

CCAGGAGAGTGTCACAGAGCAGGACAGCAAGGACAGCACCTACAGCCTCAGCAGCACCCTGACGCTG

AGCAAAGCAGACTACGAGAAACACAAAGTCTACGCCTGCGAAGTCACCCATCAGGGCCTGAGCTCGC

CCGTCACAAAGAGCTTCAACAGGGGAGAGTGTTAG

SEQ ID NO: 26:
MNMLTQLLGLLLLWFAGGKCDIQMTQSPASQSASLGESVTITCLASQTIGTWLAWYQQKPGKSPQLL

IYAATSLADGVPSRFSGSGSGTKFSFKISSLQAEDFVSYYCQQLYSTPLTFGGGTKLEIKRTVAAPS

VFIFPPSDEQLKSGTASVVCLLNNFYPREAKVQWKVDNALQSGNSQESVTEQDSKDSTYSLSSTLTL

SKADYEKHKVYACEVTHQGLSSPVTKSFNRGEC*

SEQ ID NO: 27:
ATGGGTTGGAGCCTCATCTTGCTCTTCCTTGTCGCTGTTGCTACGCGTGTCCTGTCCCAGGTCAAAC

TGCAGCAGTCTGGACCTGAGCTGGTGAAGCCTGGGGCTTCAGTGAAAGTATCCTGCACGGCTTCTGG

TTATGCATTCACTCAATACAACTTGTACTGGGTGAAGCTCAGACATGGAAAGTGCCCTAAATGGATC

GGATCTATTGATCCTTACATTGGTGGTACCACCTACAACCAGCAATTCAAGGACAAGGTCACATTGA

CTGTTGACAAGTCTTCCAGCACGGCCTACTTGCATCTCAACAGCCTGACATCTGAAGACTCTGCAAT

CTATTACTGTGCAAGATGGGGACGGATATTTCGATGTCTGGGGCGCAGGGACCACGGTCACCGTC

TCCTCAGCTAGCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGGAACTC

AGGCGCCCTGACCAGCGGCGTGCACACCTTCCCGGCTGTCCTACAGTCCTCAGGACTCTACTCCCTC

AGCAGCGTGGTGACCGTGCCCTCCAGCAGCTTGGGCACCCAGACCTACATCTGCAACGTGAATCACA

AGCCCAGCAACACCAAGGTGGACAAGAAAGTTGAGCCCAAATCTTGTGACAAAACTCACACATGCCC

ACCGTGCCCAGCACCTGAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTG

AGGTCAAGTTCAACTGGTACGTGGACGGCGTGGAGGTGCATAATGCCAAGACAAAGCCGCGGGAGGA

GCAGTACAACAGCACGTACCGTGTGGTCAGCGTCCTCACCGTCCTGCACCAGGACTGGCTGAATGGC

AAGGAGTACAAGTGCAAGGTCTCCAACAAAGCCCTCCCAGCCCCATCGAGAAAACCATCTCCAAAG

CCAAAGGGCAGCCCCGAGAACCACAGGTGTACACCCTGCCCCCATCCCGGGATGAGCTGACCAAGAA

CCAGGTCAGCCTGACCTGCCTGGTCAAAGGCTTCTATCCCAGCGACATCGCCGTGGAGTGGGAGAGC

AATGGGCAGCCGGAGAACAACTACAAGACCACGCCTCCCGTGCTGGACTCCGACGGCTCCTTCTTCC

-continued

TCTACAGCAAGCTCACCGTGGACAAGAGCAGGTGGCAGCAGGGGAACGTCTTCTCATGCTCCGTGAT

GCATGAGGCTCTGCACAACCACTACACGCAGAAGAGCCTCTCCCTGTCTCCGGGTAAATGA

SEQ ID NO: 28:
MGWSLILLFLVAVATRVLSQVKLQQSGPELVKPGASVKVSCTASGYAFTQYNLYWVKLRHGKCPKWI

GSIDPYIGGTTYNQQFKDKVTLTVDKSSSTAYLHLNSLTSEDSAIYYCARWWDGYFDVWGAGTTVTV

SSASTKGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK*

SEQ ID NO: 29:
ATGGATTTTCAGGTGCAGATTTTCAGCTTCCTGCTAATCAGTGCCTCAGTCATTTTGTCCAGAGGAC

AGATTGTTCTCACCCAGTCTCCAGCAATCATGTCTGCTTCTCTAGGGGAACGGGTCACCTTGACCTG

CACTGCCAGCTCAAGTGTAATTTCCAGATACTTGCACTGGTACCAGGTGAAGCCAGGATCCTCCCCC

AAACTCTGGATTTATAGCACATCCAACCTGGCTTCTGGAGTCCCAACTCGCTTCAGTGGCAGTGGGT

CTGGGACCTCTTACTCTCTCACAATCAGTAACATGGAGGCTGAAGATGCTGCCACTTATTACTGCCA

CCAGTATCATCGTTCCCCGCTCACGTTCGGTGCTGGGACCAAGCTGGAGCTGACACGTACGGTGGCT

GCACCATCTGTCTTCATCTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTGGATAACGCCCTCCAATC

GGGTAACTCCCAGGAGAGTGTCACAGAGCAGGACAGCAAGGACAGCACCTACAGCCTCAGCAGCACC

CTGACGCTGAGCAAAGCAGACTACGAGAAACACAAAGTCTACGCCTGCGAAGTCACCCATCAGGGCC

TGAGCTCGCCCGTCACAAAGAGCTTCAACAGGGGAGAGTGTTAG

SEQ ID NO: 30:
MDFQVQIFSFLLISASVILSRGQIVLTQSPAIMSASLGERVTLTCTASSSVISRYLHWYQVKPGSSP

KLWIYSTSNLASGVPTRFSGSGSGTSYSLTISNMEAEDAATYYCHQYHRSPLTFGAGTKLELTRTVA

APSVFIFPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC*

SEQ ID NO: 31:
ATGGGTTGGAGCCTCATCTTGCTCTTCCTTGTCGCTGTTGCTACGCGTGTCCTGTCCCAGATCCAGC

TGCAGCAGTCTGGACCTGAGCTGGTGAAGCCTGGGGCTTCAGTGAAAGTCTCCTGCAAGGCTTTTGG

TTATGCATTCACTAGACACAATATGTACTGGGTGAAGCAGAGGCATGGAAAGTGCCTTGAGTGGATT

GGATATATTGATCCTTTCAATGGTGGTACTAGCTACAACCAGAAGTTCAAGGGCAAGGCCACATTGA

CTGTTGACAAGTCCTCCAGCACAGCCTACATGCATCTCAACAGCCTGACATCTGAGGACTCTGCAGT

CTATTACTGTGCAAGAGTTTATGGTAACTACGCCTGGTTTGCTTACTGGGGCCAAGGGACTCTGGTC

ACTGTCTCTGCAGCTAGCACCAAGGGCCCATCGGTCTTCCCCCTGGCACCCTCCTCCAAGAGCACCT

CTGGGGGCACAGCGGCCCTGGGCTGCCTGGTCAAGGACTACTTCCCCGAACCGGTGACGGTGTCGTG

GAACTCAGGCGCCCTGACCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAAAGTTGAGCCCAAATCTTGTGACAAAACTCACAC

ATGCCCACCGTGCCCAGCACCTGAACTCCTGGGGGGACCGTCAGTCTTCCTCTTCCCCCCAAAACCC

AAGGACACCCTCATGATCTCCCGGACCCCTGAGGTCACATGCGTGGTGGTGGACGTGAGCCACGAAG

ACCCTGAGGTCAAGTTCAACTGGTACGTGGACGGCGTGGAGGTGCATAATGCCAAGACAAAGCCGCG

GGAGGAGCAGTACAACAGCACGTACCGTGTGGTCAGCGTCCTCACCGTCCTGCACCAGGACTGGCTG

```
AATGGCAAGGAGTACAAGTGCAAGGTCTCCAACAAAGCCCTCCCAGCCCCCATCGAGAAAACCATCT

CCAAAGCCAAAGGGCAGCCCCGAGAACCACAGGTGTACACCCTGCCCCCATCCCGGGATGAGCTGAC

CAAGAACCAGGTCAGCCTGACCTGCCTGGTCAAAGGCTTCTATCCCAGCGACATCGCCGTGGAGTGG

GAGAGCAATGGGCAGCCGGAGAACAACTACAAGACCACGCCTCCCGTGCTGGACTCCGACGGCTCCT

TCTTCCTCTACAGCAAGCTCACCGTGGACAAGAGCAGGTGGCAGCAGGGGAACGTCTTCTCATGCTC

CGTGATGCATGAGGCTCTGCACAACCACTACACGCAGAAGAGCCTCTCCCTGTCTCCGGGTAAATGA

SEQ ID NO: 32:
MGWSLILLFLVAVATRVLSQIQLQQSGPELVKPGASVKVSCKAFGYAFTRHNMYWVKQRHGKCLEWI

GYIDPFNGGTSYNQKFKGKATLTVDKSSSTAYMHLNSLTSEDSAVYYCARVYGNYAWFAYWGQGTLV

TVSAASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYNSTYRVVSVLTVLHQDWL

NGKEYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSPGK*

SEQ ID NO: 33:
ATGGGCATCAAAATGGAGTCACAGATTCAGGTCTTTGTATTCGTGTTTCTCTGGTTGTCTGGTGTTG

ACGGAGACATTGTGATGACCCAGTCTCACAAATTCATGTCCACATCAGTAGGAGACAGGGTCAGCAT

CACCTGCAAGGCCAGTCAGGATGTGAGTACTGCTGTAGCCTGGTATCAACAGATACCAGGACAATCT

CCTAAACTACTGATTTACTCGTCATCCTACCGGTACACTGGAGTCCCTGATCGCTTCACTGGCAGTG

GATCTGGGACGGATTTCACTTTCACCATCAGCAGTGTGCAGGCTGAAGACCTGGCAGTTTATTACTG

TCAGCAACATTATAATACTCCGTGGACGTTCGGTGGAGGCACCAAGCTGGAAATCAAACGTACGGTG

GCTGCACCATCTGTCTTCATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAGGTGGATAACGCCCTCCA

ATCGGGTAACTCCCAGGAGAGTGTCACAGAGCAGGACAGCAAGGACAGCACCTACAGCCTCAGCAGC

ACCCTGACGCTGAGCAAAGCAGACTACGAGAAACACAAAGTCTACGCCTGCGAAGTCACCCATCAGG

GCCTGAGCTCGCCCGTCACAAAGAGCTTCAACAGGGGAGAGTGTTAG

SEQ ID NO: 34:
MGIKMESQIQVFVFVFLWLSGVDGDIVMTQSHKFMSTSVGDRVSITCKASQDVSTAVAWYQQIPGQS

PKLLIYSSSYRYTGVPDRFTGSGSGTDFTFTISSVQAEDLAVYYCQQHYNTPWTFGGGTKLEIKRTV

AAPSVFIFPPSDEQLKSGTASVVCLLNNFYPREAKVQWKVDNALQSGNSQESVTEQDSKDSTYSLSS

TLTLSKADYEKHKVYACEVTHQGLSSPVTKSFNRGEC*

SEQ ID NO: 35:
ATGGGTTGGAGCCTCATCTTGCTCTTCCTTGTCGCTGTTGCTACGCGTGTCCTGTCCCAGGTCCAAC

TGCAGCAGCCTGGGGCTGAGTTTGTGAAGCCTGGGACTTCAGTGAAGCTGTCCTGCAAGGCTTCTGG

CTACAACTTCACCAGGTACTGGATAAACTGGGTGAAGCTGAGGCCTGGACAAGGCCTTGAGTGGATT

GGAAATATTTATCCTGCTACTAATGGTATTAACTACAATGAGAAGTTCAAGAGCAAGGCCACACTGA

CTGTGGACACATTCTCCAGCACAGCCTACATGCAACTCAGCAGTCTGGCATCTGAGGACTCTGGTCT

CTATTACTGTGCAAGATGTAAAACGATGTTGTCACGATGTGCCTGGTTTCCTTACTGGGGCCAAGGG

ACTCTGGTCACTGTCTCCGCAGCTAGCACCAAGGGCCCATCGGTCTTCCCCCTGGCACCCTCCTCCA

AGAGCACCTCTGGGGGCACAGCGGCCCTGGGCTGCCTGGTCAAGGACTACTTCCCCGAACCGGTGAC

GGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCT

GCAACGTGAATCACAAGCCCAGCAACACCAAGGTGGACAAGAAAGTTGAGCCCAAATCTTGTGACAA
```

-continued

```
AACTCACACATGCCCACCGTGCCCAGCACCTGAACTCCTGGGGGGACCGTCAGTCTTCCTCTTCCCC

CCAAAACCCAAGGACACCCTCATGATCTCCCGGACCCCTGAGGTCACATGCGTGGTGGTGGACGTGA

GCCACGAAGACCCTGAGGTCAAGTTCAACTGGTACGTGGACGGCGTGGAGGTGCATAATGCCAAGAC

AAAGCCGCGGGAGGAGCAGTACAACAGCACGTACCGTGTGGTCAGCGTCCTCACCGTCCTGCACCAG

GACTGGCTGAATGGCAAGGAGTACAAGTGCAAGGTCTCCAACAAAGCCCTCCCAGCCCCCATCGAGA

AAACCATCTCCAAAGCCAAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCTATCCCAGCGACATCGCC

GTGGAGTGGGAGAGCAATGGGCAGCCGGAGAACAACTACAAGACCACGCCTCCCGTGCTGGACTCCG

ACGGCTCCTTCTTCCTCTACAGCAAGCTCACCGTGGACAAGAGCAGGTGGCAGCAGGGGAACGTCTT

CTCATGCTCCGTGATGCATGAGGCTCTGCACAACCACTACACGCAGAAGAGCCTCTCCCTGTCTCCG

GGTAAATGA

SEQ ID NO: 36:
MGWSLILLFLVAVATRVLSQVQLQQPGAEFVKPGTSVKLSCKASGYNFTRYWINWVKLRPGQGLEWI

GNIYPATNGINYNEKFKSKATLTVDTFSSTAYMQLSSLASEDSGLYYCARCKTMLSRCAWFPYWGQG

TLVTVSAASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVMHEALHNHYTQKSLSLSP

GK*

SEQ ID NO: 37:
ATGATGTCCTCTGCTCAGTTCCTTGGTCTCCTGTTGCTCTGTTTTCAAGGTTCCAGATGTGATATCC

AAATGACTCAGACTACATCCTCCCTGTCTGCCTCTCTGGGAGACAGAGTCACCATCAATTGCAGGGC

AAGTCAGGACATTAGTAATTATTTAAACTGGTATCAGCAGAAACCAGATGGAACTGTTAAACTCCTG

ATCTACGACACATCAAGATTACACTCAAGAGTCCCATCAAGGTTCAGTGGCAGTGGGTCTGGAACAG

ATTATTCTCTCACCATTAGCAACCTGGAGCAAGAAGATATTGCCACTTACTTTTGCCAACAGGGTAA

TATGCTTCCGTGGACGTTCGGTGGAGGCACCAAGCTGGAAATCAAACGTACGGTGGCTGCACCATCT

GTCTTCATCTTCCCGCCATCTGATGAGCAGTTGAAATCTGGAACTGCCTCTGTTGTGTGCCTGCTGA

ATAACTTCTATCCCAGAGAGGCCAAAGTACAGTGGAAGGTGGATAACGCCCTCCAATCGGGTAACTC

CCAGGAGAGTGTCACAGAGCAGGACAGCAAGGACAGCACCTACAGCCTCAGCAGCACCCTGACGCTG

AGCAAAGCAGACTACGAGAAACACAAAGTCTACGCCTGCGAAGTCACCCATCAGGGCCTGAGCTCGC

CCGTCACAAAGAGCTTCAACAGGGGAGAGTGTTAG

SEQ ID NO: 38:
MMSSAQFLGLLLLCFQGSRCDIQMTQTTSSLSASLGDRVTINCRASQDISNYLNWYQQKPDGTVKLL

IYDTSRLHSRVPSRFSGSGSGTDYSLTISNLEQEDIATYFCQQGNMLPWTFGGGTKLEIKRTVAAPS

VFIFPPSDEQLKSGTASVVCLLNNFYPREAKVQWKVDNALQSGNSQESVTEQDSKDSTYSLSSTLTL

SKADYEKHKVYACEVTHQGLSSPVTKSFNRGEC*

SEQ ID NO: 39:
ATGGGTTGGAGCCTCATCTTGCTCTTCCTTGTCGCTGTTGCTACGCGTGTCCTGTCCGAGGTCCAGC

TGCAACAGTCTGGACCTGAGGTGGTGAAGCCTGGACCTTCACTGAGGATGTCCTGCAAGGCCTCTGG

TTACTTTTTCACTGGCAATTCTATGAATTGGGTGAAGAAGACCCATGGACGGAGCCTTGAGTGGATT

GGACTTATTGATCTTTCCAATGGTGAAACTCGCTTCAATCAGAAGTTCAAGGGCAAGGCCACTTTAA

CTGTGGACAAGTCATCCGGCACAGCCTACATGGAACTCCTCAATCTGACATCTGAGGACTCTGCAGT
```

-continued

```
CTATTACTGTGCAAGCAGGTCTGCCATGATTATGCCCTGTTTTTCTCATTGGGGCCAGGGGACTCTG

GTCACTGTCTCTGCAGCTAGCACCAAGGGCCCATCGGTCTTCCCCCTGGCACCCTCCTCCAAGAGCA

CCTCTGGGGGCACAGCGGCCCTGGGCTGCCTGGTCAAGGACTACTTCCCCGAACCGGTGACGGTGTC

GTGGAACTCAGGCGCCCTGACCAGCGGCGTGCACACCTTCCCGGCTGTCCTACAGTCCTCAGGACTC

TACTCCCTCAGCAGCGTGGTGACCGTGCCCTCCAGCAGCTTGGGCACCCAGACCTACATCTGCAACG

TGAATCACAAGCCCAGCAACACCAAGGTGGACAAGAAAGTTGAGCCCAAATCTTGTGACAAAACTCA

CACATGCCCACCGTGCCCAGCACCTGAACTCCTGGGGGGACCGTCAGTCTTCCTCTTCCCCCCAAAA

CCCAAGGACACCCTCATGATCTCCCGGACCCCTGAGGTCACATGCGTGGTGGTGGACGTGAGCCACG

AAGACCCTGAGGTCAAGTTCAACTGGTACGTGGACGGCGTGGAGGTGCATAATGCCAAGACAAAGCC

GCGGGAGGAGCAGTACAACAGCACGTACCGTGTGGTCAGCGTCCTCACCGTCCTGCACCAGGACTGG

CTGAATGGCAAGGAGTACAAGTGCAAGGTCTCCAACAAAGCCCTCCCAGCCCCCATCGAGAAAACCA

TCTCCAAAGCCAAAGGGCAGCCCCGAGAACCACAGGTGTACACCCTGCCCCCATCCCGGGATGAGCT

GACCAAGAACCAGGTCAGCCTGACCTGCCTGGTCAAAGGCTTCTATCCCAGCGACATCGCCGTGGAG

TGGGAGAGCAATGGGCAGCCGGAGAACAACTACAAGACCACGCCTCCCGTGCTGGACTCCGACGGCT

CCTTCTTCCTCTACAGCAAGCTCACCGTGGACAAGAGCAGGTGGCAGCAGGGGAACGTCTTCTCATG

CTCCGTGATGCATGAGGCTCTGCACAACCACTACACGCAGAAGAGCCTCTCCCTGTCTCCGGGTAAA

TGA

SEQ ID NO: 40:
MGWSLILLFLVAVATRVLSEVQLQQSGPEVVKPGPSLRMSCKASGYFFTGNSMNWVKKTHGRSLEWI

GLIDLSNGETRFNQKFKGKATLTVDKSSGTAYMELLNLTSEDSAVYYCASRSAMIMPCFSHWGQGTL

VTVSAASTKGPSVFPLAPSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHEALHNHYTQKSLSLSPGK*

SEQ ID NO: 41:
ATGGAGACACATTCTCAGGTCTTTGTATACATGTTGCTGTGGTTGTCTGGTATTGAAGGAGACATTG

TGATGACCCAGTCTCACAACTTCATGTCCACATCAATTGGAGACAGGGTCAACATCACCTGCAAGGC

CAGTCAGGATGTGGCTACTGCTGTTGCCTGGTTTCAACAGAAACCAGGTCAATCTCCTAAACTCCTA

ATTTACTGGACGTCCACCCGGCACACTGGAGTCCCTGATCGCTTCACAGGCAGTGGATATGGGACAG

ATTTCACTCTCACCATTAGCCATGTGCAGTCTGAAGACTTGGCCGATTATTTCTGTCAACAATATGA

CACCTATCCGTACACGTTCGGAGGGGGGACCAAGTTGGAGATAAAACGTACGGTGGCTGCACCATCT

GTCTTCATCTTCCCGCCATCTGATGAGCAGTTGAAATCTGGAACTGCCTCTGTTGTGTGCCTGCTGA

ATAACTTCTATCCCAGAGAGGCCAAAGTACAGTGGAAGGTGGATAACGCCCTCCAATCGGGTAACTC

CCAGGAGAGTGTCACAGAGCAGGACAGCAAGGACAGCACCTACAGCCTCAGCAGCACCCTGACGCTG

AGCAAAGCAGACTACGAGAAACACAAAGTCTACGCCTGCGAAGTCACCCATCAGGGCCTGAGCTCGC

CCGTCACAAAGAGCTTCAACAGGGGAGAGTGTTAG

SEQ ID NO: 42:
METHSQVFVYMLLWLSGIEGDIVMTQSHNFMSTSIGDRVNITCKASQDVATAVAWFQQKPGQSPKLL

IYWTSTRHTGVPDRFTGSGYGTDFTLTISHVQSEDLADYFCQQYDTYPYTFGGGTKLEIKRTVAAPS

VFIFPPSDEQLKSGTASVVCLLNNFYPREAKVQWKVDNALQSGNSQESVTEQDSKDSTYSLSSTLTL

SKADYEKHKVYACEVTHQGLSSPVTKSFNRGEC*
```

SEQ ID NO: 43:
ATGGGTTGGAGCCTCATCTTGCTCTTCCTTGTCGCTGTTGCTACGCGTGTCCTGTCCGAGATCCAAC

TGCAGCAGTCTGGACCTGAGGTGGTGAAGCCTGGGACTTCAGTGAGAGTATCCTGCACGGCTTCTGG

TTATGCATTCACTCAGTACAACTTGTACTGGGTGAAACTCAGACATGGAAAGTGCCCTAAATGGATC

GGATCTATTGATCCTTACATTGGTGGTGCCAACTACAATCAGCAATTCAAGGACAAGGTCACATTGA

CTGTTGACAAGTCTTCCAGCACGGCCTACTTACATCTCAACAGCCTGACATCTGAAGACTCTGCAAT

CTATTACTGTGCAAGATGGTGGGACGGATATTTCGATGTCTGGGGCGCAGGGACCACGGTCACCGTC

TCCTCAGCTAGCACCAAGGGCCCATCGGTCTTCCCCCTGGCACCCTCCTCCAAGAGCACCTCTGGGG

GCACAGCGGCCCTGGGCTGCCTGGTCAAGGACTACTTCCCCGAACCGGTGACGGTGTCGTGGAACTC

AGGCGCCCTGACCAGCGGCGTGCACACCTTCCCGGCTGTCCTACAGTCCTCAGGACTCTACTCCCTC

AGCAGCGTGGTGACCGTGCCCTCCAGCAGCTTGGGCACCCAGACCTACATCTGCAACGTGAATCACA

AGCCCAGCAACACCAAGGTGGACAAGAAAGTTGAGCCCAAATCTTGTGACAAAACTCACACATGCCC

ACCGTGCCCAGCACCTGAACTCCTGGGGGGACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTG

AGGTCAAGTTCAACTGGTACGTGGACGGCGTGGAGGTGCATAATGCCAAGACAAAGCCGCGGGAGGA

GCAGTACAACAGCACGTACCGTGTGGTCAGCGTCCTCACCGTCCTGCACCAGGACTGGCTGAATGGC

AAGGAGTACAAGTGCAAGGTCTCCAACAAAGCCCTCCCAGCCCCCATCGAGAAAACCATCTCCAAAG

CCAAAGGGCAGCCCCGAGAACCACAGGTGTACACCCTGCCCCCATCCCGGGATGAGCTGACCAAGAA

CCAGGTCAGCCTGACCTGCCTGGTCAAAGGCTTCTATCCCAGCGACATCGCCGTGGAGTGGGAGAGC

AATGGGCAGCCGGAGAACAACTACAAGACCACGCCTCCCGTGCTGGACTCCGACGGCTCCTTCTTCC

TCTACAGCAAGCTCACCGTGGACAAGAGCAGGTGGCAGCAGGGGAACGTCTTCTCATGCTCCGTGAT

GCATGAGGCTCTGCACAACCACTACACGCAGAAGAGCCTCTCCCTGTCTCCGGGTAAATGA

SEQ ID NO: 44:
MGWSLILLFLVAVATRVLSEIQLQQSGPEVVKPGTSVRVSCTASGYAFTQYNLYWVKLRHGKCPKWI

GSIDPYIGGANYNQQFKDKVTLTVDKSSSTAYLHLNSLTSEDSAIYYCARWWDGYFDVWGAGTTVTV

SSASTKGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLTCLVKGFYPSDIAVEWES

NGQPENNYKTTPPVLDSDGSFFLYSKLTVDKSRWQQGNVFSCSVMHEALHNHYTQKSLSLSPGK*

SEQ ID NO: 45:
ATGGATTTTCAGGTGCAGATTTTCAGCTTCCTGCTAATCAGTGCCTCAGTCATTTTGTCCAGAGGAC

AAATTGTTCTCACCCAGTCTCCAGCAATCATGTCTGCTTCTCTAGGGGAACGGGTCACCATGACCTG

CACTGCCAGTTCAAGTGTAAGTTTCAGATACTTGCACTGGTACCAGGTGAAGCCAGGATCCTCCCCC

AAACTCTGGATTTATAGCACATCCAACCTGGCTTCTGGAGTCCCAAGTCGCATCAGTGGCAGTGGGT

CTGGGACCTCTTACTTTCTCACAATCAGTAACATGGAGGCTGAAGATGCTGCCACTTATTACTGCCA

CCAGTATCATCGCTCCCCGCTCACGTTCGGTGCTGGGACCAAGCTGGAGCTGACACGTACGGTGGCT

GCACCATCTGTCTTCATCTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTGGATAACGCCCTCCAATC

GGGTAACTCCCAGGAGAGTGTCACAGAGCAGGACAGCAAGGACAGCACCTACAGCCTCAGCAGCACC

CTGACGCTGAGCAAAGCAGACTACGAGAAACACAAAGTCTACGCCTGCGAAGTCACCCATCAGGGCC

TGAGCTCGCCCGTCACAAAGAGCTTCAACAGGGGAGAGTGTTAG

-continued

SEQ ID NO: 46:
MDFQVQIFSFLLISASVILSRGQIVLTQSPAIMSASLGERVTMTCTASSSVSFRYLHWYQVKPGSSP

KLWIYSTSNLASGVPSRISGSGSGTSYFLTISNMEAEDAATYYCHQYHRSPLTFGAGTKLELTRTVA

APSVFIFPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC*

Tables 3 and 4 below show information about the amino acid sequences of the variable region and CDR1 to CDR3 of the respective human-mouse chimeric antibodies obtained above. Numerals given to the variable region and CDR1 to CDR3 represent corresponding amino acid numbers in the amino acid sequence shown in each SEQ ID NO.

TABLE 3

Analysis of H chain variable region

| Clone | SEQ ID NO | Variable region | CDR1 | CDR2 | CDR3 |
|---|---|---|---|---|---|
| 205 | 24 | 21-135 | 50-54 | 69-86 | 118-125 |
| 402 | 28 | 21-136 | 50-54 | 69-86 | 118-126 |
| 419 | 32 | 21-138 | 50-54 | 69-86 | 118-128 |
| 303 | 36 | 21-141 | 50-54 | 69-86 | 118-131 |
| 422 | 40 | 21-139 | 50-54 | 69-86 | 118-129 |
| 430 | 44 | 21-136 | 50-54 | 69-86 | 118-126 |

TABLE 4

Analysis of L chain variable region

| Clone | SEQ ID NO | Variable region | CDR1 | CDR2 | CDR3 |
|---|---|---|---|---|---|
| 205 | 26 | 21-127 | 44-54 | 70-76 | 109-116 |
| 402 | 30 | 23-130 | 46-57 | 73-79 | 112-119 |
| 419 | 34 | 25-131 | 48-58 | 74-80 | 113-120 |
| 303 | 38 | 21-127 | 44-54 | 70-76 | 109-116 |
| 422 | 42 | 21-127 | 44-54 | 70-76 | 109-116 |
| 430 | 46 | 23-130 | 46-57 | 73-79 | 112-119 |

Furthermore, a human-mouse chimeric antibody whose H chain and L chain constant regions were humanized was also prepared for the antibody clone 4B9b disclosed in PCT/JP2011/070418.

(2) Expression of Human IgG-Converted Antibodies

In 6-well plates, CHO cells were cultured to reach 90% confluency, and the H chain and L chain expression vectors prepared in (1) were transformed into the CHO cells using Fugene6 (Roche) to cause transient protein expression. Transformation conditions were set in accordance with the manufacturer's recommended protocols. After 24 hours, the medium was replaced with F12 medium (GIBCO) and culture was continued for 4 days. The culture supernatants were collected and centrifuged to remove the cells, followed by collecting the supernatant. Antibody purification was conducted in the same manner as shown in Example 1(7).

Alternatively, the humanized IgG antibodies were expressed in the following manner. For antibody protein expression, an Expii293F Expression system (Life technologies) was used. Using a 125 mL Erlenmeyer flask equipped with a vent cap (Corning), 30 mL of a cell suspension prepared at a density of $2 \times 10^6$ cells/mL was cultured by gyratory culture (125 rpm) at 37° C. under 8% $CO_2$ for 24 hours.

Then, 81 µL of ExpiFectamine 293 reagent was mixed with 1.419 mL of Optimem (GIBCO) and allowed to stand for 5 minutes. To this mixture, plasmids into which genes encoding antibody H and L chains, respectively, had been cloned were each added in an amount of 15 µg and allowed to stand at room temperature for 20 minutes.

The 293F cells prepared above were suspended again at a density of $2.9 \times 10^6$ cells/ml in 25.5 mL of the medium and the plasmid solution (3 mL) was added thereto to initiate culture. At 20 hours after the initiation of culture, ExpiFectaine 293 transfection enhancer 1 (150 µL) and enhancer 2 (1.5 mL) were added. The cells were cultured for 3 days to collect the culture supernatant.

(3) Purification of Human IgG-Converted Antibodies

For antibody purification, a Protein G sepharose carrier was used in the same manner as shown in Example 1(7), or alternatively, a hydroxyapatite carrier was used for purification.

When using hydroxyapatite for purification, 250 mg of cheramic hydroxyapatite Type II, 20 µm (Bio-Rad) was used relative to 12 ml of the culture supernatant cultured in the same manner as shown in Example 7(2). The hydroxyapatite carrier was equilibrated with 10 mM phosphate buffer (10 mM $Na_2HPO_4$, 10 mM $NaH_2PO_4$ (pH 6.7)), while 36 mL of 10 mM phosphate buffer was added to 12 mL of the culture supernatant containing antibody proteins. To this diluted culture supernatant, the equilibrated hydroxyapatite carrier was added and stirred for 18 hours at 4° C. The carrier was filled into an Econo-Pac column (Bio-Rad) and washed with 10 volumes of 10 mM phosphate buffer, followed by separation with solutions containing sodium chloride at concentrations of 50, 300, 500, 700, 800, 1000 and 1300 mM, respectively, in 10 mM phosphate buffer. 95% or more of the proteins eluted between 500 mM and 700 mM sodium chloride were found to be antibody proteins.

It should be noted that the 205 antibody was taken as an example and its human-mouse chimeric antibody purified as above was measured for binding activity in the same manner as shown in Example 1(7). In this case, the antibody concentration was set to 10 µg/mL. As a secondary antibody, anti-mouse IgG polyclonal antibody-HRP label was used for the 205 antibody and anti-human IgG polyclonal antibody-HRP label was used for its chimeric antibody. As a result, even when the 205 antibody was converted into a human-mouse chimeric antibody, its binding ability to SLC6A6 in HCT15 and HT-29 cells (which are human colorectal cancer cells) was confirmed to be maintained.

Example 8

(1) Transient Expression of SLC6A6 Gene

The expression vector shown in Example 1(2) prepared by integrating the SLC6A6 gene into pEF6 vector was transformed into HCT15, HT-29 and SW480 using FUGENE6 (Roche). Operations were conducted as described in the manufacturer's instructions attached to this kit.

(2) SLC6A6 Overexpression-Induced Changes in Side Population Cells

Stem cells have been isolated using various surface markers, but they have different surface markers depending on their source tissue and are present at low proportion. For these reasons, analysis of stem cells is very difficult. As techniques for their separation and identification, side population (SP) cells have now received attention. Stem cells are high in drug efflux ability and have the property of releasing various substances into the extracellular environment. A technique based on this property of stem cells has been widely used where Hoechst 33342 efflux is used as an indicator for analysis. In this technique, a cell fraction showing weak color development in the staining pattern of Hoechst 33342 is referred to as SP cells. The presence of such SP cells has also been shown for cancer cells, and SP cells have been reported to have significantly higher tumorigenicity than non-SP cells and have now been known as a fraction enriched with cancer stem cells (Cancer Research 2005, 65, p. 6207-6219).

After being transformed in the same manner as shown in Example 8(1) above, the cells were detached on the second day with DISSOCIATION BUFFER (Invitrogen). The cells were stained at 37° C. for 1 hour with a solution prepared to contain 10 µg/mL Hoechst 33342 in PBS(−), followed by analysis using FACS Canto II and a Violet laser (excitation wavelength: 407 nm). Moreover, to identify an SP fraction, an additional experiment was conducted in which verapamil serving an inhibitor of drug efflux transporters was added at a concentration of 30 µg/mL. The results obtained are shown in FIG. 8.

Figure 8:
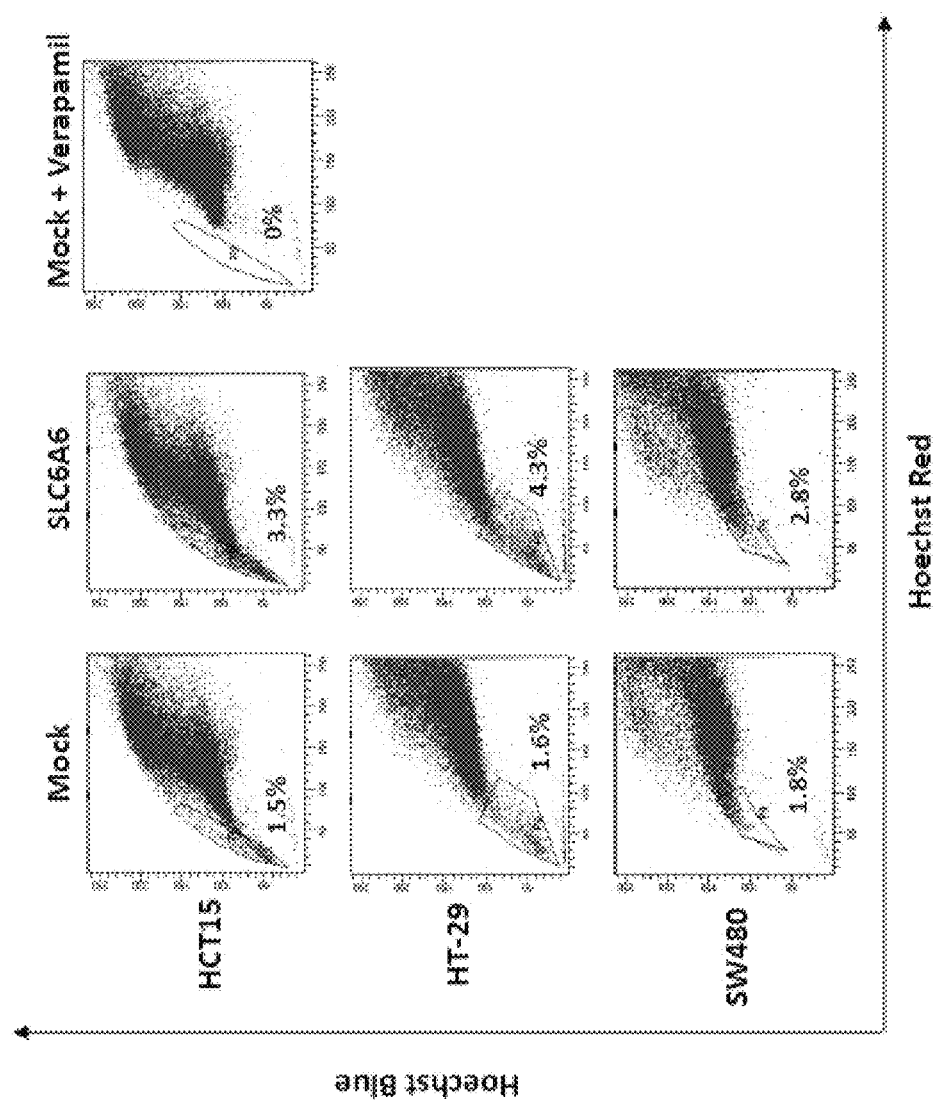
FIG. 8 shows the results analyzed for the number of side population cells upon transient expression of SLC6A6 in human colorectal cancer cells. Fractions within lines each represent SP cells, and the numeral in each panel represents the ratio (%) of SP cells contained. This figure shows that the number of SP cells is increased upon overexpression of the SLC6A6 gene.

FIG. 8 shows the results indicating that the ratio of SP cells is increased upon transient expression of SLC6A6 ("SLC6A6") when compared to the control vector ("Mock"). Namely, it was indicated that SLC6A6 was directly involved in the increase of the SP fraction enriched with a population of stem cells.

Example 9

(1) SLC6A6 Expression in SP Fraction

SLC6A6 expression was analyzed for the SP fraction and non-SP fraction (i.e., major population (MP) fraction) of SW480 cells, which are human colorectal cancer cells. In the same manner as shown in Example 8(2), the cells were stained with Hoechst 33342 and then stained at 4° C. for 1 hour with 1 µg/mL of the 430 antibody purified with Protein G and eluted with an eluent of pH 3.0, and further stained with anti-mouse IgG polyclonal antibody-Alexa Fluor 488 label as a secondary antibody, followed by analysis using FACS Canto II. The results obtained are shown in FIG. 9.

Figure 9:
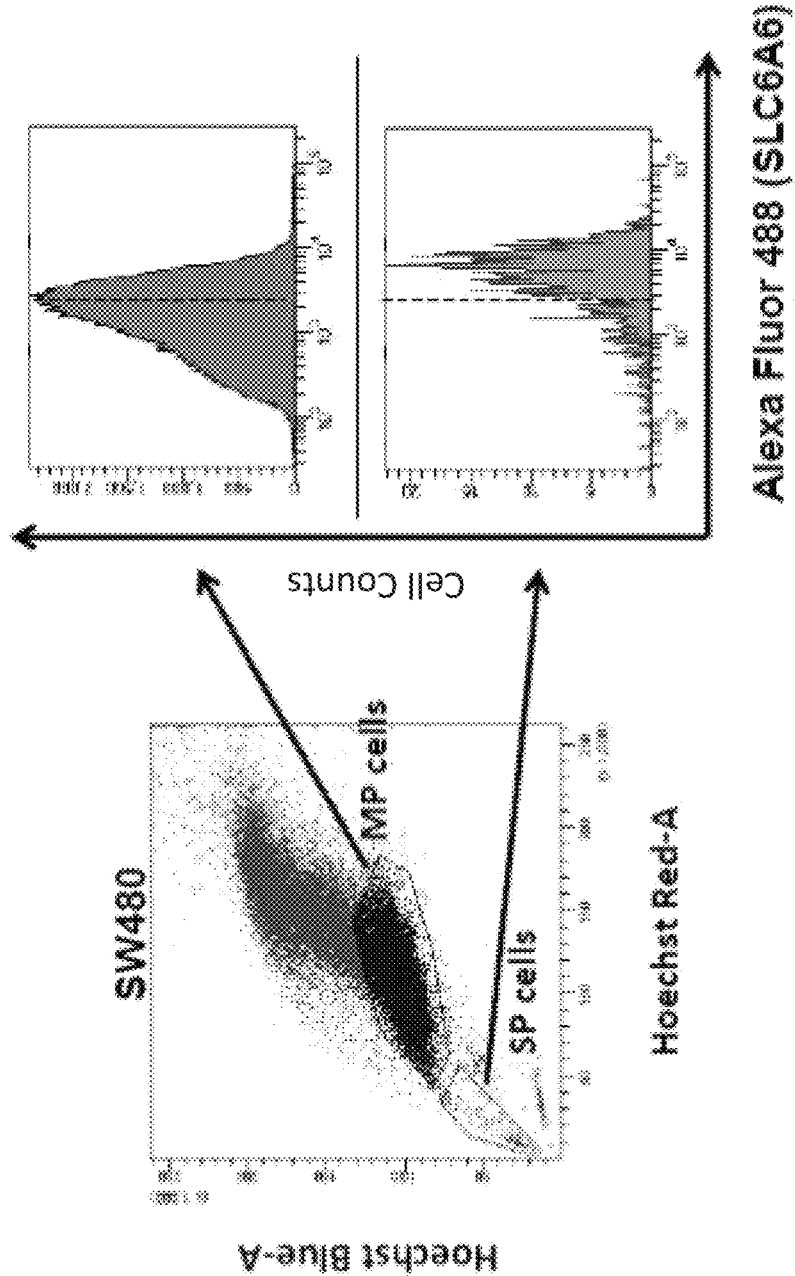
FIG. 9 shows the results compared and analyzed for the expression level of SLC6A6 between populations of SP cells and non-SP cells.

FIG. 9 shows that when SP and MP cells are stained for SLC6A6, the SP cells are more strongly stained with the antibody than the MP cells. Namely, it was indicated that SLC6A6 was expressed at a higher level in the SP cells than in the MP cells. It should be noted that in the absence of the antibody, both SP and MP cells showed no signal shift, thus indicating that the 430 antibody specifically reacted with SLC6A6. Further, in the presence of verapamil, no SP cells were observed, and hence the fraction separated as SP cells was confirmed to be SP cells.

Example 10

Ratio of SP Cells Upon Addition of Taurine

As shown in Example 9 above, SLC6A6 expression is directly involved in the formation of SP cells, which are a population enriched with cancer stem cells. On the other hand, SLC6A6 is reported to be a transporter responsible for transport of taurine (FEBS Letter 1993, 318, p. 139-144). In light of this finding, analysis was conducted to determine whether the ratio of SP cells in a population of cells engineered to overexpress SLC6A6 was changed upon treatment with taurine.

For this analysis, Colo320 cells (which are human colorectal cancer cells) were engineered to overexpress SLC6A6 and cultured for 2 days in a medium supplemented with taurine at a concentration of 0.05 mM, 0.1 mM, 0.5 mM, 1 mM or 5 mM, and then analyzed for SP cells in the same manner as shown in Example 1(3). The results obtained are shown in FIG. 10.

Figure 10:
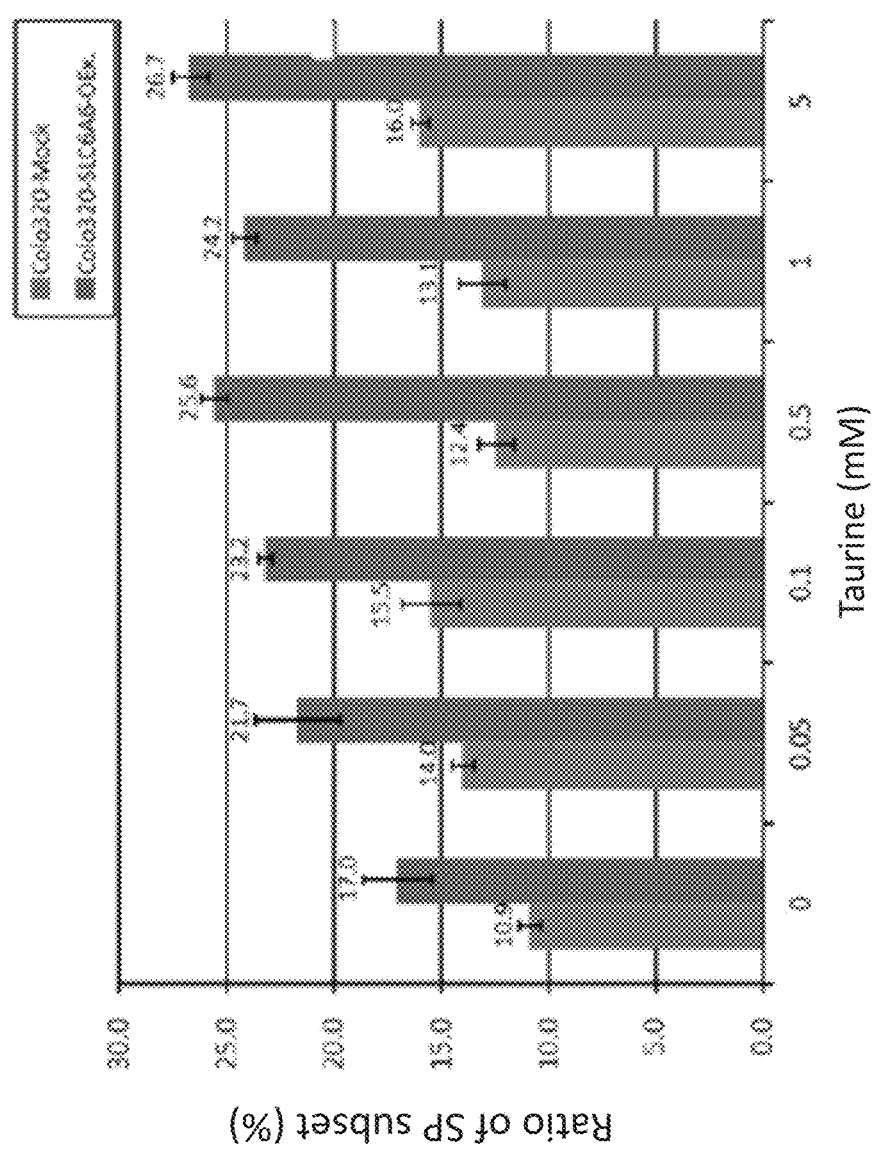
FIG. 10 shows the results analyzed for the ratio of SP cells upon addition of taurine to the medium.

FIG. 10 shows that the number of SP cells is increased in a manner dependent on the added concentration of taurine in both Colo320-Mock (i.e., Colo320 cells transformed with the vector alone) and Colo320-SLC6A6-OEx stably expressing SLC6A6. The action of taurine was significant particularly in Colo320-SLC6A6-OEx, and the ratio thereof was increased about 2.5-fold in the presence of 5 mM taurine when compared to the absence of taurine (0 mM) (i.e., increased from 17.0% to 26.7%). Namely, it was indicated that taurine uptake was increased upon enhancement of SLC6A6 expression, or that SP cells increased in number with increase in the concentration of taurine. Since SP cells are a fraction enriched with cancer stem cells, SLC6A6 was shown to have the potential to be involved in the conversion of cancer cells into stem cells.

Example 11

Analysis of Internalization (1) HT-29 or SW480 cells were cultured to reach 90% confluency and seeded in Glass Base Dishes. After being cultured for 24 hours, the cells were washed with ice-cold PBS and reacted for 1 hour at 4° C. with the 419, 402 or 430 antibody (10 µg/ml) purified at pH 3.0 after expression. The cells were washed with PBS and then cultured at 4° C. or 37° C. for 20 minutes, and then fixed with 10% neutral buffered formalin for 10 minutes. The reacted cells were reacted at room temperature for 30 minutes with 500-fold diluted anti-mouse IgG polyclonal antibody-Alexa Fluor 488 label and then analyzed under a confocal laser scanning microscope (Zeiss). The results obtained are shown in FIG. 11A.

FIG. 11A shows that the cells are stained on their cell membrane when reacted at 4° C., i.e., under conditions where the cells stop their activity and hence their intracellular transport mechanisms do not function, so that internalization does not occur. This result indicates that the antibody is located on the cell membrane. On the other hand, this figure shows that the cell membrane was not stained at 37° C. where internalization was caused. This result indicates that the antibody bound to the cell surface is transferred into the cells through internalization. Since the antibody taken up into the cells is localized in endosomes and lysosomes, strong dot-like signals were observed within the cells.

(2) Analysis was conducted to determine whether the antibody clone 402 human-mouse chimeric antibody prepared in Example 7 above was taken up into cells through internalization after binding onto their cell surface.

HCT116 cells (which are human colorectal cancer cells) or SK-BR3 cells (which are human breast cancer cells) were added at a density of 1×10⁴ cells/well onto glass bottom dishes (MATSUNAMI) and cultured at 37° C. under 5% $CO_2$ for 16 hours. After removal of the medium, fresh medium cooled on ice was added and the cells were allowed to stand on ice for 20 minutes. After removal of the medium, the 402 human-mouse chimeric antibody purified with Protein G and eluted with an eluent of pH 3.0 was added as a primary antibody after being prepared at a concentration of 20 µg/mL in the medium, followed by reaction on ice for 30 minutes. After being washed twice with the medium, the cells were reacted on ice for 30 minutes with anti-human IgG polyclonal antibody-Alexa Fluor 488 label as a secondary antibody. After being washed twice with the medium, the cells were cultured at 37° C. under 5% $CO_2$ for 0, 15, 30, 60 or 120 minutes and washed twice with PBS(−), followed by analysis under a fluorescence microscope (BZ8100, Keyence Corporation, Japan). The results obtained are shown in FIG. 11B.

Figure 11B:
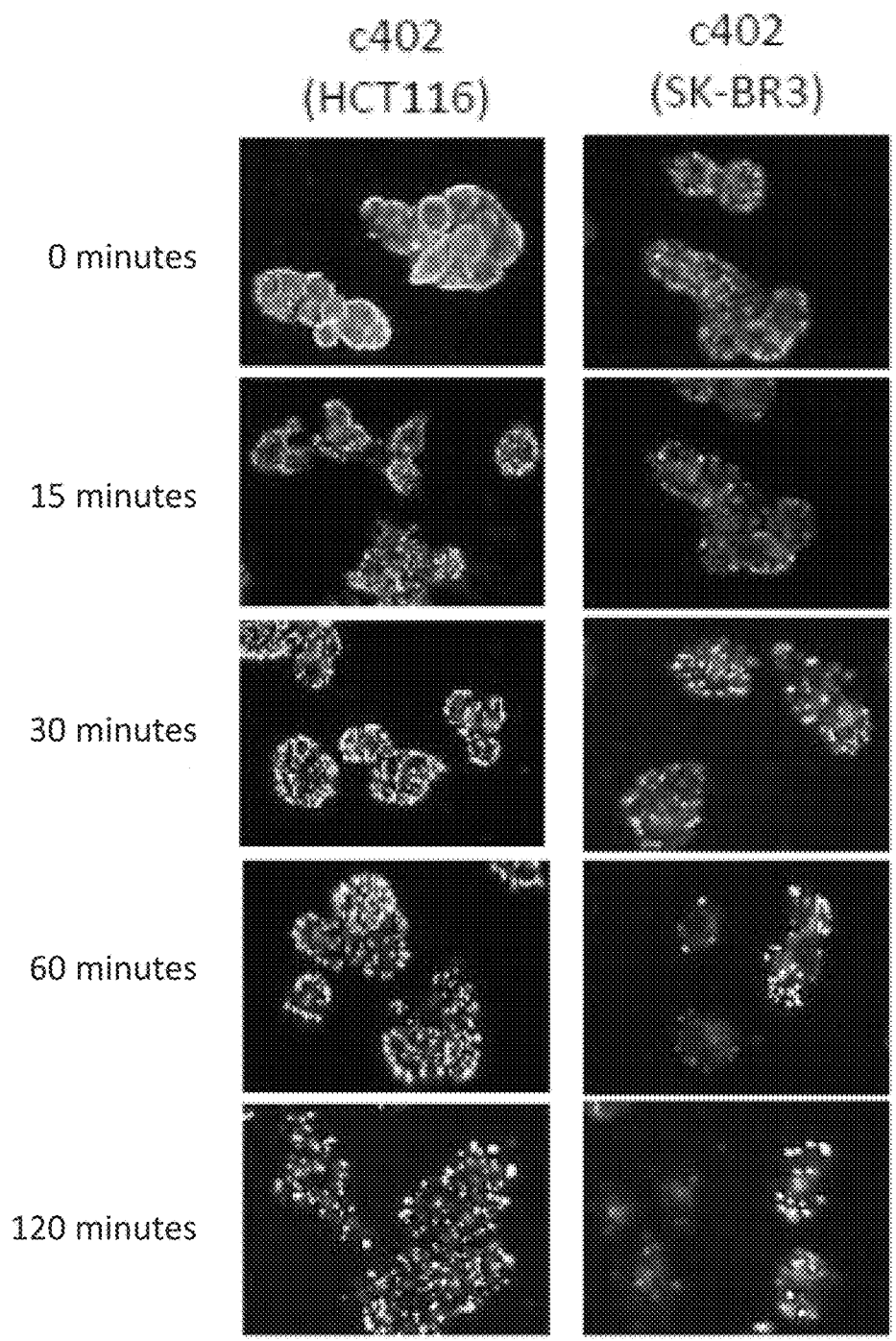
FIG. 11B shows the analysis on whether or not c402 antibody (402 human-mouse chimeric antibody) reacted with human colorectal cancer cells (HCT116 cells) or human breast cancer cells (SK-BR3 cells) is internalized.

FIG. 11B shows that the antibody is taken up over time into the cells in HCT116 or SK-BR3. At 0 minutes, i.e., immediately after staining, most of the antibody molecules were bound onto the cell membrane. However, the antibody molecules started to be taken up into the cells after 15 minutes, and most of the antibody molecules were taken up into the cells until 60 minutes. Namely, it was confirmed that the 402 human-mouse chimeric antibody was taken up into the cells after binding to SLC6A6 on the cell surface.

Example 12

Analysis of Internalization Mechanism

Internalization is mediated by cellular endocytosis. Endocytosis is classified into the following major types, i.e., clathrin-dependent endocytosis, caveolae-dependent endocytosis, phagocytosis and pinocytosis, depending on the type and size of substances to be taken up, differences in cellular molecules to be involved, etc.

Membrane proteins such as receptors are often taken up through clathrin-dependent endocytosis, and endocytosis inhibitors are used for their analysis.

Concanavalin A (ConA) serving as an inhibitor of clathrin-dependent endocytosis was used to analyze whether the internalization observed in Example 11 for the 402 human-mouse chimeric antibody was inhibited.

(1) Analysis with Secondary Antibody

To HCT116 cells cultured on glass bottom dishes in the same manner as shown in Example 11(2) above, a medium supplemented with ConA at a concentration of 0.5 mg/mL was added and cultured at 37° C. under 5% $CO_2$ for 60 minutes. After being washed twice with the medium, the cells were stained with a primary antibody and a secondary antibody in the same manner as shown in Example 13(2), followed by analysis under a fluorescence microscope after 0, 15, 30, 60 or 120 minutes.

Figure 12:
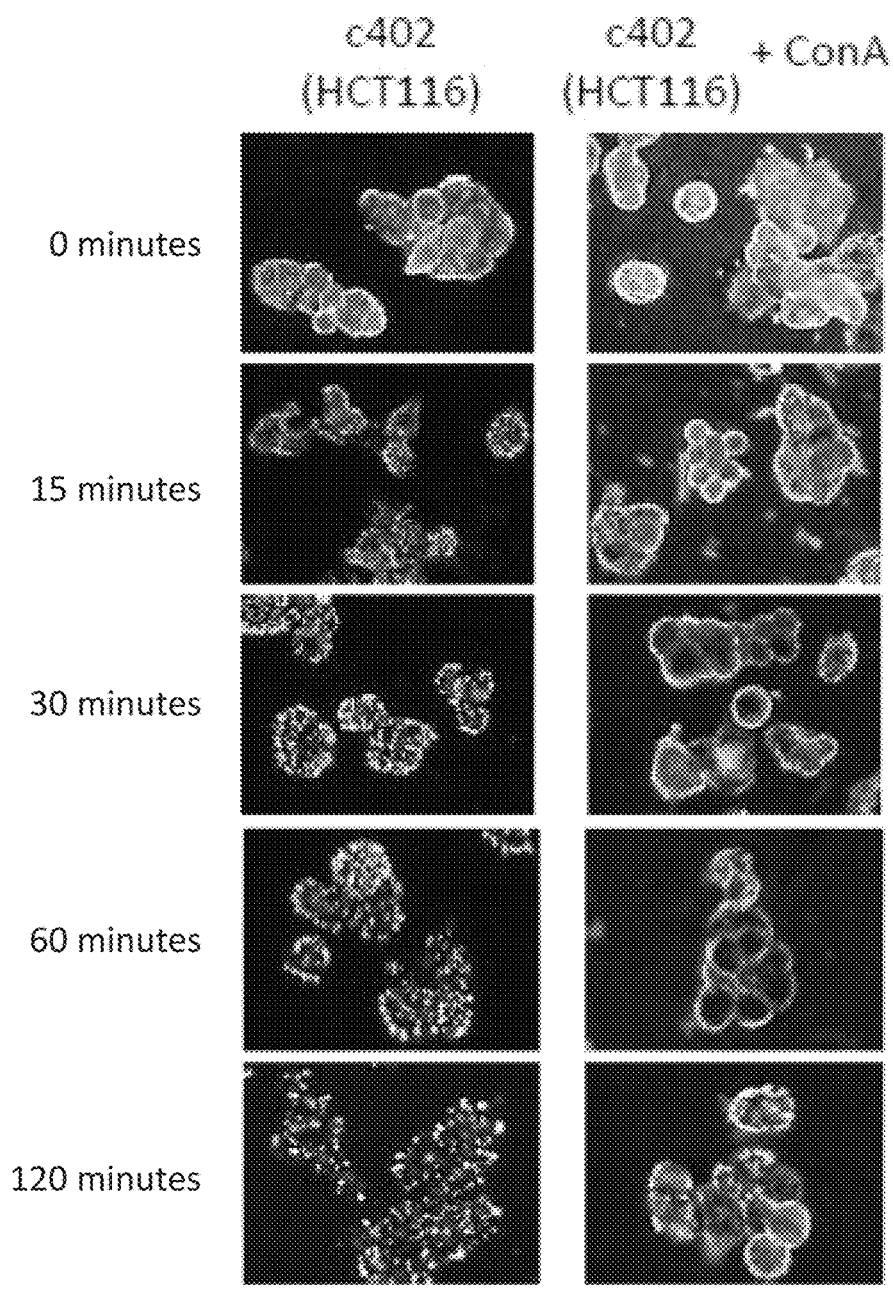
FIG. 12 shows the analysis on whether or not the internalization of c402 antibody is inhibited by Concanavalin A (ConA).

FIG. 12 shows that upon pre-treatment with ConA, internalization of the 402 human-mouse chimeric antibody is inhibited during the period observed. The left panel shows time-dependent changes in the absence of ConA, while the right panel shows the results obtained in the presence of ConA. It was indicated that upon pre-treatment with ConA, the antibody remained on the cell surface even during the culture period where the antibody should have been transported into the cells. This confirmed that the 402 human-mouse chimeric antibody bound to SLC6A6 on the cell membrane was taken up into the cells through clathrin-dependent endocytosis.

(2) Analysis with Fluorescently Labeled Antibody

Figure 13A:
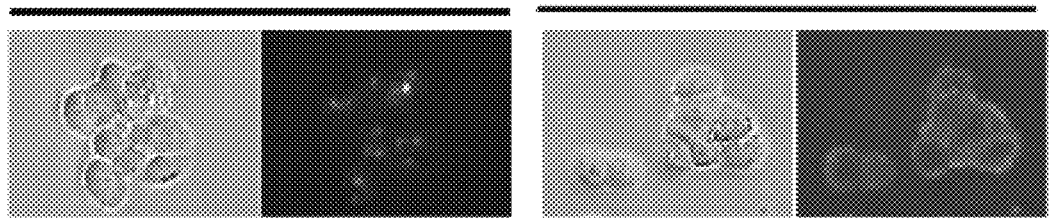
FIG. 13A shows the analysis on the internalization of c402 antibody when labeled directly with a fluorescent dye.

The 402 human-mouse chimeric antibody was labeled using an Alexa Fluor 488 Labeling Kit (Molecular Probe). Two cases were prepared where HCT116 cells were treated with ConA and not treated with ConA, respectively. After being allowed to stand on ice for 20 minutes, the HCT116 cells of each case were reacted on ice for 30 minutes with the Alexa Fluor 488-labeled 402 human-mouse chimeric antibody diluted to 30 µg/mL with the medium, and then washed twice with PBS(−), followed by analysis under a fluorescence microscope (FIG. 13A).

Analysis was performed on an isotype control (whole human IgG was used as a negative control), cetuximab (Cetuximab), the 402 human-mouse chimeric antibody (Chimeric 402), the 430 human-mouse chimeric antibody (Chimeric 430) and the 4B9b human-mouse chimeric antibody (Chimeric 4B9b), each being labeled with Alexa Fluor 488. These antibodies were analyzed for their internalization by flow cytometry using cells treated in two ways.

Figure 13B:
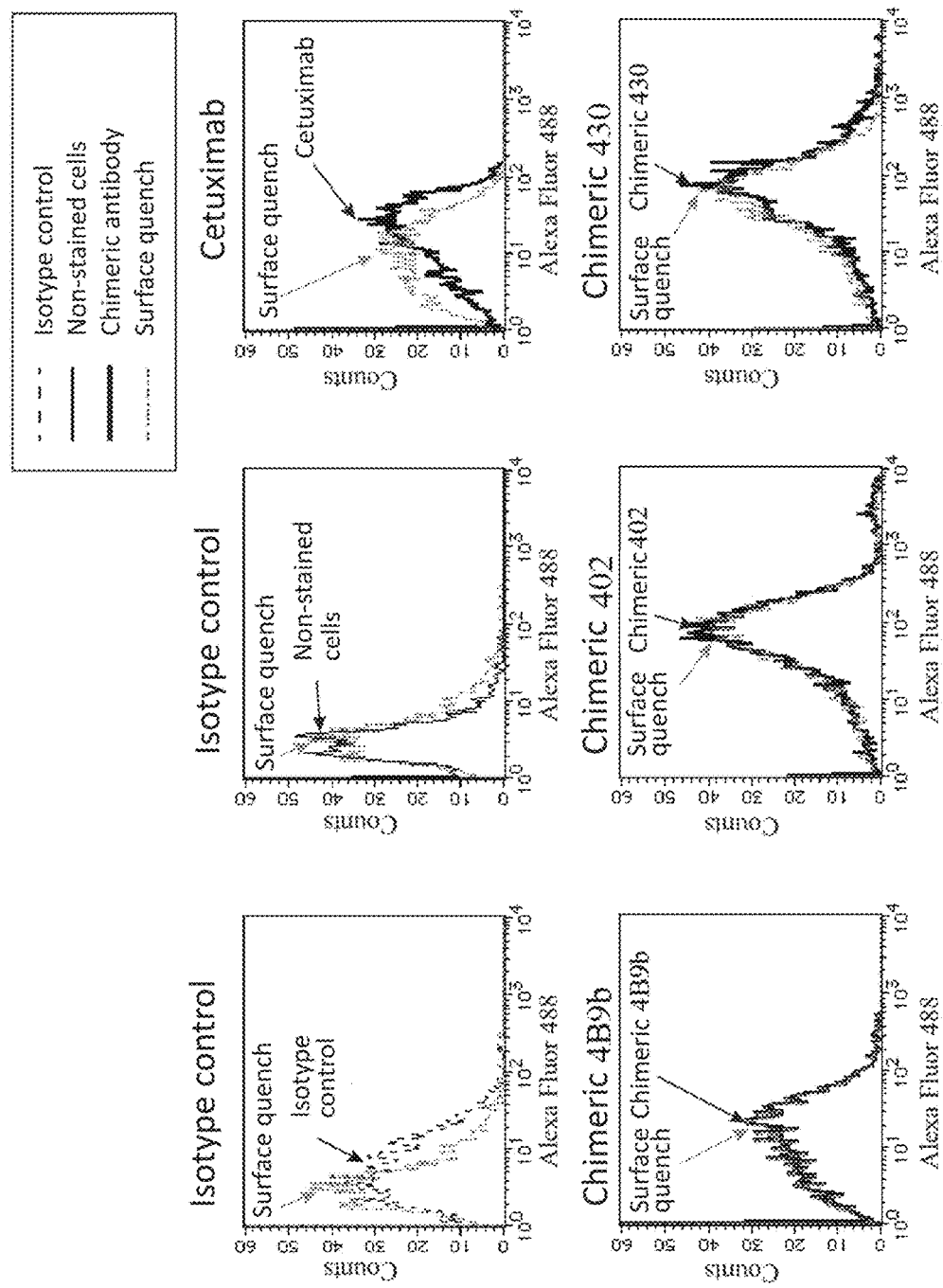
FIG. 13B shows the analysis on the internalization of "isotype control (Isotype control)" (whole human IgG was used as a negative control), "cetuximab (Cetuximab)," "402 human-mouse chimeric antibody (Chimeric 402)," "430 human-mouse chimeric antibody (Chimeric 430)" and "4B9b human-mouse chimeric antibody (Chimeric 4B9b)," each being directly labeled with a fluorescent dye.

For the first way, the following operations were performed. Cells detached from culture dishes were suspended in staining buffer [PBS(−)-3% fetal bovine serum]. To this cell suspension, protease inhibitors were added (final concentration: 10 µg/mL leupeptin, 5 µM pepstatin) to prevent antibody molecules from being degraded in lysosomes after being taken up into the cells. Each Alexa Fluor 488-labeled antibody was added to the cell suspension at a final concentration of 30 µg/mL and then rotated with a rotator at room temperature for 1 hour. After being further rotated with a rotator at 37° C. for 3 hours, the cells were washed three times with the staining buffer and then measured for fluorescence signals by flow cytometry (FIG. 13B; isotype control, chimeric antibody).

The second way is to confirm that the fluorescence in the cells obtained in the first way arises from the dye conjugated to the antibody taken up into the cells. The cells obtained in the first way were reacted at 4° C. for 1 hour with an antibody binding to Alexa Fluor 488 and thereby quenching its fluorescence (anti-Alexa Fluor 488, rabbit IgG antibody fraction: anti-Alexa Fluor 488 antibody) at a final concentration of 50 µg/mL to observe changes in fluorescence intensity (FIG. 13B; surface quench). In this case, fluorescence from the antibody remaining on the cell surface is quench with the anti-Alexa Fluor 488 antibody, whereas fluorescence from the antibody transferred into the cells is not quenched with the anti-Alexa Fluor 488 antibody.

Thus, the difference in the amount of fluorescence from the cells obtained in two ways can be used to determine what proportion of the antibody bound to the cell membrane was taken up into the cells.

FIG. 13A shows that the directly labeled 402 human-mouse chimeric antibody (c402) is taken up into the cells even on ice. When the cells were reacted on ice for 30 minutes without being treated with ConA, fluorescence from Alexa Fluor 488 was mostly observed within the cells. On the other hand, in the case of the cells treated with ConA, fluorescence from Alexa Fluor 488 remained on the cell membrane surface. This confirmed that internalization of the 402 human-mouse chimeric antibody proceeded even on ice (about 1° C.).

In FIG. 13B, internalization was analyzed by being measured by flow cytometry. Signals from the isotype control were reduced to the same level as in the non-stained cells upon addition of the anti-Alexa Fluor 488 antibody (surface quench). This indicates that the fluorescence observed on the cell surface is quenched with the anti-Alexa 488 antibody. Moreover, in the case of cetuximab (Erbitux®) which is an anti-EGFR antibody and has been intently studied for its uptake into cancer cells through internalization in a drug-conjugated state, the fluorescence partially disappeared upon reaction with the anti-Alexa Fluor 488 antibody (surface quench). On the other hand, in the 402, 430 and 4B9b mouse-human chimeric antibodies, the fluorescence did not disappear even upon addition of the anti-Alexa Fluor 488 antibody. These results mean that the anti-SLC6A6 monoclonal antibodies of the present invention are internalized into the cells, but are not simply bound to SLC6A6 on the cell surface, and that a larger number of antibody molecules are taken up into the cells than in the case of cetuximab. Further, the 402 and 430 human-mouse chimeric antibodies were more efficiently taken up into the cells than the 4B9b human-mouse chimeric antibody.

In light of these results in this example, the antibody conjugate of the present invention can be expected to exert more potent cytotoxic activity when the antibody is conjugated with a cytotoxic substance (e.g., a toxin or a radioactive substance) instead of a dye. Thus, the antibody conjugate of the present invention and a composition comprising the same are assumed to be more effective as pharmaceutical preparations (e.g., pharmaceutical preparations for cancer treatment).

Moreover, anti-ERBB2 antibody (trastuzumab), which has been extensively analyzed as an internalizing antibody, is not reported to be taken up into cells when reacted on ice. In light of this fact, internalization of the 402 human-mouse chimeric antibody is considered to proceed very efficiently. Namely, it is considered that cancer cells can be killed with the antibody-drug conjugate even at low concentration due to its very high uptake efficiency.

Example 13

(1) Effect of Antibody-Drug Conjugate

Analysis was conducted to determine whether the proliferation of cancer cells was able to be suppressed by means of the antibody's property of being taken up into cells. HT-29 or SW480 cells were reacted for 1 hour at 4° C. with 10 μg/mL of the 419 antibody purified at pH 3.0, and then washed with PBS. To this, saporin-labeled anti-mouse IgG polyclonal antibody (ADVANCED TARGETING SYSTEMS) or unlabeled anti-mouse IgG polyclonal antibody was added at a concentration of 10 μM and reacted for 30 minutes at 4° C., followed by washing with PBS. Saporin has ribosome-inactivating activity and suppresses cell proliferation only when taken up into cells. After these cells were cultured at 37° C. for 3 days, their proliferation was measured using WST-8 (Roche). The results obtained are shown in FIG. 14A.

Figure 14B:
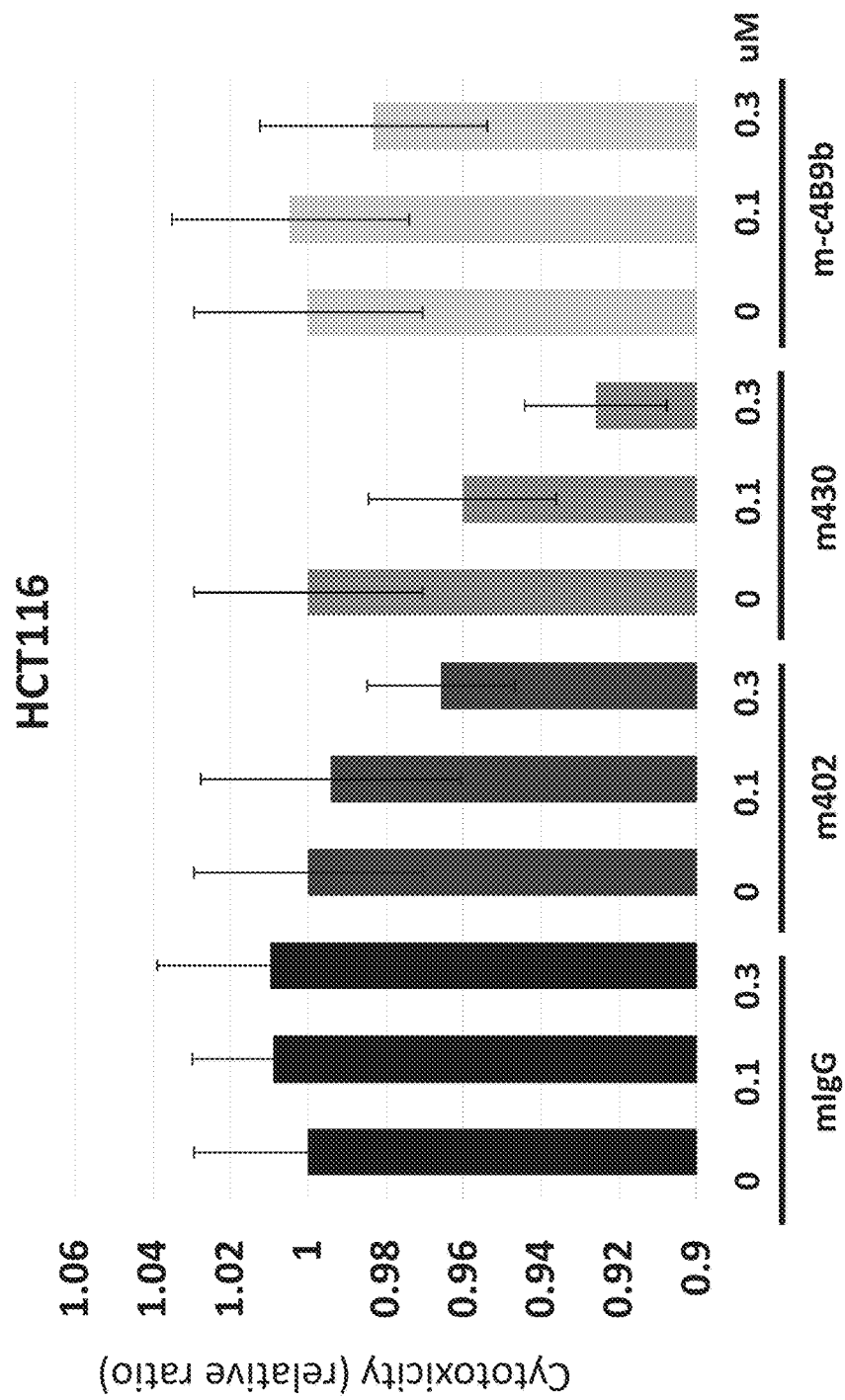
FIG. 14B shows the results indicating that upon reaction between anti-mouse antibody labeled with saporin (which is a ribosome inhibitory toxin) and 402 antibody, 430 antibody or monoclonal antibody mouse IgG-converted 4B9b antibody, toxicity is exerted when the antibodies are taken up into cells through internalization.

In FIG. 14A, black represents cell proliferation in the absence of the saporin-labeled secondary antibody, while gray represents cell proliferation upon addition of the saporin-labeled antibody at a concentration of 10 nM. FIG. 14A shows that cell proliferation is suppressed in both HT-29 and SW480 cases upon addition of the saporin-labeled secondary antibody. Namely, it was indicated that as a result of reaction between the anti-mouse antibody labeled with saporin (which is a ribosome inhibitory toxin) and the mouse monoclonal antibody, these antibodies were taken up into cells to thereby suppress the proliferation of cancer cells.

(2) Effect of the Use of Saporin-Labeled Secondary Antibody

Analysis was conducted to determine whether the proliferation of cancer cells was able to be suppressed by means of the antibody's property of being taken up into cells. HCT116 cells (which are human colorectal cancer cells) were seeded in 96-well plates at a density of $2.5 \times 10^3$ cells/well and cultured at 37° C. under 5% $CO_2$ for 16 hours. To these HCT116 cells, a mixed solution was added which had been prepared to contain each mouse antibody at a final concentration of 0.1 or 0.3 μM and saporin-labeled anti-mouse IgG polyclonal antibody (ADVANCED TARGETING SYSTEMS) at a final concentration of 9 nM. Saporin has ribosome-inactivating activity and suppresses cell proliferation only when taken up into cells. After these cells were cultured at 37° C. under 5% $CO_2$ for 3 days, their proliferation was measured using a Cell Counting Kit-8 (Dojindo Laboratories, Japan). The results obtained are shown in FIG. 14.

FIG. 14 shows that only when the mouse 402 or 430 antibody was added to HCT116 cells, their proliferation is suppressed in a manner dependent on the antibody concentration. Namely, it was indicated that as a result of reaction between the anti-mouse antibody labeled with saporin (which is a ribosome inhibitory toxin) and the mouse 402 or 430 antibody, these antibodies were taken up into cells to thereby suppress the proliferation of cancer cells. In light of this result, when used as a conjugate with a drug, the 402 or 430 antibody is shown to have high cytotoxic activity and can be expected to have a high antitumor effect when formulated into pharmaceutical preparations.

SEQ ID NO: 1: nucleotide sequence encoding human SLC6A6
SEQ ID NO: 2: amino acid sequence of human SLC6A6
SEQ ID NO: 3: nucleotide sequence encoding an amino acid sequence covering amino acid residues 143 to 216 of human SLC6A6
SEQ ID NO: 4: amino acid sequence covering amino acid residues 143 to 216 of human SLC6A6
SEQ ID NO: 5: primer sequence, Forward
SEQ ID NO: 6: primer sequence, Reverse
SEQ ID NO: 7: primer sequence, Long
SEQ ID NO: 8: primer sequence, Short
SEQ ID NO: 9: primer sequence, mIgG2a_CH1_reverse
SEQ ID NO: 10: primer sequence, mIgkappa_R3
SEQ ID NO: 11: oligo DNA sequence, hHchain
SEQ ID NO: 12: primer sequence, hCg1_F
SEQ ID NO: 13: primer sequence, hCgI_R
SEQ ID NO: 14: primer sequence, Hchain_signal_top
SEQ ID NO: 15: primer sequence, Hchain_signal_bottom
SEQ ID NO: 16: primer sequence, Forward
SEQ ID NO: 17: primer sequence, Reverse
SEQ ID NO: 18: oligo DNA sequence, hLchain
SEQ ID NO: 19: primer sequence, hCk_F
SEQ ID NO: 20: primer sequence, hCk_R
SEQ ID NO: 21: primer sequence, Forward2
SEQ ID NO: 22: primer sequence, Reverse2
SEQ ID NO: 23: nucleotide sequence encoding the heavy chain of human-mouse chimeric 205 antibody
SEQ ID NO: 24: amino acid sequence of the heavy chain of human-mouse chimeric 205 antibody
SEQ ID NO: 25: nucleotide sequence encoding the light chain of human-mouse chimeric 205 antibody
SEQ ID NO: 26: amino acid sequence of the light chain of human-mouse chimeric 205 antibody
SEQ ID NO: 27: nucleotide sequence encoding the heavy chain of human-mouse chimeric 402 antibody
SEQ ID NO: 28: amino acid sequence of the heavy chain of human-mouse chimeric 402 antibody
SEQ ID NO: 29: nucleotide sequence encoding the light chain of human-mouse chimeric 402 antibody
SEQ ID NO: 30: amino acid sequence of the light chain of human-mouse chimeric 402 antibody
SEQ ID NO: 31: nucleotide sequence encoding the heavy chain of human-mouse chimeric 419 antibody
SEQ ID NO: 32: amino acid sequence of the heavy chain of human-mouse chimeric 419 antibody
SEQ ID NO: 33: nucleotide sequence encoding the light chain of human-mouse chimeric 419 antibody SEQ ID NO: 34: amino acid sequence of the light chain of human-mouse chimeric 419 antibody SEQ ID NO: 35: nucleotide sequence encoding the heavy chain of human-mouse chimeric 303 antibody SEQ ID NO: 36: amino acid sequence of the heavy chain of human-mouse chimeric 303 antibody SEQ ID NO: 37: nucleotide sequence encoding the light chain of human-mouse chimeric 303 antibody SEQ ID NO: 38: amino acid sequence, of the light chain of human-mouse chimeric 303 antibody SEQ ID NO: 39: nucleotide sequence encoding the heavy chain of human-mouse chimeric 422 antibody SEQ ID NO: 40: amino acid sequence of the heavy chain of human-mouse chimeric 422 antibody SEQ ID NO: 41: nucleotide sequence encoding the light chain of human-mouse chimeric 422 antibody SEQ ID NO: 42: amino acid sequence of the light chain of human-mouse chimeric 422 antibody SEQ ID NO: 43: nucleotide sequence encoding the heavy chain of human-mouse chimeric 430 antibody SEQ ID NO: 44: amino acid sequence of the heavy chain of human-mouse chimeric 430 antibody SEQ ID NO: 45: nucleotide sequence encoding the light chain of human-mouse chimeric 430 antibody SEQ ID NO: 46: amino acid sequence of the light chain of human-mouse chimeric 430 antibody

INDUSTRIAL APPLICABILITY

The present invention provides a monoclonal antibody specifically binding to the extracellular region of SLC6A6. Moreover, the present invention provides an antibody conjugate comprising an anti-SLC6A6 monoclonal antibody or an antigen-binding fragment thereof and at least one anti-cancer agent, toxin or radioisotope linked thereto, as well as a pharmaceutical composition comprising such an antibody conjugate. Since the monoclonal antibody of the present invention specifically binds to cancer cells expressing SLC6A6 and is thereby internalized in these cells, the antibody conjugate and the pharmaceutical composition according to the present invention are useful for cancer treatment, particularly as a pharmaceutical composition for colorectal cancer treatment. The antibody may be humanized or chimeric, and it is therefore possible to reduce side effects upon application to humans.

Sequence Listing Free Text

SEQ ID NOs: 5 to 46: synthetic DNAs

The invention claimed is:

1. A monoclonal antibody or antigen-binding fragment thereof, wherein the antibody or antigen-binding fragment thereof binds SLC6A6, wherein the monoclonal antibody is at least one selected from the group consisting of:

(a) an antibody which comprises a heavy chain variable region comprising amino acid sequences located at positions 50 to 54, positions 69 to 86 and positions 118 to 125 in SEQ ID NO: 24 as heavy chain CDR1, CDR2 and CDR3, respectively, and a light chain variable region comprising amino acid sequences located at positions 44 to 54, positions 70 to 76 and positions 109 to 116 in SEQ ID NO: 26 as light chain CDR1, CDR2 and CDR3, respectively;

(b) an antibody which comprises a heavy chain variable region comprising amino acid sequences located at positions 50 to 54, positions 69 to 86 and positions 118 to 126 in SEQ ID NO: 28 as heavy chain CDR1, CDR2 and CDR3, respectively, and a light chain variable region comprising amino acid sequences located at positions 46 to 57, positions 73 to 79 and positions 112 to 119 in SEQ ID NO: 30 as light chain CDR1, CDR2 and CDR3, respectively;

(c) an antibody which comprises a heavy chain variable region comprising amino acid sequences located at positions 50 to 54, positions 69 to 86 and positions 118 to 128 in SEQ ID NO: 32 as heavy chain CDR1, CDR2 and CDR3, respectively, and a light chain variable region comprising amino acid sequences located at positions 48 to 58, positions 74 to 80 and positions 113 to 120 in SEQ ID NO: 34 as light chain CDR1, CDR2 and CDR3, respectively;

(d) an antibody which comprises a heavy chain variable region comprising amino acid sequences located at positions 50 to 54, positions 69 to 86 and positions 118 to 131 in SEQ ID NO: 36 as heavy chain CDR1, CDR2 and CDR3, respectively, and a light chain variable region comprising amino acid sequences located at positions 44 to 54, positions 70 to 76 and positions 109 to 116 in SEQ ID NO: 38 as light chain CDR1, CDR2 and CDR3, respectively;

(e) an antibody which comprises a heavy chain variable region comprising amino acid sequences located at positions 50 to 54, positions 69 to 86 and positions 118 to 129 in SEQ ID NO: 40 as heavy chain CDR1, CDR2 and CDR3, respectively, and a light chain variable region comprising amino acid sequences located at positions 44 to 54, positions 70 to 76 and positions 109 to 116 in SEQ ID NO: 42 as light chain CDR1, CDR2 and CDR3, respectively; and (f) an antibody which comprises a heavy chain variable region comprising amino acid sequences located at positions 50 to 54, positions 69 to 86 and positions 118 to 126 in SEQ ID NO: 44 as heavy chain CDR1, CDR2 and CDR3, respectively, and a light chain variable region comprising amino acid sequences located at positions 46 to 57, positions 73 to 79 and positions 112 to 119 in SEQ ID NO: 46 as light chain CDR1, CDR2 and CDR3, respectively.

* * * * *